United States Patent
Issa et al.

(10) Patent No.: US 11,866,696 B2
(45) Date of Patent: Jan. 9, 2024

(54) ANALYTICAL HPLC METHODS

(71) Applicant: ModernaTX, Inc., Cambridge, MA (US)

(72) Inventors: William Issa, Dedham, MA (US); Meredith Packer, Waltham, MA (US)

(73) Assignee: ModernaTX, Inc., Cambridge, MA (US)

( * ) Notice: Subject to any disclaimer, the term of this patent is extended or adjusted under 35 U.S.C. 154(b) by 601 days.

(21) Appl. No.: 16/639,265

(22) PCT Filed: Aug. 17, 2018

(86) PCT No.: PCT/US2018/046990
§ 371 (c)(1),
(2) Date: Feb. 14, 2020

(87) PCT Pub. No.: WO2019/036683
PCT Pub. Date: Feb. 21, 2019

(65) Prior Publication Data
US 2020/0239869 A1     Jul. 30, 2020

Related U.S. Application Data

(60) Provisional application No. 62/547,462, filed on Aug. 18, 2017.

(51) Int. Cl.
*C12N 15/10*     (2006.01)
*A61K 48/00*     (2006.01)
(Continued)

(52) U.S. Cl.
CPC ........ *C12N 15/101* (2013.01); *A61K 48/0091* (2013.01); *C12Q 1/6876* (2013.01);
(Continued)

(58) Field of Classification Search
CPC .............. A61K 48/0091; C12N 15/101; C12Q 1/6876; G01N 2030/027; G01N 2030/8827; G01N 30/34; G01N 30/50
See application file for complete search history.

(56) References Cited

U.S. PATENT DOCUMENTS

6,022,715 A     2/2000   Merenkova et al.
6,100,024 A     8/2000   Hudson et al.
(Continued)

FOREIGN PATENT DOCUMENTS

EP           2092064           9/2010
WO     WO 2003/031580 A2     4/2003
(Continued)

OTHER PUBLICATIONS

Ståhlberg et al ("Chromatography: Liquid | Ion Pair Liquid Chromatography"), Editor(s): Ian D. Wilson, Encyclopedia of Separation Science, Academic Press, 2000, pp. 676-684, ISBN 9780122267703, https://doi.org/10.1016/B0-12-226770-2/01591-X (Year: 2000).*

(Continued)

*Primary Examiner* — Christine T Mui
*Assistant Examiner* — Jonathan Bortoli

(57) ABSTRACT

Aspects of the disclosure relate to liquid chromatography (e.g., HPLC) methods which enable high resolution separations of polynucleotides of various lengths, sequences, and/or base compositions in a highly tunable manner. In some embodiments, the disclosure describes liquid chromatographic methods for separating a nucleic acid (e.g., a polyadenylated nucleic acid, such as an mRNA) from a complex mixture by using multiple ion pairing agents in the same mobile phase system. Accordingly, in some embodiments methods described by the disclosure are useful for assessing the quality of pharmaceutical preparations comprising nucleic acids.

16 Claims, 36 Drawing Sheets

(51) Int. Cl.
*C12Q 1/6876* (2018.01)
*G01N 30/34* (2006.01)
*G01N 30/02* (2006.01)
*G01N 30/88* (2006.01)

(52) U.S. Cl.
CPC ....... *G01N 30/34* (2013.01); *G01N 2030/027* (2013.01); *G01N 2030/8827* (2013.01)

(56) References Cited

U.S. PATENT DOCUMENTS

| | | |
|---|---|---|
| 6,969,587 B2 | 11/2005 | Taylor |
| 7,135,289 B2 | 11/2006 | Tayler et al. |
| 8,383,340 B2 | 2/2013 | Ketterer et al. |
| 8,710,200 B2 | 4/2014 | Schrum et al. |
| 8,754,062 B2 | 6/2014 | De Fougerolles et al. |
| 8,822,663 B2 | 9/2014 | Schrum et al. |
| 8,980,864 B2 | 3/2015 | Hoge et al. |
| 8,999,380 B2 | 4/2015 | Bancel et al. |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,572,896 B2 | 2/2017 | Bancel et al. |
| 9,597,380 B2 | 3/2017 | Chakraborty et al. |
| 9,675,668 B2 | 6/2017 | Bancel et al. |
| 9,868,691 B2 | 1/2018 | Benenato et al. |
| 9,872,900 B2 | 1/2018 | Ciaramella et al. |
| 10,023,626 B2 | 7/2018 | Bolen et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,027,025 B2 | 6/2021 | Hoge et al. |
| 11,045,540 B2 | 6/2021 | Ciaramella |
| 11,103,578 B2 | 8/2021 | Ciaramella et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 11,497,807 B2 | 11/2022 | Ciaramella et al. |
| 11,564,893 B2 | 1/2023 | Smith |
| 11,576,961 B2 | 2/2023 | Ciaramella et al. |
| 11,643,441 B1 | 5/2023 | Ciaramella et al. |
| 11,696,946 B2 | 7/2023 | Ciaramella |
| 2002/0003109 A1 | 1/2002 | Gjerde et al. |
| 2008/0220471 A1 | 9/2008 | Davis et al. |
| 2010/0048883 A1 | 2/2010 | Ketterer et al. |
| 2013/0102034 A1 | 4/2013 | Schrum et al. |
| 2013/0236974 A1 | 9/2013 | De Fougerolles |
| 2013/0245103 A1 | 9/2013 | de Fougerolles et al. |
| 2013/0259923 A1 | 10/2013 | Bancel et al. |
| 2014/0142290 A1 | 5/2014 | Madden et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0064242 A1 | 3/2015 | Heyes et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0194368 A1 | 7/2016 | Hoge et al. |
| 2016/0243221 A1 | 8/2016 | Hoge et al. |
| 2016/0369243 A1* | 12/2016 | Kariko ............... C12N 9/0075 |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0125839 A1 | 5/2019 | Frederick et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0336452 A1 | 11/2019 | Brader |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129445 A1 | 4/2020 | Patel et al. |
| 2020/0129608 A1 | 4/2020 | Ciaramella et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |
| 2020/0338004 A1 | 10/2020 | Hansson et al. |
| 2020/0368162 A1 | 11/2020 | Martini |
| 2021/0046173 A1 | 2/2021 | Ciaramella et al. |
| 2021/0087135 A1 | 3/2021 | Benenato et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0309976 A1 | 10/2021 | Dousis et al. |
| 2021/0378980 A1 | 12/2021 | Horhota et al. |
| 2022/0031631 A1 | 2/2022 | Almarsson et al. |
| 2022/0047518 A1 | 2/2022 | Hennessy et al. |

(56) References Cited

U.S. PATENT DOCUMENTS

| | | | |
|---|---|---|---|
| 2022/0054653 | A1 | 2/2022 | Martini et al. |
| 2022/0062175 | A1 | 3/2022 | Smith et al. |
| 2022/0062408 | A1 | 3/2022 | Kramarczyk et al. |
| 2022/0125899 | A1 | 4/2022 | Ashburn et al. |
| 2022/0145381 | A1 | 5/2022 | Elich et al. |
| 2022/0236253 | A1 | 7/2022 | Hopson |
| 2022/0241399 | A1 | 8/2022 | Lusso et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2023/0000970 | A1 | 1/2023 | Nachbagauer et al. |
| 2023/0142529 | A1 | 5/2023 | White et al. |
| 2023/0181481 | A1 | 6/2023 | White et al. |
| 2023/0190761 | A1 | 6/2023 | Brader et al. |
| 2023/0212645 | A1 | 7/2023 | Marquardt et al. |

FOREIGN PATENT DOCUMENTS

| | | | |
|---|---|---|---|
| WO | WO2003031580 | * | 4/2003 |
| WO | WO 2005/118857 | | 12/2005 |
| WO | WO 2008/077592 | A1 | 7/2008 |
| WO | WO 2011/071931 | A2 | 6/2011 |
| WO | WO 2014/004281 | A1 | 1/2014 |
| WO | WO 2014/140211 | A1 | 9/2014 |
| WO | WO 2014/152966 | A1 | 9/2014 |
| WO | WO 2014/159813 | A1 | 10/2014 |
| WO | WO 2016/051170 | A1 | 4/2016 |
| WO | WO 2016/164762 | A1 | 10/2016 |
| WO | WO 2016/193206 | A1 | 12/2016 |
| WO | WO 2016/201377 | A1 | 12/2016 |
| WO | WO 2017/011773 | A2 | 1/2017 |
| WO | WO 2017/015457 | A1 | 1/2017 |
| WO | WO 2017/066789 | A1 | 4/2017 |
| WO | WO 2017/070601 | A1 | 4/2017 |
| WO | WO 2017/112865 | A1 | 6/2017 |
| WO | WO 2017/127750 | A1 | 7/2017 |
| WO | WO 2017/201333 | A1 | 11/2017 |
| WO | WP 2018/096179 | A1 | 5/2018 |
| WO | WO 2018/157009 | A1 | 8/2018 |
| WO | WO 2018/232355 | A1 | 12/2018 |
| WO | WO 2018/232357 | A1 | 12/2018 |
| WO | WO 2019/036683 | A1 | 2/2019 |
| WO | WO 2020/061367 | A1 | 3/2020 |
| WO | WO 2020/190750 | A1 | 9/2020 |
| WO | WO 2020/243561 | A1 | 12/2020 |
| WO | WO 2021/030533 | A1 | 2/2021 |
| WO | WO 2021/050864 | A1 | 3/2021 |
| WO | WO 2021/055811 | A1 | 3/2021 |
| WO | WO 2021/155243 | A1 | 8/2021 |
| WO | WO 2021/155274 | A1 | 8/2021 |
| WO | WO 2021/159040 | A2 | 8/2021 |
| WO | WO 2021/159130 | A2 | 8/2021 |
| WO | WO 2021/211343 | A1 | 10/2021 |
| WO | WO 2021/222304 | A1 | 11/2021 |
| WO | WO 2021/231929 | A1 | 11/2021 |
| WO | WO 2021/231963 | A1 | 11/2021 |
| WO | WO 2021/237084 | A1 | 11/2021 |
| WO | WO 2021/247817 | A1 | 12/2021 |
| WO | WO 2022/067010 | A1 | 3/2022 |
| WO | WO 2022/150717 | A1 | 7/2022 |
| WO | WO 2022/155524 | A1 | 7/2022 |
| WO | WO 2022/155530 | A1 | 7/2022 |
| WO | WO 2022/187698 | A1 | 9/2022 |
| WO | WO 2022/204497 | A1 | 9/2022 |
| WO | WO 2022/212191 | A1 | 10/2022 |
| WO | WO 2022/212442 | A1 | 10/2022 |
| WO | WO 2022/212711 | A2 | 10/2022 |
| WO | WO 2022/221335 | A1 | 10/2022 |
| WO | WO 2022/221336 | A1 | 10/2022 |
| WO | WO 2022/221359 | A1 | 10/2022 |
| WO | WO 2022/221440 | A1 | 10/2022 |
| WO | WO 2022/232585 | A1 | 11/2022 |
| WO | WO 2022/241103 | A1 | 11/2022 |
| WO | WO 2022/266010 | A1 | 12/2022 |
| WO | WO 2022/266012 | A1 | 12/2022 |
| WO | WO 2022/266389 | A1 | 12/2022 |
| WO | WO 2023/283642 | A2 | 1/2023 |
| WO | WO 2023/283645 | A1 | 1/2023 |
| WO | WO 2023/283651 | A1 | 1/2023 |
| WO | WO 2023/014649 | A1 | 2/2023 |
| WO | WO 2023/018773 | A1 | 2/2023 |
| WO | WO 2023/018923 | A1 | 2/2023 |
| WO | WO 2023/019181 | A1 | 2/2023 |
| WO | WO 2023/092069 | A1 | 5/2023 |
| WO | WO 2023/107999 | A2 | 6/2023 |
| WO | WO 2023/114307 | A1 | 6/2023 |
| WO | WO 2023/132885 | A1 | 7/2023 |

OTHER PUBLICATIONS

Gjerde et al "(RNA Purification and Analysis: Sample Preparation, Extraction, Chromatography") Wiley-VCH Verlag GmbH & Co. KGaA, Weinheim ISBN: 978-3-527-32116-2 (Year: 2009).*

Buszewski Hydrophilic interaction liquid chromatography (HILIC)—a powerful separation technique. Anal Bioanal Chem 402, 231-247 (2012). https://doi.org/10.1007/s00216-011-5308-5 (Year: 2012).*

Shibue et al ("Effect of anionic ion-pairing reagent concentration (1-60 mM) on reversed-phase liquid chromatography elution behaviour of peptides"). J Chromatogr A. 1080(1):58-67. doi: 10.1016/j.chroma.2005.02.047. PMID: 16013615; PMCID: PMC2744688. (Year: 2005).*

McCarthy "Hexylammonium Acetate as an Ion-Pairing Agent for IP-RP LC Analysis of Oligonucleotides" Waters (Year: 2016).*

Dickman "Enrichment and analysis of RNA centered on ion pair reverse phase methodology" RNA, vol. 12, No. 4 (Year: 2006).*

Basiri et al "The Role of Fluorinated Alcohols as Mobile Phase Modifiers for LC-MS Analysis of Oligonucleotides. J Am Soc Mass Spectrom". (Year: 2017).*

International Search Report and Written Opinion for Application No. PCT/US2018/046990 dated Dec. 13, 2018.

[No Author Listed], MEGAscript Kit Product Manual, Oct. 27, 2009. Ambion/Invitrogen website: http://lools.invitrogen.com/contenl/sfs/manuals/ cms_072987.pdf, (last accessed Mar. 17, 2013).

[No Author Listed], Oligotex Handbook, Qiagen, Jun. 2012. 104 pages. [retrieved from internet on Sep. 22, 2020]https://www.qiagen.com/au/resources/resourcedetail?id=f9fald98-d54d-47e7-a20b-8b0cb8975009&lang=en.

Andrews-Pfannkoch et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.

Azarani et al., RNA analysis by ion-pair reversed-phase high performance liquid chromatography. Nucleic Acids Res. Jan. 15, 2001;29(2):E7. doi: 10.1093/nar/29.2.e7.

Close et al., Nucleic acid separations using superficially porous silica particles. J Chromatogr A. Apr. 1, 2016;1440:135-144. doi: 10.1016/j.chroma.2016.02.057. Epub Feb. 23, 2016.

Dickman et al., Ion Pair Reverse-Phase Chromatography: A Versatile Platform for the Analysis of RNA. Chromatography Today. 2011; 22-26.

Easton et al., Rapid, nondenaturing RNA purification using weak anion-exchange fast performance liquid chromatography. RNA. Mar. 2010;16(3):647-53. Epub Jan. 25, 2010.

Georgopoulos et al., Use of high-performance liquid chromatographic fractionation of large RNA molecules in the assay of group I intron ribozyme activity. J Chromatogr A. Jan. 28, 2000;868(1):109-14.

Huber et al., Analysis of nucleic acids by on-line liquid chromatography—Mass spectrometry (Mass Spectrometry Reviews 2001, 20, pp. 310-343).

Jia et al., Kinetic mechanism of GTP binding and RNA synthesis during transcription initiation by bacteriophage T7 RNA polymerase. J Biol Chem. Nov. 28, 1997;272(48):30147-53. doi: 10.1074/jbc.272.48.30147.

Kariko et al., Generating the optimal mRNA for therapy: HPLC purification eliminates immune activation and improves translation of nucleoside-modified, protein-encoding mRNA. Nucleic Acids Res. Nov. 2011;39(21):e142.

(56) References Cited

OTHER PUBLICATIONS

Kingston, 'Preparation of poly (A)+ RNA', Current protocols in molecular biology. 1993, vol. 21, No. 1, pp. 4.51-4.5.3.

Koch et al., Quantitative Studies on the Infectivity of ribonucleic acid from partially purified and highly purified poliovirus preparations. Virology. Mar. 1960; 10(3): 329-343.

Lee et al., Separation and determination of polyethylene glycol fatty acid esters in cosmetics by a reversed-phase HPLC/ELSD. Talanta. Feb. 15, 2008;74(5):1615-20. doi: 10.1016/j.talanta.2007.10.020. Epub Oct. 18, 2007.

Lewandowski et al., Separation of the infectious ribonucleic acid of potato spindle tuber virus from double-stranded ribonucleic acid of plant tissue extracts. J Virol. Nov. 1971;8(5):809-12.

Mellits et al., Removal of double-stranded contaminants from RNA transcripts: synthesis of adenovirus VA RNAI from a T7 vector. Nucleic Acids Res. Sep. 25, 1990;18(18):5401-6.

Mignone et al., Untranslated regions of mRNAs. Genome Biol. 2002;3(3):REVIEWS0004. Epub Feb. 28, 2002. pp. 1-10.

Nwokeoji et al., Purification and characterisation of dsRNA using ion pair reverse phase chromatography and mass spectrometry. J Chromatogr A. Feb. 10, 2017;1484:14-25. doi: 10.1016/j.chroma. 2016.12.062. Epub Dec. 21, 2016.

Slater, The purification of poly(a)-containing RNA by affinity chromatography. Methods Mol Biol. 1985;2:117-20. doi: 10.1385/0-89603-064-4:117.

Wang et al., Purification of the messenger ribonucleic acid for the lipoprotein of the *Escherichia coli* outer membrane. Biochemistry. Oct. 2, 1979;18(20):4270-7.

Weissman et al., HPLC purification of in vitro transcribed long RNA. Methods Mol Biol. 2013;969:43-54. doi: 10.1007/978-1-62703-260-5_3.

Wysoczynski et al., Reversed-phase ion-pair liquid chromatography method for purification of duplex DNA with single base pair resolution. Nucleic Acids Res. Nov. 2013;41(20):e194. doi: 10.1093/nar/gkt815. Epub Sep. 5, 2013.

Yamamoto et al., Current prospects for mRNA gene delivery. Eur J Pharm Biopharm. Mar. 2009;71(3):484-9. doi: 10.1016/j.ejpb.2008. 09.016. Epub Oct. 10, 2008.

Zhang et al., Ion-pair reversed-phase chromatography of short double-stranded deoxyribonucleic acid in silicon micro-pillar array columns: retention model and applications. J Chromatogr A. Jun. 14, 2013;1294:1-9. doi: 10.1016/j.chroma.2013.04.002. Epub Apr. 8, 2013.

U.S. Appl. No. 18/055,193, filed Nov. 14, 2022, Ciaramella et al.

McCarthy et al., Ion-Pairing Systems for Reversed-Phase Chromatography Separation of Oligonucleotides. Waters Corporation. May 8, 2008. Accessed from <https://www.waters.com/webassets/cms/library/docs/720002683en.pdf> on May 31, 2023. Poster. 1 page.

U.S. Appl. No. 18/161,857, filed Jan. 30, 2023, Smith.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/830,742, filed Jun. 2, 2022, Miracco.
U.S. Appl. No. 17/852,974, filed Jun. 29, 2022, Marquardt et al.
U.S. Appl. No. 16/603,111, filed Oct. 4, 2019, Brito et al.
U.S. Appl. No. 16/483,012, filed Aug. 1, 2019, Mauger et al.
U.S. Appl. No. 18/093,119, filed Jan. 4, 2023, Mauger et al.
U.S. Appl. No. 17/350,662, filed Jun. 17, 2021, Rabideau et al.
U.S. Appl. No. 16/639,305, filed Feb. 14, 2020, Issa et al.
U.S. Appl. No. 16/623,069, filed Dec. 16, 2019, Hoge et al.
U.S. Appl. No. 18/343,344, filed Jun. 28, 2023, Hoge et al.
U.S. Appl. No. 18/349,057, filed Jul. 7, 2023, Hoge et al.
U.S. Appl. No. 16/639,403, filed Feb. 14, 2020, Hoge et al.
U.S. Appl. No. 18/318,689, filed May 16, 2023, Hoge et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/816,696, filed Aug. 1, 2022, Dousis et al.
U.S. Appl. No. 16/794,318, filed Feb. 19, 2020, Mauger et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 18/008,139, filed Dec. 2, 2022, Smith et al.
U.S. Appl. No. 17/926,353, filed Nov. 18, 2022, Brader et al.
U.S. Appl. No. 17/925,114, filed Nov. 14, 2022, White et al.
U.S. Appl. No. 17/726,971, filed Apr. 22, 2022, Hennessy.
U.S. Appl. No. 17/925,125, filed Nov. 14, 2022, White et al.
U.S. Appl. No. 18/085,457, filed Dec. 20, 2022, Joyal et al.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 17/683,171, filed Feb. 28, 2022, Ciaramella et al.
U.S. Appl. No. 15/748,773, filed Jan. 30, 2018, Ciaramella et al.
U.S. Appl. No. 17/554,182, filed Dec. 17, 2021, Ciaramella et al.
U.S. Appl. No. 15/753,293, filed Feb. 17, 2018, Smith.
U.S. Appl. No. 15/767,587, filed Apr. 11, 2018, Ciaramella.
U.S. Appl. No. 16/833,409, filed Mar. 27, 2020, Ciaramella.
U.S. Appl. No. 17/819,414, filed Aug. 12, 2022, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/583,674, filed Jan. 25, 2022, Besin et al.
U.S. Appl. No. 17/548,172, filed Dec. 10, 2021, Ciaramella et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 16/001,765, filed Jun. 6, 2018, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/482,844, filed Aug. 1, 2019, Valiante et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 17/823,255, filed Aug. 30, 2022, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/155,592, filed Jan. 22, 2021, Ciaramella et al.
U.S. Appl. No. 17/938,823, filed Oct. 7, 2022, Ciaramella et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/325,883, filed May 20, 2021, Dousis et al.
U.S. Appl. No. 17/737,581, filed May 5, 2022, Panther et al.
U.S. Appl. No. 17/615,202, filed Nov. 30, 2021, Hopson.
U.S. Appl. No. 17/641,967, filed Mar. 10, 2022, John et al.
U.S. Appl. No. 17/840,478, filed Jun. 14, 2022, Kramarczyk et al.
U.S. Appl. No. 17/796,401, filed Jul. 29, 2022, Shaw et al.
U.S. Appl. No. 17/518,542, filed Nov. 3, 2021, Metkar et al.
U.S. Appl. No. 17/796,208, filed Jul. 28, 2022, Stewart-Jones et al.
U.S. Appl. No. 17/797,784, filed Aug. 5, 2022, Stewart-Jones et al.
U.S. Appl. No. 17/572,465, filed Jan. 10, 2022, Nachbagauer et al.
PCT/US2018/046990, Dec. 13, 2018, International Search Report and Written Opinion.

\* cited by examiner

ANALYTICAL HPLC METHODS

RELATED APPLICATIONS

The present application is a national stage filing under 35 U.S.C. § 371 of international PCT application, PCT/US2018/046990, filed Aug. 17, 2018, which claims priority under 35 U.S.C. § 119(e) to U.S. provisional patent application, U.S. Ser. No. 62/547,462, filed Aug. 18, 2017, the entire contents of each of which are incorporated herein by reference.

BACKGROUND

Several methods of analyzing the purity of polynucleotides are known. For example, capillary electrophoresis (CE) is a methodology that is generally acceptable for RNAs <1500 nt (more notably <1000 nt) in length; however, CE often demonstrates reduced resolution for larger polynucleotides and impurities must be present in high abundance to be detected. Additionally, methods in the literature describing RNA analysis on CE using custom gel matrices do not have the resolution seen in High Performance Liquid Chromatography (HPLC). Gel electrophoresis alone also exhibits low resolution for long polynucleotides.

HPLC methods utilized for large polynucleotides, such as mRNAs, may also have inferior resolution. For example, multiple polyadenylated RNAs in the same mixture (e.g. a mixture of multiple RNAs each having the same polyA tail size) may be challenging to resolve or coelute. Furthermore, temperature-dependent recovery often results in loss of resolution with long constructs. On-column sample degradation is also commonly observed when HPLC methods are utilized.

SUMMARY

In some aspects, the disclosure relates to liquid chromatography (e.g., HPLC) methods which enable high resolution separations of polynucleotides of various lengths, sequences, and/or base compositions in a highly tunable manner. In some embodiments, methods described by the disclosure are novel improvements of ion-pair reversed phase (IP-RP) HPLC methods. Without wishing to be bound by any particular theory, methods described by the disclosure are useful, in some embodiments, for assessing purity and monitoring integrity of long polynucleotide preparations (e.g., RNA generated by in vitro transcription), as well as analyzing compositions containing multiple polynucleotides of discreet sizes in varying ratios within a single preparation.

In some embodiments, methods described by the disclosure use multiple ion pairs in the same mobile phase system to tune selectivity of the chromatography and optimize resolution. The disclosure is based, in part, on the discovery that combining a size-selective ion pair with a composition-selective ion pair simultaneously drives nucleic acid selectivity toward a size-based separation with varying levels of resolution, while also shifting separation bias toward base composition to attain improved resolution over each as a single component. A size-selective ion pair can be characterized as a larger, bulkier, more hydrophobic ion pairing agent such as dibutylamine or a salt (e.g., an ammonium salt) thereof (for example, dibutylammonium acetate, ("DBAA")) or hexylamine or a salt (e.g., an ammonium salt) thereof (for example hexylammonium acetate ("HAA")). A composition-selective ion pair can be characterized as a smaller, less bulky ion pairing agent with shorter alkyl chains and less overall hydrophobicity, such as trimethylamine or a salt (e.g., an ammonium salt) thereof (for example, triethylammonium acetate, ("TEAA")). Thus, in some embodiments, methods described by the disclosure are useful for high resolution analysis of long, polyadenylated polynucleotide preparations, for example pharmaceutical compositions comprising mRNA.

Accordingly, in some embodiments, the disclosure provides a method of separating a nucleic acid from a mixture comprising one or more additional nucleic acids or impurities, comprising the steps: contacting a stationary phase of a reverse phase chromatography column with the mixture; and eluting the nucleic acid with a mobile phase, wherein the mobile phase comprises one or more solvents and two or more ion pairs, such that the nucleic acid traverses the column with a retention time that is different than one or more other nucleic acids of the mixture.

In some embodiments, a column is an analytical column, or a preparative column. In some embodiments, a stationary phase comprises particles, such as porous resin particles. In some embodiments, particles are hydrophobic (e.g., comprise an intrinsically hydrophobic material such as polystyrene divinylbenzene) or comprise hydrophobic functional groups.

In some embodiments, particles have a diameter of about 2 µm to about 10 µm, about 2 µm to about 6 µm, or about 4 µm. In some embodiments, particles comprise pores having a diameter of about 100 Å to about 5000 Å, about 100 Å to about 1000 Å, or about 1000 Å to about 2000 Å.

In some embodiments, a mobile phase comprises one solvent. In some embodiments, a mobile phase is a mixture of a first solvent and a second solvent. In some embodiments, a mobile phase is a mixture of a first solvent solution and a second solvent solution.

In some embodiments, the volume percentage of a solvent solution (e.g., a first solvent solution or a second solvent solution) in a mobile phase is 0% to 100%. In some embodiments, a solvent solution (e.g., a first solvent solution or a second solvent solution) comprises one or more solvents and one or more ion pair (e.g., one or more ion pairing agent).

In some embodiments, the concentration of each of the one or more ion pair (e.g., each ion pairing agent) in a solvent solution (e.g., a first solvent solution or a second solvent solution) ranges from about 1 mM to about 2 M. In some embodiments, the concentration of each of the one or more ion pair (e.g., each ion pairing agent) in a solvent solution (e.g., a first solvent solution or a second solvent solution) ranges from about 1 mM-100 mM, 5 mM-100 mM, 5 mM-75 mM, 5 mM-50 mM, 5 mM-25 mM, 5 mM-10 mM, 10 mM-25 mM, 25 mM-50 mM, 25 mM-75 mM, 50 mM-100 mM or 75 mM-100 mM.

In some embodiments, one or more ion pair (e.g., ion pairing agent) is a cation selected from the group consisting of: trimethylamine or a salt thereof (e.g., triethylammonium salt), tetrabutylamine or a salt thereof (e.g., tetrabutylammonium salt), hexylamine or a salt thereof (e.g., hexylammonium salt), and dibutylamine or a salt thereof (e.g., dibutylammonium salt). In some embodiments, the triethylammonium salt is triethylammonium acetate (TEAA), the tetrabutylammonium salt is tetrabutylammonium phosphate (TBAP), the hexylammonium ion is hexylammonium acetate (HAA), or the dibutylammonium ion is dibutylammonium acetate (DBAA). In some embodiments, the one or more ion pairing agent is an inorganic molecule, for example unsubstituted ammonium salts ($NH_4^+$), lithium (Li), sodium (Na), potassium (K), etc., an organic cation (e.g., substituted ammonium ion), tris(hydroxymethyl)aminomethane (Tris), biological buffer (e.g., MOPS, HEPES, PIPES, etc.), or other charged or hydrophilic moiety.

In some embodiments, a solvent solution (e.g., a first solvent solution or a second solvent solution) comprises of one or more solvents selected from the group consisting of water, polar aprotic solvents (including, e.g., tetrahydrofuran (THF), dimethyl sulfoxide (DMSO), dimethylformamide (DMF), acetonitrile, acetone, etc.), $C_{1-4}$ alkanols, $C_{1-6}$ alkandiols, and $C_{2-4}$ alkanoic acids. In some embodiments, a solvent solution (e.g., a first solvent solution or a second solvent solution) comprises one or more solvents selected from the group consisting of water, acetonitrile, methanol, ethanol, isopropanol, and hexylene glycol.

In some embodiments of methods described by the disclosure, the step of eluting the nucleic acid with a mobile phase comprises the step of passing a mobile phase through the column, wherein the mobile phase is a mixture of a first solvent solution and a second solvent solution, and wherein the first solvent solution and the second solvent solution independently comprise one or more ion pair (e.g., one or more ion pairing agent) selected from the group consisting of: trimethylamine or a salt thereof (e.g., triethylammonium acetate), tetrabutylamine or a salt thereof (e.g., tetrabutylammonium acetate), hexylamine or salt thereof (e.g., hexylammonium acetate) and dibutylamine or a salt thereof (e.g., dibutylammonium acetate), such that a nucleic acid traverses the column with a retention time that is different than one or more other nucleic acids of the mixture. In some embodiments, the trimethylamine salt is triethylammonium acetate (TEAA), the tetrabutylamine salt is tetrabutylammonium phosphate (TBAP), the hexylamine salt is hexylammonium acetate (HAA), or the dibutylamine salt is dibutylammonium acetate (DBAA). In some embodiments, the one or more ion pairing agent is a non-organic molecule, for example unsubstituted ammonium, lithium (Li), sodium (Na), potassium (K), etc., an organic cation (e.g., substituted ammonium ion), tris(hydroxymethyl)aminomethane (Tris), biological buffer (e.g., MOPS, HEPES, PIPES, etc.), or other charged or hydrophilic moiety.

In some embodiments, the ratio of a first solvent solution to a second solvent solution is held constant during elution of a nucleic acid. In some embodiments, the ratio of a first solvent solution to a second solvent solution is increased or decreased during elution of the nucleic acid.

In some embodiments, the concentration of each ion pair (e.g., ion pairing agent) in a mobile phase is held constant during elution of the nucleic acid. In some embodiments, the concentration of one or more ion pair (e.g., ion pairing agent) in the mobile phase is not held constant during elution of the nucleic acid.

In some embodiments, the retention time of a nucleic acid differs from the retention time of all other nucleic acids or impurities in a mixture by 0.1-10 minutes, 0.1-5 minutes, 0.1-1 minutes, 0.1-0.5 minutes, or 0.1-0.2 minutes.

In some embodiments, a nucleic acid comprises at least 100, at least 500, at least 1000, at least 2000, at least 3000, at least 4000, at least 5000, at least 6000, at least 7000, at least 8000, or at least 9000 nucleotides.

In some embodiments, a nucleic acid is single stranded. In some embodiments, a nucleic acid is RNA or DNA. In some embodiments, a nucleic acid comprises 5' and 3' untranslated regions (UTRs). In some embodiments, a nucleic acid comprises a 5' 7-methylguanosine group (e.g., a 5' cap), or a 5' 7-methylguanosine group analog (e.g., a 5' cap analog). In some embodiments, a nucleic acid comprises a 3'-polyadenosine (polyA) tail.

In some embodiments, a mixture comprises a plurality of nucleic acids having tail length variants. In some embodiments, a mixture comprises degradation products (e.g., nucleic acid degradation products).

In some embodiments, methods described by the disclosure further comprise the step of detecting or isolating a nucleic acid, or detecting or isolating one or more additional nucleic acids or impurities from a mixture. In some embodiments, methods described by the disclosure are used to determine the potency of the mixture of nucleic acids.

In some embodiments, a nucleic acid is larger or smaller than one or more additional nucleic acids or impurities (e.g., additional nucleic acids or impurities present in a mixture), and a mobile phase comprises at least one size-selective ion pair (e.g., at least one size-selective ion paring agent).

In some embodiments, a larger nucleic acid comprises 10-100%, 25-100%, 50-100%, 50-75%, 100-200%, 200-500% or 500-1000% more nucleotides than one or more additional nucleic acids or impurities (e.g., additional nucleic acids or impurities present in a mixture).

In some embodiments, a smaller nucleic acid comprises 10-100%, 25-100%, 50-100%, 50-75%, 100-200%, 200-500% or 500-1000% fewer nucleotides than one or more additional nucleic acids or impurities (e.g., additional nucleic acids or impurities present in a mixture).

In some embodiments, a size-selective ion pair is selected from HAA, DBAA, and TBAP.

In some embodiments, a nucleic acid has a similar size as one or more additional nucleic acids or impurities (e.g., additional nucleic acids or impurities present in a mixture), and a mobile phase comprises at least one composition-selective ion pair (e.g., at least one composition-selective ion pairing agent).

In some embodiments, a nucleic acid comprises 0-10%, 0-5%, or 0-1% more or fewer nucleotides than one or more additional nucleic acids or impurities (e.g., additional nucleic acids or impurities present in a mixture).

In some embodiments, a composition-selective ion pair is TEAA.

In some embodiments, a nucleic acid and one or more additional nucleic acids (e.g., additional nucleic acids in a mixture) have lengths of less than 2000 nucleotides, wherein two or more ion pairs are triethylammonium (e.g., TEAA) and dibutylammonium (e.g., DBAA), and wherein the ratio of triethylammonium (e.g., TEAA) to dibutylammonium (e.g., DBAA) ranges from about 5:1 to about 1:5, about 3:1 to about 1:3, about 2:1 to about 1:2, or about 1:1 to 1:3.

In some embodiments of methods described by the disclosure, the eluting step is isocratic with respect to mobile phase solvent composition. In some embodiments of methods described by the disclosure, the eluting step is isocratic or gradient with respect to the concentration of one or more ion pairs (e.g., concentration of one or more ion pairing agents).

In some embodiments, a mobile phase comprises two ion pairs, and the relative concentration of the ion pairs is varied during an eluting step. In some embodiments, the eluting step is gradient with respect to mobile phase solvent composition. In some embodiments, the eluting step is isocratic or gradient with respect to the concentration of one or more ion pairs.

In some aspects, the disclosure provides a pure mRNA sample comprising: a composition of an in vitro transcribed (IVT) RNA and a pharmaceutically acceptable carrier, wherein the composition comprises a nucleic acid separated by a method as described by the disclosure.

In some aspects, the disclosure provides a method of quality control of a nucleic acid (e.g., a polyadenylated nucleic acid) pharmaceutical composition, the method comprising: separating a nucleic acid from a mixture comprising one or more additional nucleic acids or impurities by a method as described by the disclosure; comparing the separated nucleic acid with a reference nucleic acid; and determining the quality of the nucleic acid based on a comparison of the separated nucleic acid with the reference nucleic acid.

In some embodiments, the nucleic acid (e.g., polyadenylated nucleic acid) pharmaceutical composition comprises RNA, such as mRNA or in vitro transcribed (IVT) RNA.

In some embodiments, the method of quality control of a nucleic acid comprises the step of comparing a HPLC chromatogram of the separated nucleic acid with a HPLC chromatogram of the reference nucleic acid. In some embodiments, the nucleic acid separated from the mixture is RNA (e.g., mRNA, dsRNA, ssRNA, etc.), or DNA (e.g., dsDNA, ssDNA, etc.). In some embodiments, the method further comprises comparing the nucleic acid separated from the mixture with a reference nucleic acid using an analytical method, for example polymerase chain reaction (e.g., qRT-PCR), nucleic acid sequencing, gel electrophoresis, restriction digest-based analysis, mass spectrometry, etc.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

FIG. 2A shows representative chromatograms from mixed ion pairing systems (HAA/TEAA on top; DBAA/TEAA on bottom). FIG. 2B shows representative data demonstrating introduction of low concentrations of a bulkier ion pair (e.g., HAA) to a 100 mM TEAA ion pairing system results in altered resolution of multiple species within a complex mixture. Increasing concentrations of HAA in 100 mM TEAA shift mRNAs of different sizes (e.g., T100 GFP and T60/100 Luc) apart, and resolution is lost between the tail variants of Luc.

FIGS. 6A and 6B show a comparison of linear separation methods (FIG. 6A) with constant organic phase (ACN):ion pair gradient elution (FIG. 6B) for complex mixtures of mRNA. FIG. 6C shows representative chromatograms comparing HPLC solid phase (e.g., PLRP column vs. DNA-Pac™ RP Column (High Performance Reversed-Phase LC Column)) performance in methods described by the disclosure FIG. 6D shows representative chromatograms for quaternary ion pair (IP)/organic gradients as described by the disclosure. Briefly, the concentrations of TEAA and DBAA are individually controlled, to tune the separation in each region of the elution gradient. Each chromatogram was produced using a "reversed" gradient for reversed phase, with decreasing acetonitrile through the elution region to allow a wide range of compositions, and also includes the use of high DBAA concentration to separate the shorter species; increasing TEAA to is used to resolve mRNAs greater than 2 kb.

DETAILED DESCRIPTION

Figure 1A:
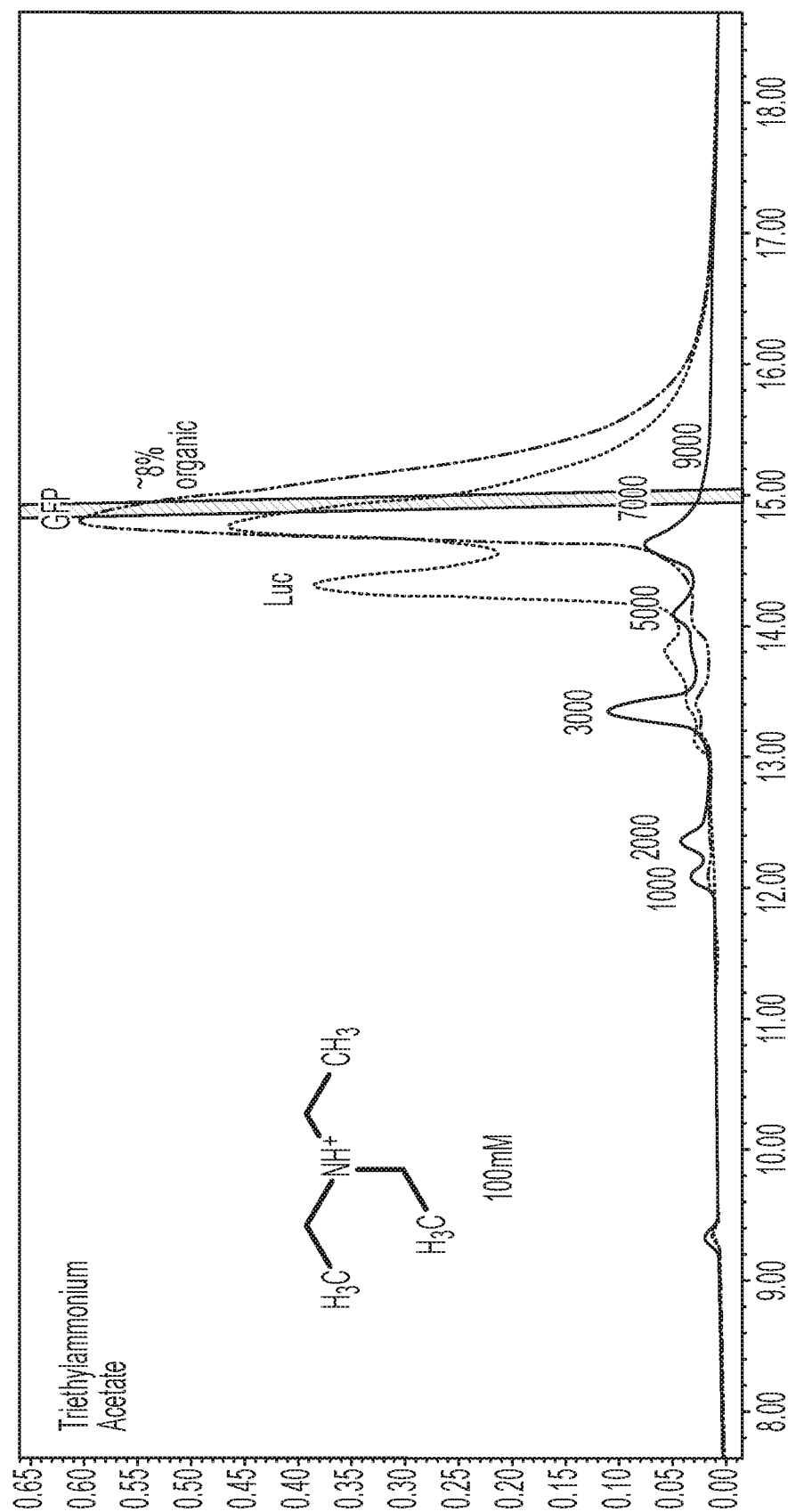
FIGS. 1A-1D show representative HPLC chromatograms comparing three alkylammonium ion pairing agents (HAA in FIG. 1B; TBAP in FIG. 1C; DBAA in FIG. 1D) to the standard ion pairing agent for RNA and DNA separations, triethylammonium acetate (TEAA, FIG. 1A). The samples tested were commercially available tailless ladders (50-1000 nt and 500-9000 nt) and three polyadenylated mRNAs (ORFan ~200 nt, GFP is ~900 nt, Luc is ~2000 nt and comprises a mixture of Luc 60 A and Luc 100 A tail length variants). A PLRP-S 4000 Å 8 μm (Agilent Technologies) column was used for this experiment.

In some aspects, the disclosure relates to high performance liquid chromatography methods (e.g., HPLC methods) for analyzing polynucleotides (e.g., mixtures containing polynucleotides, such as RNA molecules). Typically, an HPLC apparatus comprises a reservoir containing a mobile phase, a sample input port, a chromatography column containing the stationary phase, and a detection apparatus. HPLC apparatus and methods for HPLC detection of RNA molecules are generally described, for example in U.S. Pat. No. 8,383,340, the entire contents of which are incorporated herein by reference.

In some aspects, the disclosure relates to reversed phase ion pairing HPLC (RP-IP HPLC). Generally, RP-IP HPLC refers to a liquid chromatographic methodology in which retention of analytes on an HPLC column is modulated by addition of an ion pairing agent that alters electrostatic interactions between analytes in a sample (e.g., nucleic acids) and the stationary phase of the chromatography column. Without wishing to be bound by any particular theory, a single ion pairing agent is typically used. Larger, bulkier, more hydrophobic ion pairing agents with higher degree of alkylation are believed to drive selectivity toward a size-based separation, with varying levels of resolution. Smaller, less bulky ion pairing agents with shorter alkyl chains and less overall hydrophobicity are believed to shift bias toward base composition. In the context of HPLC analysis of certain polyadenylated molecules (e.g., mRNA), the polyA tail acts as a hydrophobic tag and biases selectivity, causing a loss of resolution between multiple RNAs of considerably different sizes depending on the ion pairing agent in use. Conversely, resolution between two RNAs of similar size may not be adequate using only a single highly alkylated bulky ion pair.

The disclosure is based, in part, on the discovery that inclusion of certain combinations of ion pairing agents (e.g., the combination of a size-selective ion pairing agent and a composition-selective ion pairing agent as described by the disclosure) during HPLC of samples containing polynucleotides results in improved resolution and detection of impurities in the samples. The addition of a less bulky ion pairing agent (e.g., a composition-selective ion pairing agent), in some embodiments, addresses the loss of resolution with increasing length, enhancing the size-based separation of polynucleotides greater than 2.5 kb compared to single-ion pair systems. Resolution has been further improved through the novel elution strategy of an ion pair gradient, where the ion pairing agent ratio is manipulated at increasing, constant, or decreasing organic composition to provide high resolution separations. The combination of both classes of ion pairing agents in a single system enhances selectivity based on polynucleotide size and composition where the concentrations and ratios of the ion pairs to each other can be tuned to maximize resolution in specific applications. Therefore, due to the exceptional resolution that can be achieved, this is a preferred means of assessing purity of certain molecules (e.g., mRNAs, such as therapeutically relevant RNAs from 100-5000 nt and larger) compared to methods previously described in the art.

Accordingly, in some aspects, the disclosure provides a method of separating a nucleic acid from a mixture comprising one or more additional nucleic acids or impurities, comprising the steps: contacting a stationary phase of a reverse phase chromatography column with the mixture; and eluting the nucleic acid with a mobile phase, wherein the mobile phase comprises one or more solvents and two or more ion pairs, such that the nucleic acid traverses the column with a retention time that is different than one or more other nucleic acids of the mixture.

As used herein, an "ion pairing agent" or an "ion pair" refers to an agent (e.g., a small molecule) that functions as a counter ion to a charged (e.g., ionized or ionizable) functional group on an HPLC analyte (e.g., a nucleic acid) and thereby changes the retention time of the analyte as it moves through the stationary phase of an HPLC column. Generally, ion paring agents are classified as cationic ion pairing agents (which interact with negatively charged functional groups) or anionic ion pairing agents (which interact with positively charged functional groups). The terms "ion pairing agent" and "ion pair" further encompass an associated counter-ion (e.g., acetate, phosphate, bicarbonate, chloride, citrate, nitrate, nitrite, oxide, sulfate and the like, for cationic ion pairing agents, and sodium, calcium, and the like, for anionic ion pairing agents). In some embodiments, one or more ion pairing agents utilized in the methods described by the disclosure is a cationic ion pairing agent. Examples of cationic ion pairing agents include but are not limited to certain protonated or quaternary amines (including e.g., primary, secondary and tertiary amines) and salts thereof, such as triethylammonium acetate (TEAA), tetrabutylammonium phosphate (TBAP), hexylammonium acetate (HAA) and dibutylammonium acetate (DBAA).

Protonated and quaternary amine ion pairing agents can be represented by the following formula:

wherein each R independently is hydrogen, optionally substituted aliphatic, optionally substituted heteroaliphatic, optionally substituted aryl or optionally substituted heteroaryl; provided that at least one instance of R is not hydrogen; and A is an anionic counter ion.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups. The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). Suitable anionic counter ions include, but are not limited to, acetate, trifluoroacetate, phosphate, hexafluorophosphate, sulfate, methylsulfonate, trifluoromethylsulfonate, 1,1,1,3,3,3-hexafluoro-2-propanol (HFIP), 1,1,1,3,3,3-hexafluoro-2-methyl-2-propanol (HFMIP) and the like.

The term "optionally substituted" refers to being substituted or unsubstituted. In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction.

In some embodiments, ion pairing agents are classified as a "size-selective" ion pairing agent or a "composition-selective" ion pairing agent. Without wishing to be bound by any particular theory, in a particular embodiment, a "size-selective" ion pairing agent is capable of promoting separation of an individual analyte (e.g., RNA) from impurities or from a mixture of analytes on the basis of size. Similarly, in a particular embodiment, a "composition-selective" ion pairing agent is capable of promoting separation of an individual analyte (e.g., RNA) from impurities or from a mixture of analytes on the basis of composition (e.g., base composition). In one embodiment, a size-selective ion pairing agent comprises four or more (e.g., 4, 5, 6, 7, 8, 9, 10, or more) carbon molecules per alkyl chain. In another particular embodiment, a "composition-selective" ion pairing agent typically comprises three or less (e.g., 3, 2, or 1) carbon molecules per alkyl chain. In some embodiments, a size-selective ion pairing agent is selected from the group consisting of tetrabutylamine salts, for example tetrabutylammonium phosphate (TBAP), hexylamine salts, for example hexylammonium acetate (HAA) and dibutylamine salts, for example dibutylammonium acetate (DBAA). In some embodiments, a composition-selective ion pairing agent is triethylammonium acetate (TEAA).

Ion pairing agents are generally dispersed within a mobile phase. As used herein, a "mobile phase" is an aqueous solution comprising water and/or one or more organic solvents used to carry an HPLC analyte (or analytes), such as a nucleic acid or mixture of nucleic acids through an HPLC column. Generally, a IP-RP HPLC mobile phase comprises a polar organic solvent. Examples of polar organic solvents suitable for inclusion in a mobile phase include but are not limited to alcohols, ketones, nitrates, esters, amides and alkylsulfoxides. In some embodiments, a mobile phase comprises one or more organic solvents selected from the group consisting of acetonitrile, methanol, ethanol, propanol, isopropanol, dimethylformamide, methyl acetate, acetone, and dimethylsulfoxide (DMSO), hexylene glycol, polar aprotic solvents, $C_{1-4}$ alkanols, $C_{1-6}$ alkandiols, and $C_{2-4}$ alkanoic acids. In some embodiments, a mobile phase comprises acetonitrile. In some embodiments, a mobile phase comprises additional components, for example as described in U.S. Patent Publication US 2005/0011836, the entire contents of which are incorporated herein by reference.

The concentration of organic solvent in a mobile phase can vary. For example, in some embodiments, the volume percentage (v/v) of an organic solvent in a mobile phase varies from 0% (absent) to about 100% of a mobile phase. In some embodiments, the volume percentage of organic solvent in a mobile phase is between about 5% and about 75% v/v. In some embodiments, the volume percentage of organic solvent in a mobile phase is between about 25% and about 60% v/v. In some embodiments, the concentration of organic solvent in a mobile phase is about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% v/v.

The pH of the mobile phase (e.g., the pH of each solvent solution of the mobile phase) can vary. In some embodiments, the pH of the mobile phase is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the mobile phase is between about pH 6.8 and pH 8.5 (e.g., about 6.8, about 7.0, about 7.2, about 7.4, about 7.6, about 7.8, about 8.0, about 8.3, or about 8.5). In some embodiments, the pH of the mobile phase is about 7.0.

In some embodiments, the pH of the first solvent solution is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the first solvent solution is between about pH 6.8 and pH 8.5 (e.g., about 6.8, about 7.0, about 7.2, about 7.4, about 7.6, about 7.8, about 8.0, about 8.3, or about 8.5). In some embodiments, the pH of the first solvent solution is about 7.0.

In some embodiments, the pH of the second solvent solution is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the second solvent solution is between about pH 6.8 and pH 8.5 (e.g., about 6.8, about 7.0, about 7.2, about 7.4, about 7.6, about 7.8, about 8.0, about 8.3, or about 8.5). In some embodiments, the pH of the second solvent solution is about 7.0.

In some embodiments, a mobile phase for use in HPLC methods as described by the disclosure is comprised of multiple (e.g., 2, 3, 4, 5, or more) solvent solutions. In some embodiments of HPLC methods described by the disclosure, the mobile phase comprises two solvent solutions (e.g., Mobile Phase A, and Mobile Phase B). In some embodiments, a solvent solution comprises one or more organic solvent (e.g., polar solvent, such as acetonitrile) and one or more ion pairing agents.

The concentration of two or more solvent solutions in a mobile phase can vary. For example, in a mobile phase comprising two solvent solutions (e.g., a first solvent solution and a second solvent solution), the volume percentage of the first solvent solution may range from about 0% (absent) to about 100%. In some embodiments, the volume percentage of the first solvent solution may range from about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% v/v.

Conversely, in some embodiments, the volume percentage of the second solvent solution of a mobile phase may range from about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% v/v.

The concentration of one or more ion pairing agents in a mobile phase (e.g., a solvent solution) can vary. For example, in some embodiments, the concentration of each of the one or more ion pair (e.g., each ion pairing agent) in a solvent solution (e.g., a first solvent solution or a second solvent solution) ranges from about 1 mM to about 2 M (e.g., about 1 mM, about 2 mM, about 5 mM, about 10 mM, about 50 mM, about 100 mM, about 200 mM, about 500 mM, about 1 M, about 1.2 M, about 1.5 M, or about 2M), inclusive. In some embodiments, the concentration of an ion pairing agent in a mobile phase (e.g., solvent solution) ranges from about 1 mM-100 mM, 5 mM-100 mM, 5 mM-75 mM, 5 mM-50 mM, 5 mM-25 mM, 5 mM-10 mM, 10 mM-25 mM, 25 mM-50 mM, 25 mM-75 mM, 50 mM-100 mM or 75 mM-100 nM. Examples of ion pairing agent concentrations include but are not limited to 5 mM DBAA/100 mM TEAA, 15 mM DBAA/100 mM TEAA, 75 mM DBAA/25 mM TEAA, 75 mM DBAA/50 mM TEAA, 50 mM DBAA/50 mM TEAA, and 50 mM DBAA/100 mM TEAA.

In some aspects, the disclosure relates to the discovery that ion pair gradients, where the ratio of certain combinations of ion pairing agents (e.g., a size-selective ion pairing agent and a composition-selective ion pairing agent) is manipulated at increasing, constant, or decreasing organic composition, allow for high resolution separations of polyadenylated nucleic acids (e.g., mRNAs, such as IVT mRNAs). Accordingly, some embodiments of HPLC methods described by the disclosure comprise the step of passing a mobile phase through the column, wherein the mobile phase is a mixture of a first solvent solution and a second solvent solution, and wherein the first solvent solution and the second solvent solution independently comprise one or more ion pair selected from the group consisting of: trimethylamine or a salt thereof (e.g., triethylammonium salt), tetrabutylamine or a salt thereof (e.g., tetrabutylammonium salt), hexylamine or a salt thereof (e.g., hexylammonium salt) and dibutylamine or a salt thereof (e.g., dibutylammonium salt), optionally wherein the triethylammonium salt is triethylammonium acetate (TEAA), the tetrabutylammonium salt is tetrabutylammonium phosphate (TBAP), the hexylammonium salt is hexylammonium acetate (HAA), or the dibutylammonium salt is dibutylammonium acetate (DBAA), such that the nucleic acid traverses the column with a retention time that is different than one or more other nucleic acids of the mixture.

In some embodiments, the ratio of the first solvent solution to the second solvent solution is held constant (e.g., isocratic) during elution of the nucleic acid. However, the skilled artisan will appreciate that in other embodiments, the relative ratio of the first solvent solution to the second solvent solution can vary throughout the elution step. For example, in some embodiments, the ratio of the first solvent solution is increased relative to the second solvent solution during the elution step. In some embodiments, the ratio of the first solvent solution is decreased relative to the second solvent solution during the elution step.

The relative ratios of the one or more ion pairing agent in a mobile phase (or solvent solution) may vary or be held constant (e.g., isocratic) during the eluting step. In some embodiments, the ratio of a first ion pairing agent is increased relative to a second ion pairing agent during the elution step. In some embodiments, the ratio of a first ion pairing agent is increased relative to a second ion pairing agent during the elution step. For example, in some embodiments, the ratio of triethylammonium (e.g., TEAA) to dibutylammonium (e.g., DBAA) ranges from about 1:100 to about 100:1, about 1:75 to about 75:1, about 1:50 to about 50:1, about 1:25 to about 25:1, 5:1 to about 1:5, about 3:1 to about 1:3, about 2:1 to about 1:2, or about 1:1 to 1:3.

Any suitable HPLC column (e.g., stationary phase) may be used in the methods described by the disclosure. Generally, a "HPLC column" is a solid structure or support that contains a medium (e.g. a stationary phase) through which the mobile phase and HPLC sample (e.g., a sample containing HPLC analytes, such as nucleic acids) is eluted. Without wishing to be bound by any particular theory, the composition and chemical properties of the stationary phase determine the retention time of HPLC analytes. In some embodiments of HPLC methods described by the disclosure, the stationary phase is non-polar. Examples of non-polar stationary phases include but are not limited to resin, silica (e.g., alkylated and non-alkylated silica), polystyrenes (e.g., alkylated and non-alkylated polystyrenes), polystyrene divinylbenzenes, etc. In some embodiments, a stationary phase comprises particles, for example porous particles. In some embodiments, a stationary phase (e.g., particles of a stationary phase) is hydrophobic (e.g., made of an intrinsically hydrophobic material, such as polystyrene divinylbenzene), or comprise hydrophobic functional groups. In some embodiments, a stationary phase is a membrane or monolithic stationary phase.

The particle size (e.g., as measured by the diameter of the particle) of an HPLC stationary phase can vary. In some embodiments, the particle size of a HPLC stationary phase ranges from about 1 μm to about 100 μm (e.g., any value between 1 and 100, inclusive) in diameter. In some embodiments, the particle size of a HPLC stationary phase ranges from about 2 μm to about 10 μm, about 2 μm to about 6 μm, or about 4 μm in diameter. The pore size of particles (e.g., as measured by the diameter of the pore) can also vary. In some embodiments, the particles comprise pores having a diameter of about 100 Å to about 10,000 Å. In some embodiments, the particles comprise pores having a diameter of about 100 Å to about 5000 Å, about 100 Å to about 1000 Å, or about 1000 Å to about 2000 Å. In some embodiments, the stationary phase comprises polystyrene divinylbenzene, for example as used in PLRP-S 4000 columns or DNAPac™ RP Columns (High Performance Reversed-Phase LC Columns).

The temperature of the column (e.g., the stationary phase within the column) can vary. In some embodiments, the column has a temperature from about 20° C. to about 99° C. (e.g., any temperature between 20° C. and 99° C. In some embodiments, the column has a temperature from about 40° C. to about 99° C. (e.g., any temperature between 40° C. and 99° C., for example about 40° C., about 50° C., about 60° C., about 70° C., about 80° C., about 90° C., about 95° C., or about 99° C.). In some embodiments, the column has a temperature from about 60° C. to about 90° C. (e.g., any temperature between 60° C. and 90° C.). In some embodiments, the column has a temperature of about 65° C.

In some embodiments, HPLC methods as described by the disclosure comprise the step of detecting or isolating a nucleic acid. Any detection apparatus or modality suitable for HPLC may be used. Examples of HPLC detectors include but are not limited to absorbance detectors (e.g., UV/VIS detectors), fluorescence detectors, electrochemical detectors, and mass spectrometric detectors.

In some aspects, the disclosure relates to improved HPLC methods for detection of nucleic acids. As used herein, a "polynucleotide" or "nucleic acid" is at least two nucleotides covalently linked together, and in some instances, may contain phosphodiester bonds (e.g., a phosphodiester "backbone") or modified bonds, such as phosphorothioate bonds. An "engineered nucleic acid" is a nucleic acid that does not occur in nature. In some instances the nucleic acid is an engineered nucleic acid. It should be understood, however, that while an engineered nucleic acid as a whole is not naturally-occurring, it may include nucleotide sequences that occur in nature. Thus, a "polynucleotide" or "nucleic acid" sequence is a series of nucleotide bases (also called "nucleotides"), generally in DNA and RNA, and means any chain of two or more nucleotides. The terms include genomic DNA, cDNA, RNA, any synthetic and genetically manipulated polynucleotides. This includes single- and double-stranded molecules; i.e., DNA-DNA, DNA-RNA, and RNA-RNA hybrids as well as "protein nucleic acids" (PNA) formed by conjugating bases to an amino acid backbone.

The methods of the invention involve the analysis of samples (e.g., mixtures) comprising one or more nucleic acids, for example DNA or RNA. An RNA typically is composed of repeating ribonucleosides. It is possible that the RNA includes one or more deoxyribonucleosides. In preferred embodiments the RNA is comprised of greater than 60%, 70%, 80% or 90% of ribonucleosides. In other embodiments the RNA is 100% comprised of ribonucleosides. The RNA in a mixture is preferably an mRNA.

As used herein, the term "messenger RNA (mRNA)" refers to a ribonucleic acid that has been transcribed from a DNA sequence by an RNA polymerase enzyme, and interacts with a ribosome to synthesize protein encoded by DNA. Generally, mRNA are classified into two sub-classes: pre-mRNA and mature mRNA. Precursor mRNA (pre-mRNA) is mRNA that has been transcribed by RNA polymerase but has not undergone any post-transcriptional processing (e.g., 5'capping, splicing, editing, and polyadenylation). Mature mRNA has been modified via post-transcriptional processing (e.g., spliced to remove introns and polyadenylated region) and is capable of interacting with ribosomes to perform protein synthesis. mRNA can be isolated from tissues or cells by a variety of methods. For example, a total RNA extraction can be performed on cells or a cell lysate and the resulting extracted total RNA can be purified (e.g., on a column comprising oligo-dT beads) to obtain extracted mRNA.

Alternatively, mRNA can be synthesized in a cell-free environment, for example by in vitro transcription (IVT). IVT is a process that permits template-directed synthesis of ribonucleic acid (RNA) (e.g., messenger RNA (mRNA)). It is based, generally, on the engineering of a template that includes a bacteriophage promoter sequence upstream of the sequence of interest, followed by transcription using a corresponding RNA polymerase. In vitro mRNA transcripts, for example, may be used as therapeutics in vivo to direct ribosomes to express protein therapeutics within targeted tissues.

Traditionally, the basic components of an mRNA molecule include at least a coding region, a 5'UTR, a 3'UTR, a 5' cap and a poly-A tail. IVT mRNA may function as mRNA but are distinguished from wild-type mRNA in their functional and/or structural design features which serve to overcome existing problems of effective polypeptide production using nucleic-acid based therapeutics. For example, IVT mRNA may be structurally modified or chemically modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCCG". Here, the dinucleotide "CC" has been inserted, resulting in a structural modification to the polynucleotide.

A nucleic acid molecule (e.g., DNA or RNA) may comprise naturally occurring nucleotides and/or non-naturally occurring nucleotides such as modified nucleotides. In some embodiments, one or more nucleotides of a polynucleotide includes at least one chemical modification. In some embodiments, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine. Other exemplary chemical modifications useful in the mRNA described herein include those listed in US Published patent application 2015/0064235.

An "in vitro transcription template (IVT)," as used herein, refers to deoxyribonucleic acid (DNA) suitable for use in an IVT reaction for the production of messenger RNA (mRNA). In some embodiments, an IVT template encodes a 5' untranslated region, contains an open reading frame, and encodes a 3' untranslated region and a polyA tail. The particular nucleotide sequence composition and length of an IVT template will depend on the mRNA of interest encoded by the template.

A "5' untranslated region (UTR)" refers to a region of an mRNA that is directly upstream (i.e., 5') from the start codon (i.e., the first codon of an mRNA transcript translated by a ribosome) that does not encode a protein or peptide. In some embodiments, a 5' UTR encodes a 7-methylguanosine cap or a 7-methylguanosine group analog (e.g., a cap analog for example as described by Kowalska et al. RNA. 2008 June; 14(6): 1119-1131).

A "3' untranslated region (UTR)" refers to a region of an mRNA that is directly downstream (i.e., 3') from the stop codon (i.e., the codon of an mRNA transcript that signals a termination of translation) that does not encode a protein or peptide.

An "open reading frame" is a continuous stretch of DNA beginning with a start codon (e.g., methionine (ATG)), and ending with a stop codon (e.g., TAA, TAG or TGA) and encodes a protein or peptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In some embodiments, a polyA tail contains up to 1000 adenosine monophosphates. In a relevant biological setting (e.g., in cells, in vivo, etc.) the poly(A) tail functions to protect mRNA from enzymatic degradation, e.g., in the cytoplasm, and aids in transcription termination, export of the mRNA from the nucleus, and translation.

In some embodiments, a mixture of nucleic acids comprises polyA tail length variants. As used herein, a "tail length variant" refers to a polynucleotide having an identical protein coding sequence to a full-length polynucleotide but having a polyA tail of a different length. For example, if a full length polynucleotide encoding GFP comprises a polyA tail that is 100 nucleotides in length, a GFP tail length variant may have an identical coding sequence but comprise a polyA tail that is 60 nucleotides in length. Generally, tail length variants comprise a polyA tail that is shorter than a full length polynucleotide. In some embodiments, a polyA tail variant has a polyA tail that is between about 1 and about 200 nucleotides (e.g., any integer between 1 and 200) shorter than a wild-type polynucleotide. In some embodiments, a polyA tail variant has a polyA tail that is more than 200 nucleotides shorter than a wild-type polynucleotide.

In some aspects, the disclosure relates to the discovery that HPLC methods using combinations of ion pairing agents enhance identification and separation of large polynucleotides. Thus, in some embodiments of methods described by the disclosure, a nucleic acid (e.g., a nucleic acid separated from a mixture) is larger than 100 nucleotides in length. In some embodiments, a nucleic acid (e.g., a nucleic acid separated from a mixture) is between about 100 and about 10000 nucleotides in length, about 200 and about 7500 nucleotides in length, or about 500 and about 5000 nucleotides in length.

In some embodiments, an mRNA (e.g., IVT mRNA) is a therapeutic and/or prophylactic mRNA. As used herein, the term "therapeutic mRNA" refers to an mRNA molecule (e.g., an IVT mRNA) that encodes a therapeutic protein. Therapeutic proteins mediate a variety of effects in a host cell or a subject in order to treat a disease or ameliorate the signs and symptoms of a disease. For example, a therapeutic protein can replace a protein that is deficient or abnormal, augment the function of an endogenous protein, provide a novel function to a cell (e.g., inhibit or activate an endogenous cellular activity, or act as a delivery agent for another therapeutic compound (e.g., an antibody-drug conjugate). As used herein, the term "prophylactic mRNA" refers to an mRNA molecule (e.g., an IVT mRNA) that encodes a prophylactic protein such as a vaccine antigen. Prophylactic proteins mediate a variety of effects in a host cell or a subject in order to prevent disease. Therapeutic and/or prophylactic mRNA may be useful for the treatment of the following diseases and conditions: bacterial infections, viral infections, parasitic infections, cell proliferation disorders, genetic disorders, and autoimmune disorders.

In some aspects, the disclosure provides HPLC methods for separating a nucleic acid from a mixture comprising one or more additional nucleic acids or impurities. A mixture may comprise between about 1 and about 100 nucleic acids. As used herein, the term "impurity" refers to a small molecule, protein, virus, bacterium, etc., that contaminates a composition comprising a desired nucleic acid (e.g., the nucleic acid sought to be separated from the mixture).

A nucleic acid may be larger or smaller than the one or more other nucleic acids or impurities in a mixture. For example, a larger nucleic acid may comprise about 10-100%, 25-100%, 50-100%, 50-75%, 100-200%, 200-500% or 500-1000% more nucleotides than the one or more additional nucleic acids or impurities in a mixture. Alternatively, a smaller nucleic acid may comprise about 10-100%, 25-100%, 50-100%, 50-75%, 100-200%, 200-500% or 500-1000% fewer nucleotides than the one or more additional nucleic acids or impurities in a mixture. In some embodiments, an impurity is a degradation product, for example a fragment (e.g., polynucleotide) that has been cleaved from a nucleic acid (e.g., an mRNA).

In some embodiments, HPLC methods as described by the disclosure are capable of separating nucleic acids that are closely related in size. For example, in some embodiments, HPLC methods as described by the disclosure are capable of separating nucleic acids that differ in size by about 1-2 nucleotides for a 100-mer polynucleotide, about 20 nucleotides for a 1000-mer polynucleotide, about 40 nucleotides for a 2000-mer polynucleotide, or about 100 nucleotides for a 5000-mer polynucleotide. in some embodiments, HPLC methods as described by the disclosure are capable of separating nucleic acids that differ in size by about 1-2 nucleotides for a 10,000-mer polynucleotide.

In some embodiments, HPLC methods as described by the disclosure are capable of separating nucleic acids that are closely related in molecular weight (e.g., as expressed in Daltons (Da)). For example, in some embodiments, HPLC methods as described by the disclosure are capable of separating nucleic acids that differ in molecular weight by about 680 Da to about 34,000 Da, about 1000 Da to about 20,000 Da, or about 5000 Da to about 10,000 Da.

Delivery of mRNA molecules to a subject in a therapeutic context is promising because it enables intracellular translation of the mRNA and production of at least one encoded peptide or polypeptide of interest without the need for nucleic acid-based delivery systems (e.g., viral vectors and DNA-based plasmids). Therapeutic mRNA molecules are generally synthesized in a laboratory (e.g., by in vitro transcription). However, there is a potential risk of carrying over impurities or contaminants, such as incorrectly synthesized mRNA and/or undesirable synthesis reagents, into the final therapeutic preparation during the production process. In order to prevent the administration of impure or contaminated mRNA, the mRNA molecules can be subject to a quality control (QC) procedure (e.g., validated or identified) prior to use. Validation confirms that the correct mRNA molecule has been synthesized and is pure.

Certain aspects of the disclosure relate to the discovery that HPLC methods described herein are useful, in some embodiments, for quality control of certain nucleic acid molecules (e.g., polyadenylated nucleic acids, such as mRNA).

Accordingly, in some aspects, the disclosure provides a method of quality control of a nucleic acid (e.g., a polyadenylated nucleic acid) pharmaceutical composition, the method comprising: separating a nucleic acid (e.g., a polyadenylated nucleic acid) from a mixture comprising one or more additional nucleic acids or impurities by a method as described by the disclosure; comparing the separated nucleic acid with a reference nucleic acid (e.g., a reference polyadenylated nucleic acid); and determining the quality of the nucleic acid based on a comparison of the separated nucleic acid with the reference nucleic acid.

In some instances, the methods of the disclosure are used to determine the purity of an RNA sample. The term "pure" as used herein refers to material that has only the target nucleic acid active agents such that the presence of unrelated nucleic acids is reduced or eliminated, i.e., impurities or contaminants, including RNA fragments. For example, a purified RNA sample includes one or more target or test nucleic acids but is preferably substantially free of other nucleic acids. As used herein, the term "substantially free" is used operationally, in the context of analytical testing of the material. Preferably, purified material substantially free of impurities or contaminants is at least 95% pure; more preferably, at least 98% pure, and more preferably still at least 99% pure. In some embodiments a pure RNA sample is comprised of 100% of the target or test RNAs and includes no other RNA. In some embodiments it only includes a single type of target or test RNA.

A "reference nucleic acid" as used herein refers to a control nucleic acid (e.g. a polyadenylated nucleic acid, such as mRNA) or chromatogram generated from a control nucleic acid that uniquely identifies the nucleic acid separated from the mixture. The reference nucleic acid may be generated based on digestion of a pure sample and compared to data generated by HPLC of a mixture comprising the nucleic acid of interest. Alternatively it may be a known chromatogram, stored in a electronic or non-electronic data medium. For example, a control chromatogram may be a chromatogram based on predicted HPLC retention times of a particular RNA (e.g., a test mRNA). In some embodiments quality control methods described by the disclosure further comprise the step of comparing the nucleic acid separated from the mixture to the reference nucleic acid using an orthogonal analytical technique, for example polymerase chain reaction (e.g., RT-qPCR), nucleic acid sequencing, gel electrophoresis, mass spectrometry, etc.

For the purposes of the invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

EXAMPLES

Example 1

HPLC-based separation of mRNA was compared between three alkylammonium ion pairing agents (Hexylammonium acetate (HAA), Tetrabutylammonium phosphate (TBAP) and Dibutylammonium acetate (DBAA)) and triethylammonium acetate (TEAA, top left). The samples tested were commercially available tailless ladders (50-1000 nt and 500-9000 nt) and three polyadenylated mRNAs (ORFan is ~200 nt, GFP is ~900 nt, Luc is ~2000 nt and comprises a mixture of A60 and A100 tail length variants). Representative chromatograms are shown in FIGS. 1A-1D.

In the standard TEAA method, an adequate separation is obtained for the tailless commercial ladder, but the polyadenylated mRNA species coelute regardless of length (FIG. 1A). It was observed that polyadenylated mRNA also elute well past the elution point of the longest tailless species due to the hydrophobicity of the polyA tail; the shortened tail in the Luc sample has an exaggerated effect.

Figure 1B:
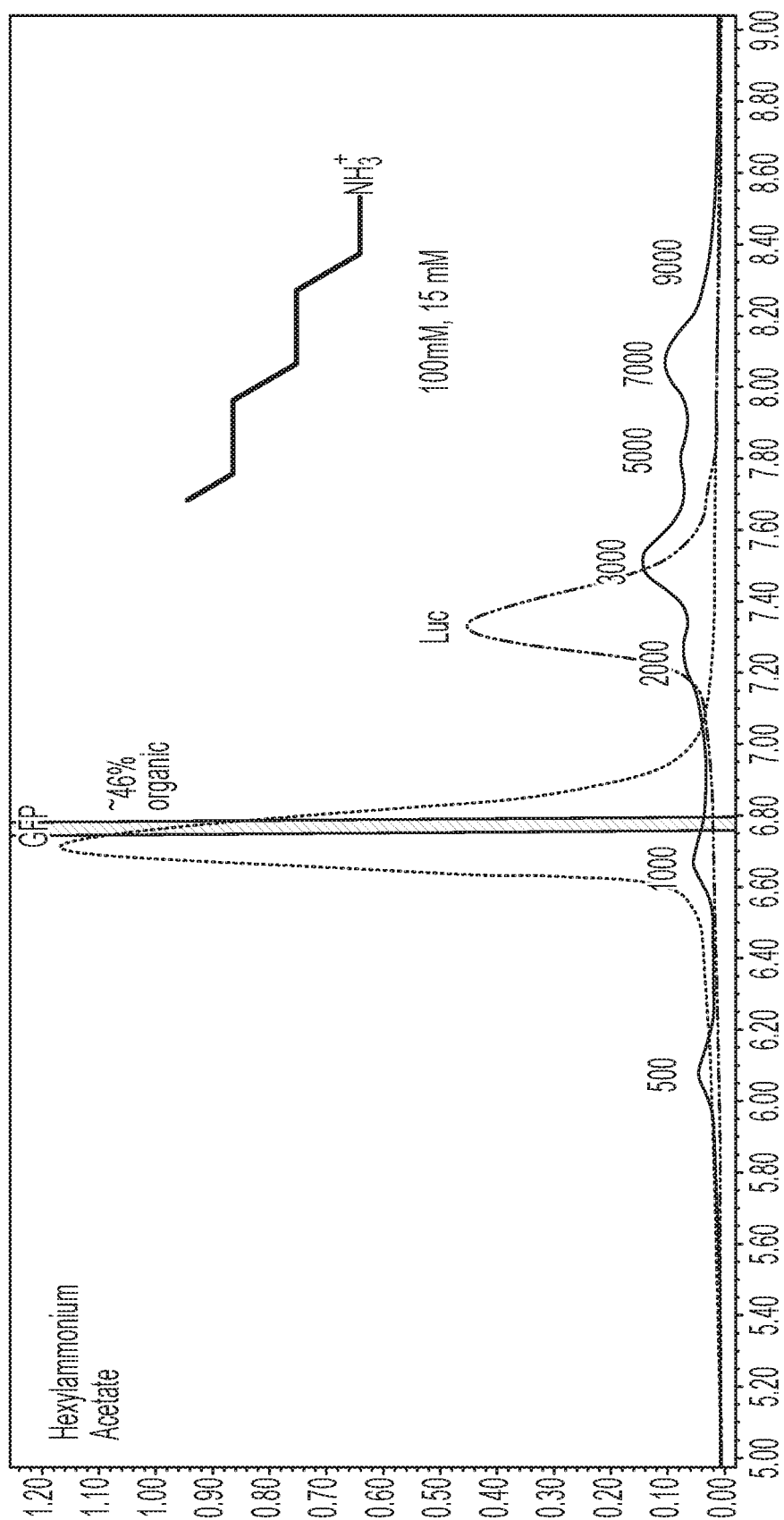
Figure 1C:
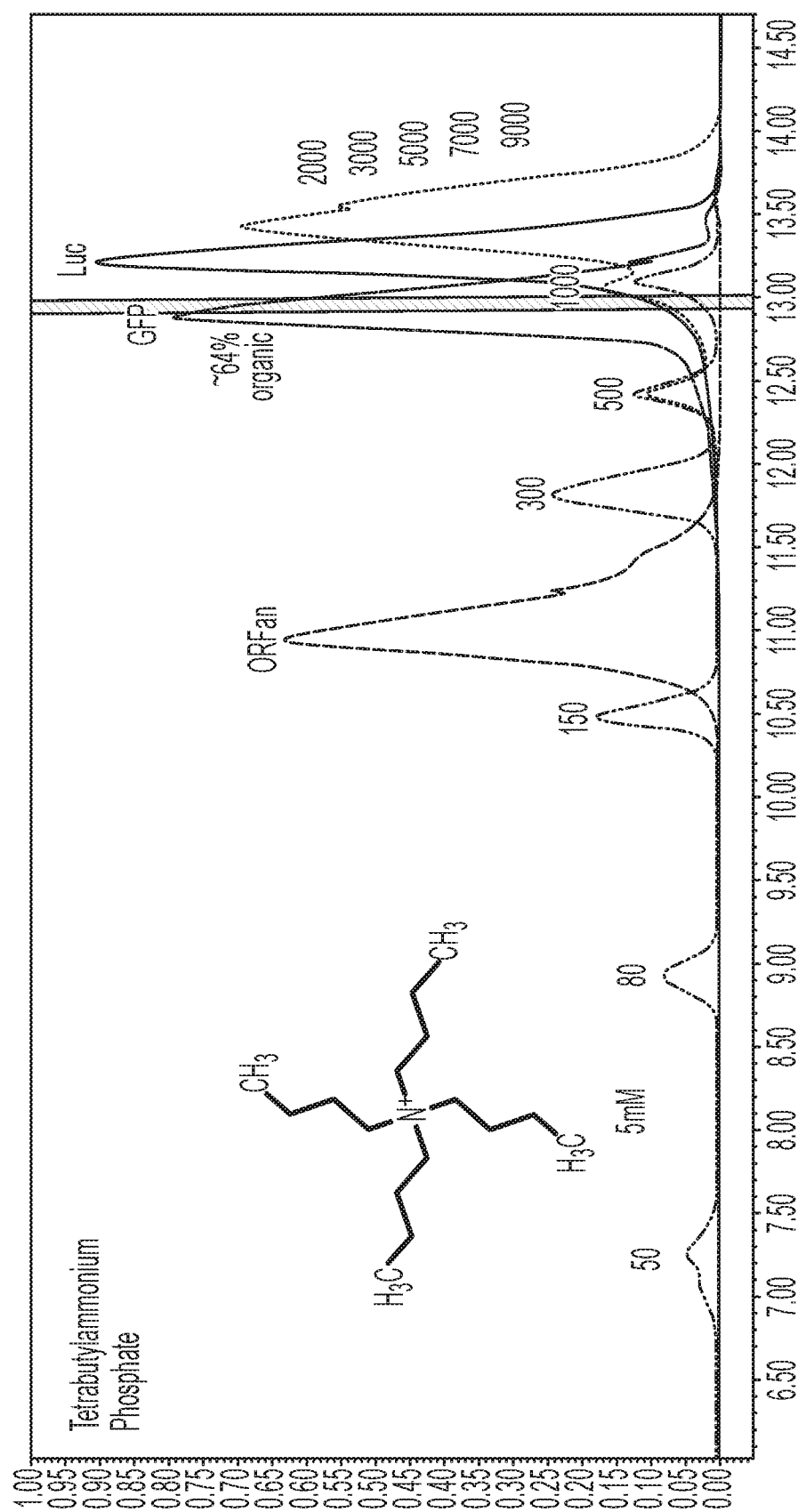
Figure 1D:
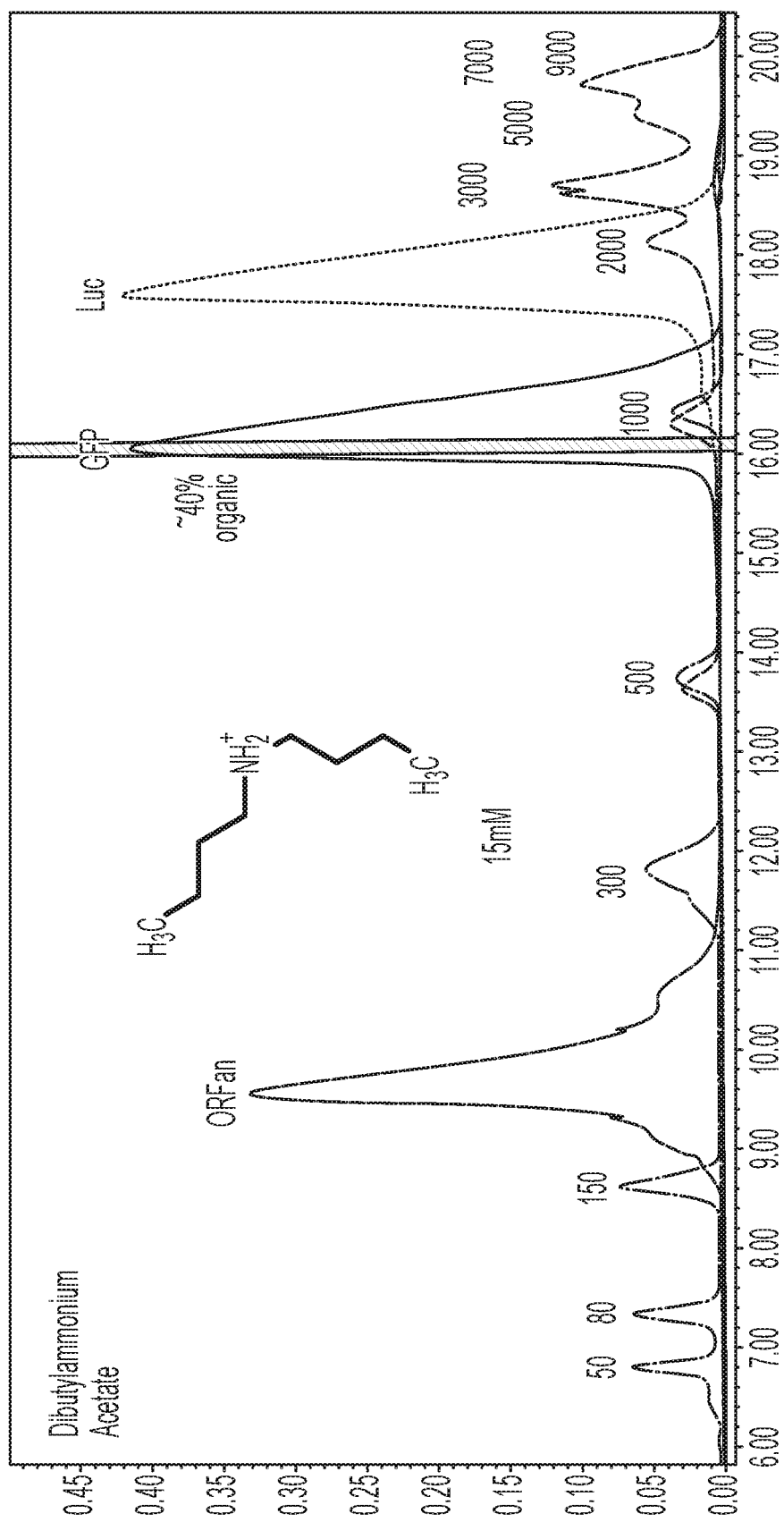

Each of the larger ion pairs screened gave a size-based separation, with the polyadenylated mRNAs eluting around the correct length according to the tailless commercial ladder (chemically unmodified) (FIGS. 1B-1D). Dibutylammonium acetate (DBAA) was selected for further investigation due to its high resolution and good mobile phase reproducibility.

Figure 2A:
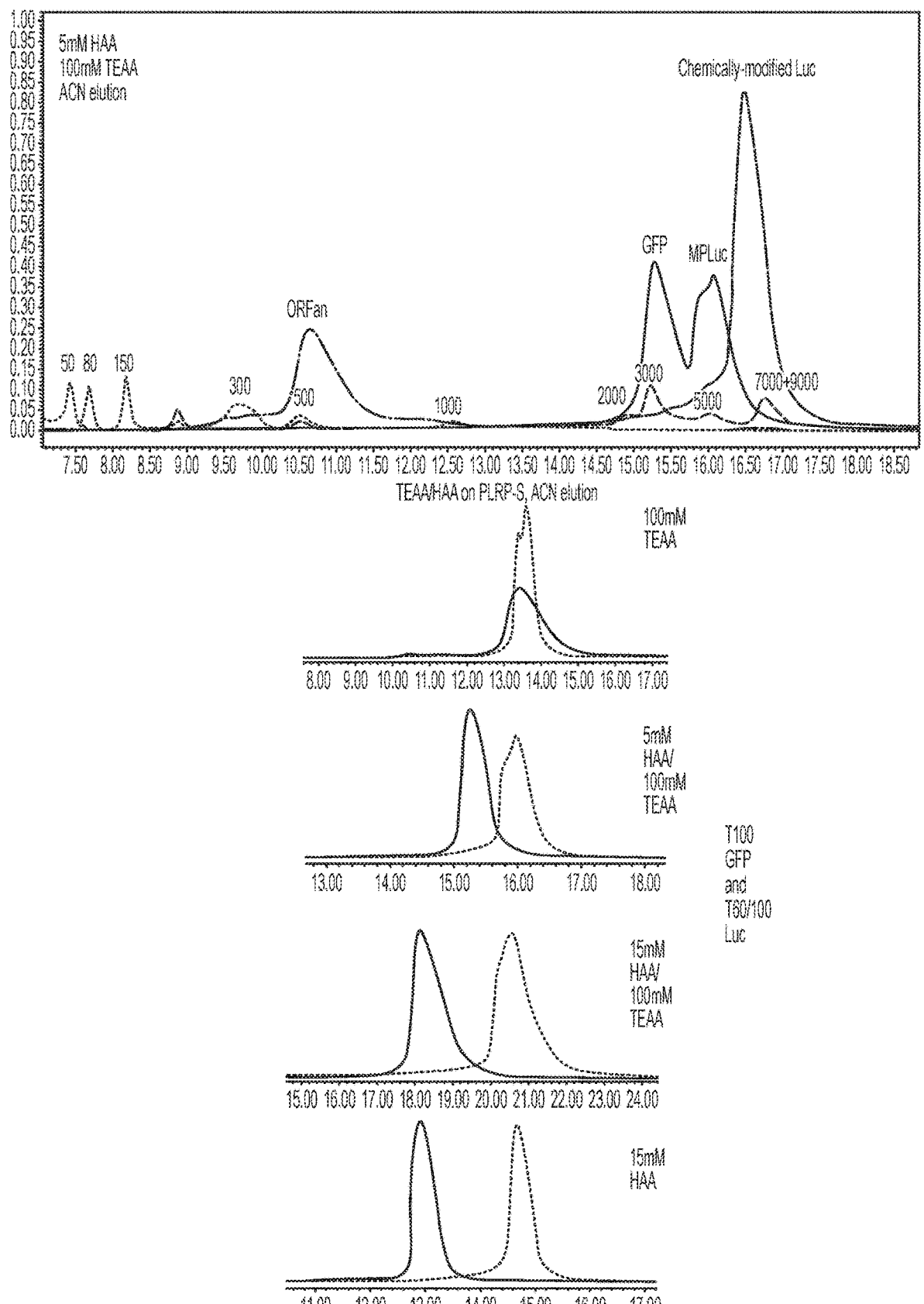
FIGS. 2A-2B show representative data for heterogeneous ion pairing agent tuning.
Figure 2B:
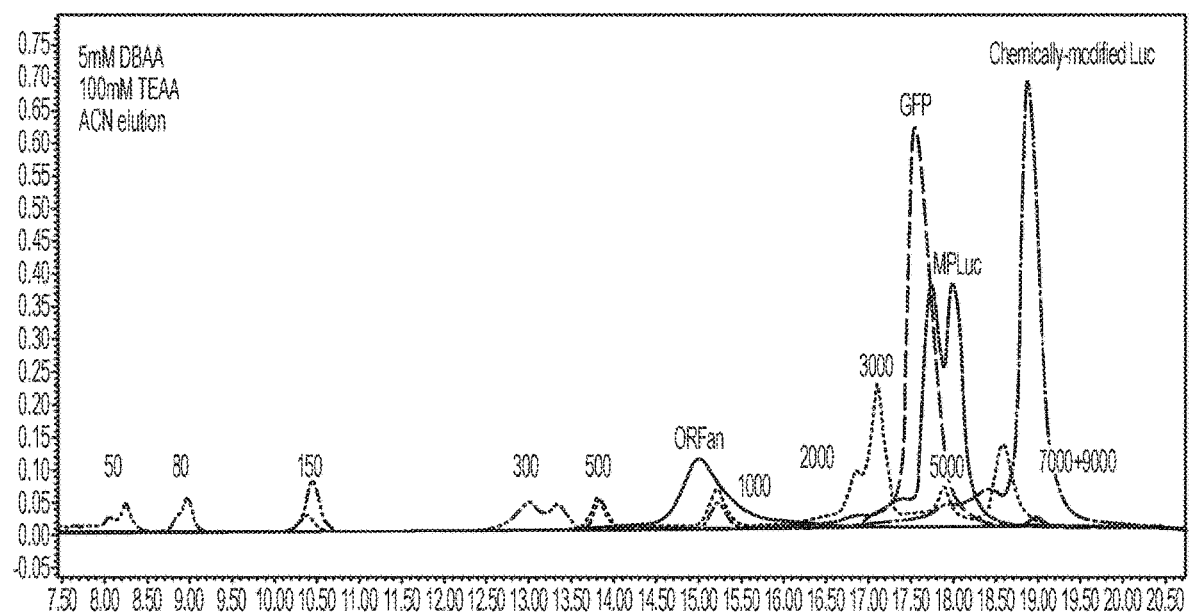

The use of heterogeneous ion pairing agents for 1) tuning selectivity between ion pair character; and 2) resolving multiple nucleic acid species with homogenous polyA tails using a standard preparation grade polystyrene and divinylbenzene column (e.g., a PLRP column or a DNAPac™ RP Column (High Performance Reversed-Phase LC Column)) was investigated. FIG. 2A shows representative chromatograms from mixed ion pairing systems (HAA/TEAA on top; DBAA/TEAA on bottom) for separation of four distinct mRNA species (ORFan, GFP, Chemically-modified Luc, MPLuc). FIG. 2B shows representative data demonstrating introduction of low concentrations of a bulkier ion pair (e.g., HAA) to a 100 mM TEAA ion pairing system results in altered resolution of multiple species within a complex mixture. Increasing concentrations of HAA in 100 mM TEAA shift mRNAs of different sizes (e.g., T100 GFP and T60/100 Luc) apart, and resolution is lost between the tail variants of Luc.

Data indicate that mixed ion pairing systems preserved high resolution of the commercial ladders, and gave some separation of the polyadenylated mRNAs. Some tail bias is preserved, as the mRNAs, while separated, eluted with much larger species in the tailless ladder than their actual size.

Figure 3A:
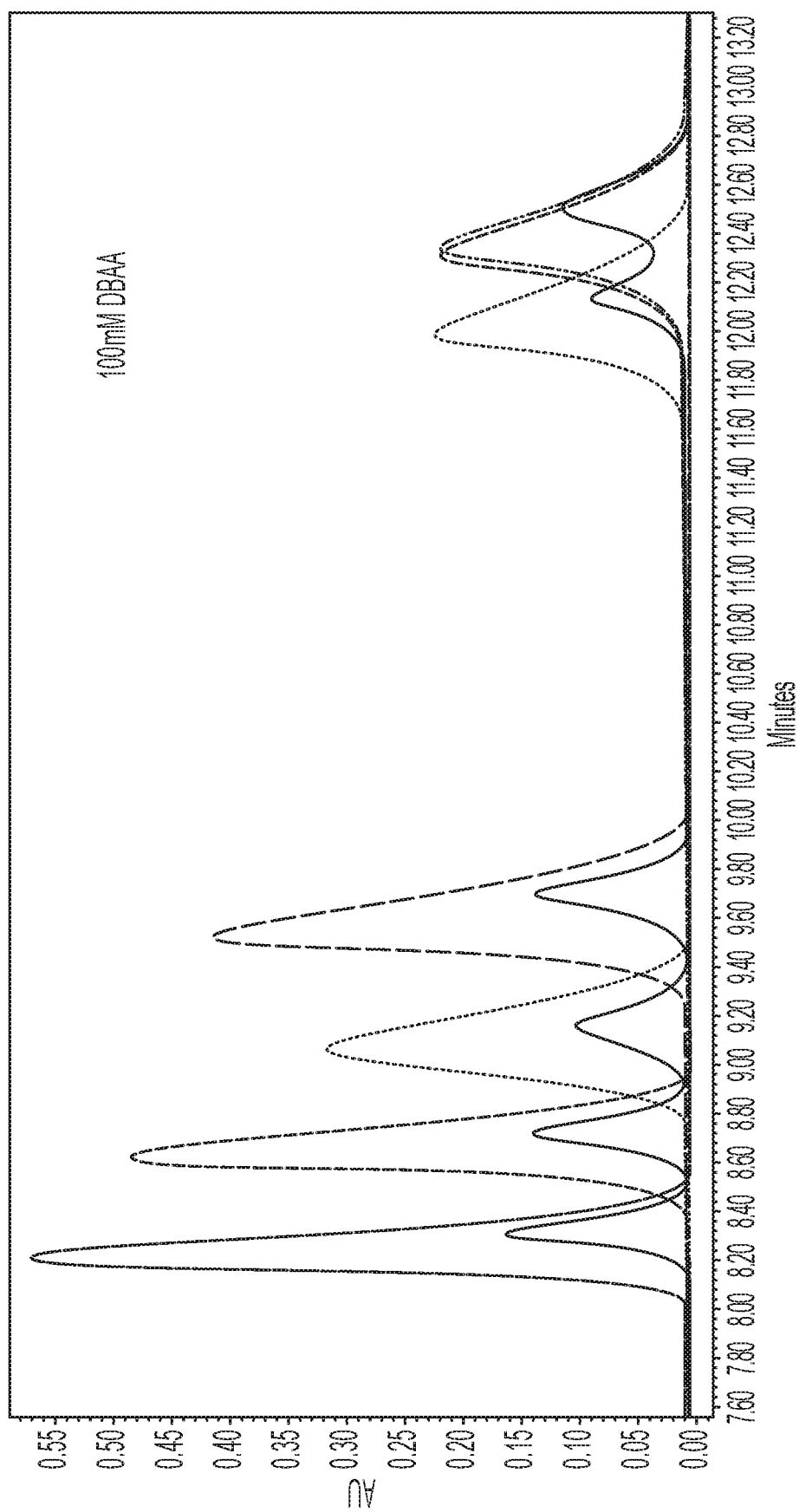
FIGS. 3A-3F show use of mixed ion pairing agents for HPLC analysis of a mixture containing 7 different mRNAs. Each of the 7 mRNA molecules in the mixture had a different length, ranging from approximately 700 bp to about 3500 bp. Even at high concentrations, systems of DBAA alone failed to resolve the longest species sufficiently (FIG. 3A), so mixed systems of DBAA and TEAA were investigated. Ratios of DBAA/TEAA tested were 5 mM DBAA/100 mM TEAA (FIG. 3B); 15 mM DBAA/100 mM TEAA (FIG. 3C); 75 mM DBAA/25 mM TEAA (FIG. 3D); 75 mM DBAA/50 mM TEAA (FIG. 3E); and 50 mM DBAA/50 mM TEAA (FIG. 3F).
Figure 3B:
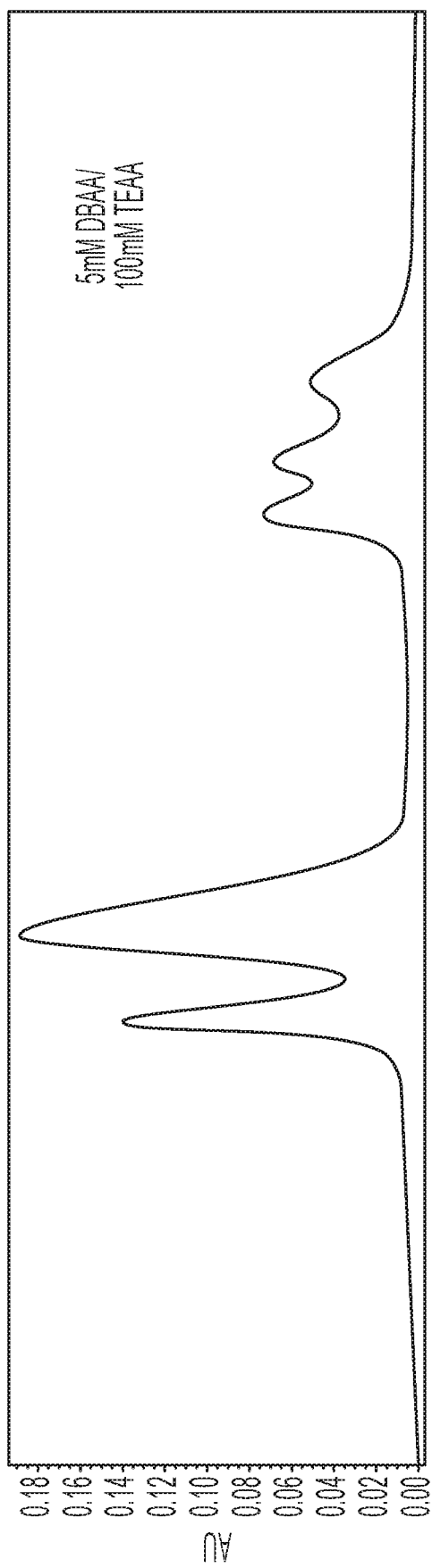
Figure 3C:
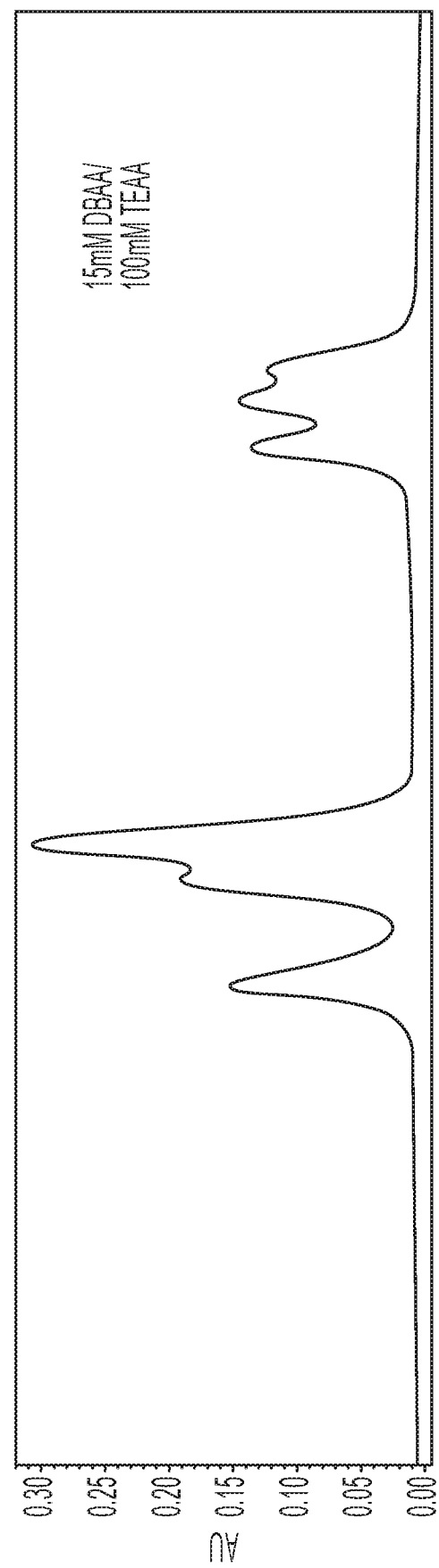
Figure 3D:
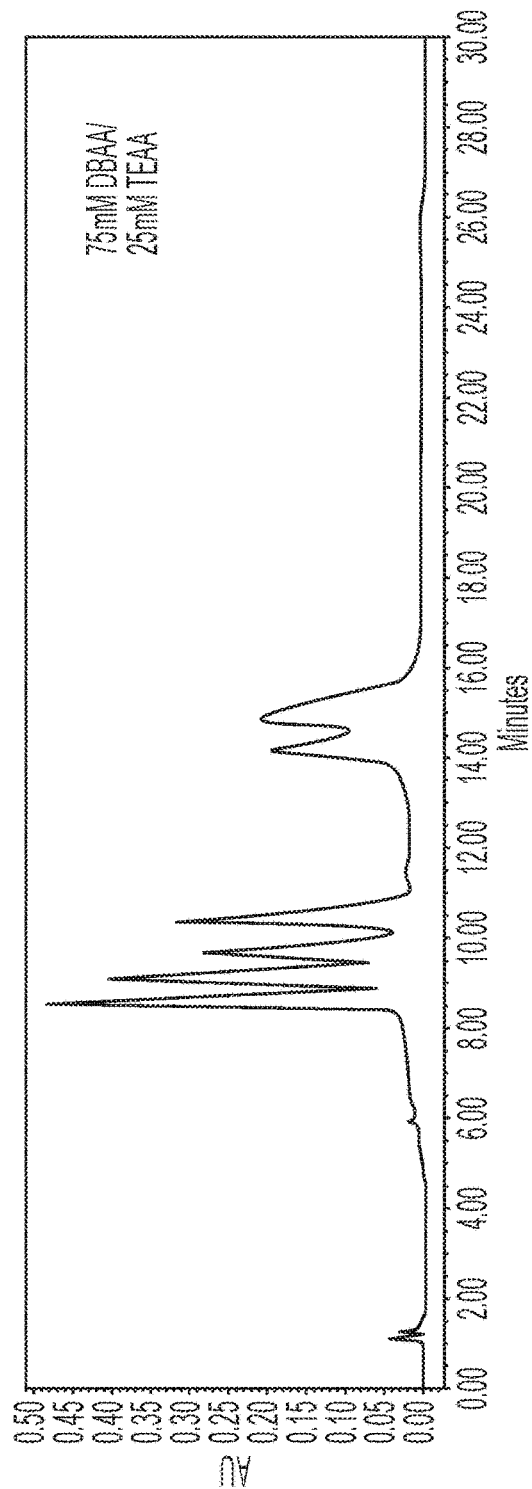
Figure 3E:
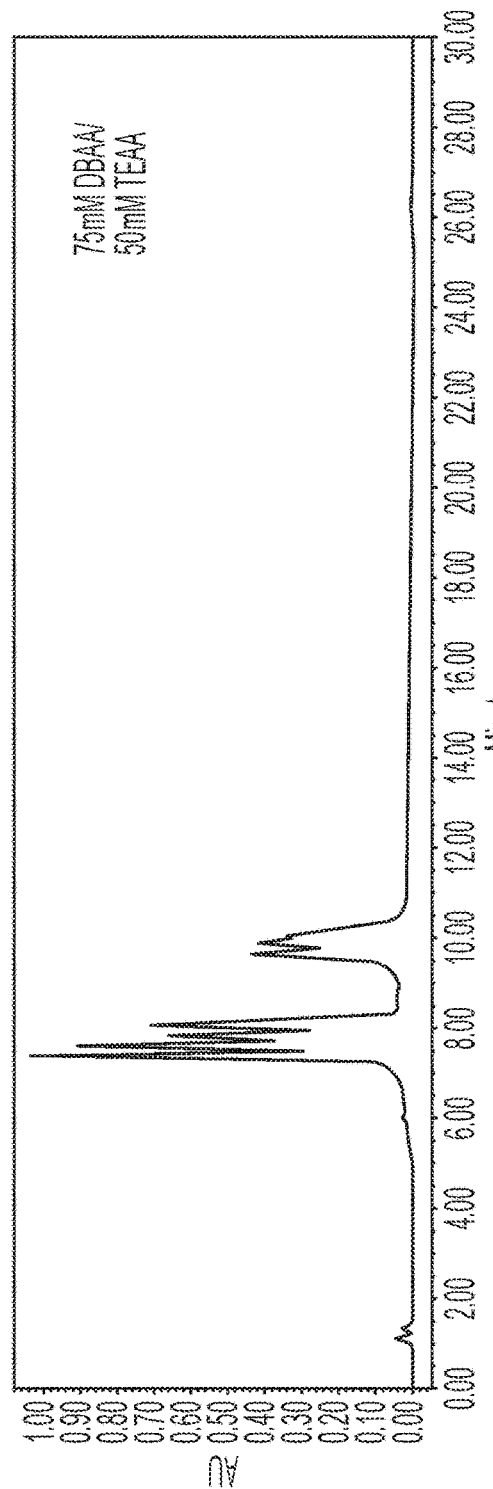
Figure 3F:
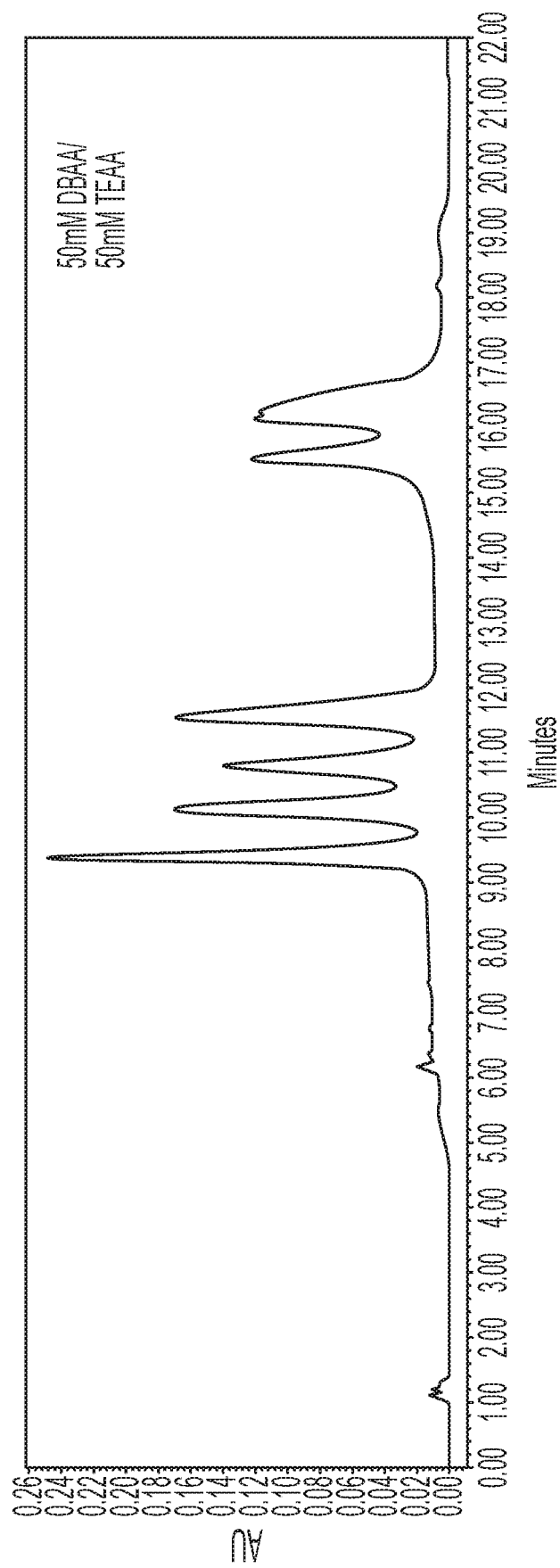

Use of mixed ion pairing agents for HPLC analysis of a mixture containing 7 different mRNAs was investigated next. Each of the 7 mRNA molecules in the mixture had a different length, ranging from approximately 700 bp to about 3500 bp. Even at high concentrations, systems of DBAA alone failed to resolve the longest species sufficiently (FIG. 3A), so mixed systems of DBAA and TEAA were investigated. Ratios of DBAA/TEAA tested were 5 mM DBAA/100 mM TEAA (FIG. 3B); 15 mM DBAA/100 mM TEAA (FIG. 3C); 75 mM DBAA/25 mM TEAA (FIG. 3D); 75 mM DBAA/50 mM TEAA (FIG. 3E); and 50 mM DBAA/50 mM TEAA (FIG. 3F).

Figure 4:
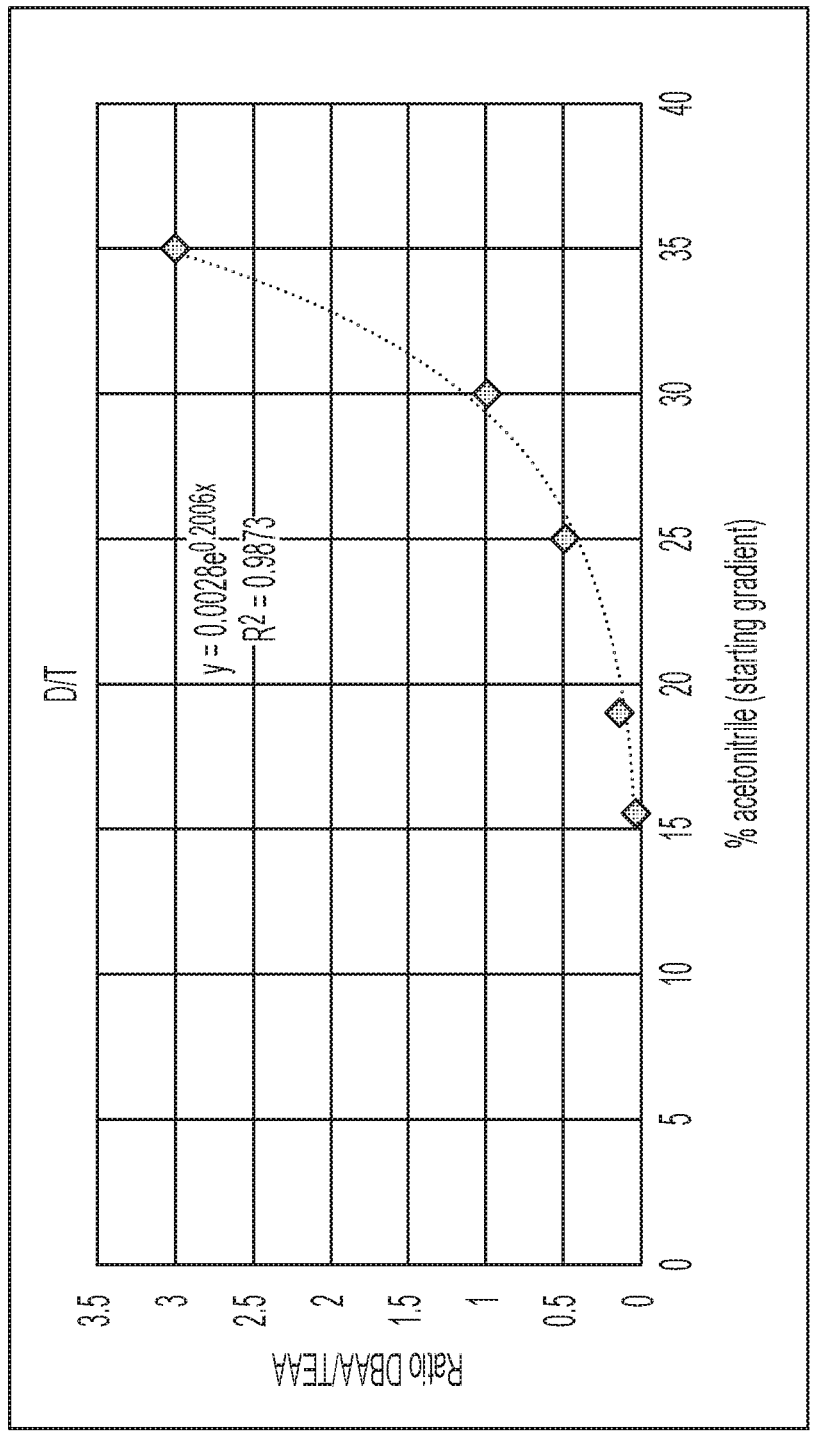
FIG. 4 shows data indicating that retention of polyadenylated RNA molecules is strongly affected by the ratio of ion pairing agents used for HPLC.

Data indicated that the retention time of the mRNA molecules was strongly affected by the ratio of ion pairing agents, as shown in FIG. 4 and Table 1 below:

TABLE 1

| Ratio DBAA/TEAA | % acetonitrile (starting gradient) |
|---|---|
| 5/100 | 15.5-17 |
| 15/100 | 19-20.5 |
| 50/100 | 25-26 |
| 50/50 | 30-32 |
| 75/25 | 35-38 |
| 100/0 | 40-42.5 |

Furthermore, data indicated that higher resolution of mRNA species was obtained at higher ion pair concentrations. However, each ratio of ion pairing agents elutes at a very narrow range (<2%). It was also observed that shorter length nucleic acids (e.g., <1-2 kb) were better resolved by higher DBAA concentration (and also exhibited higher retention) and that TEAA was necessary for high resolution with longer nucleic acid constructs (lower retention).

Figure 5:
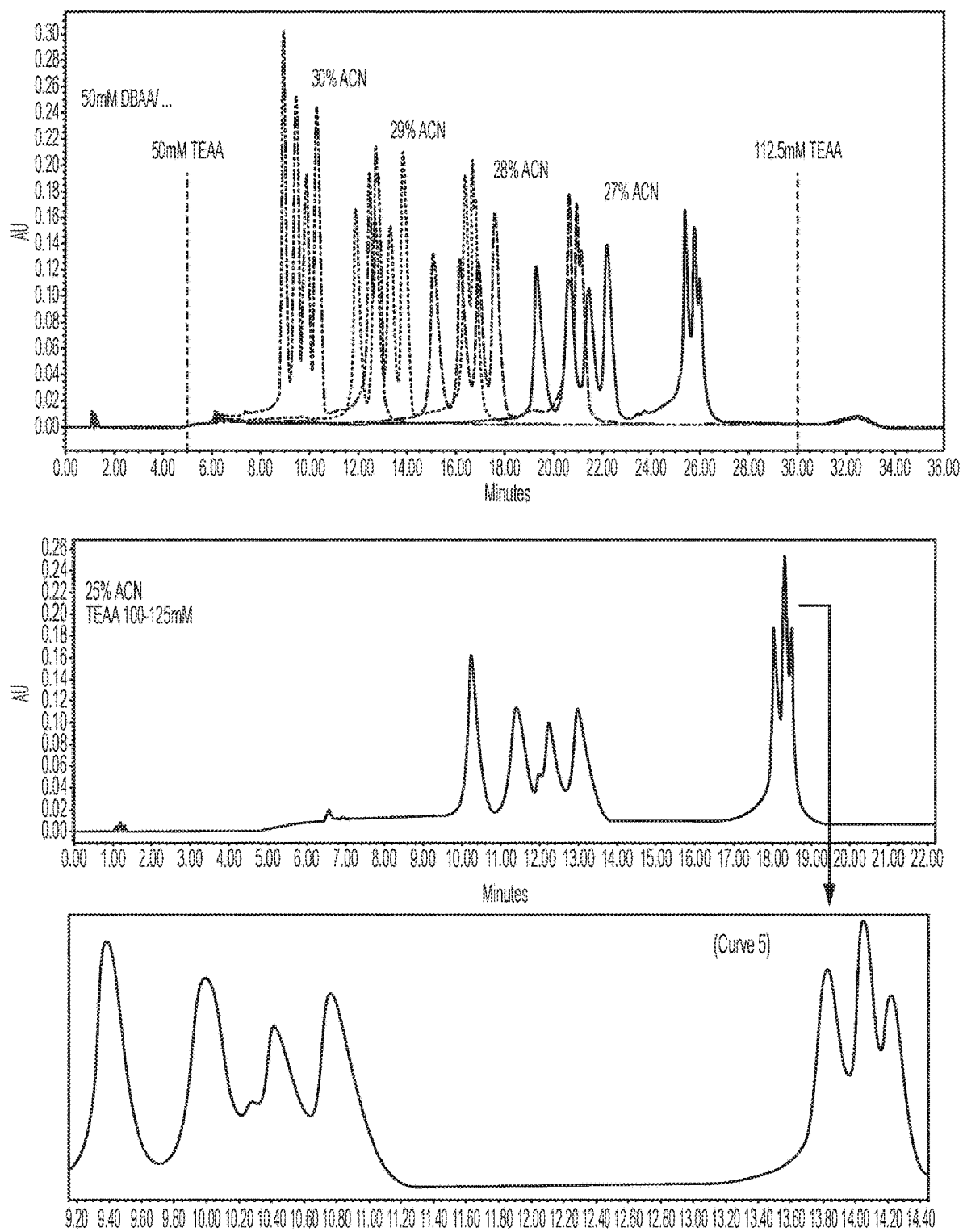
FIG. 5 shows representative chromatograms for HPLC of nucleic acids using "pseudo-isocratic" conditions where acetonitrile was held constant and a gradient of TEAA concentrations was used. Retention was reduced by increasing the concentration of TEAA at constant DBAA and acetonitrile, resulting in high resolution separations by "ion pair gradient". Similar to an isocratic separation, the acetonitrile concentration was tuned to find the best separation at these TEAA/DBAA conditions.

Given the narrow elution range of each of the size-based systems described above, as well as a need for less retentive conditions (e.g., higher TEAA:DBAA ratios) to better resolve late-eluting, longer nucleic acid species, "pseudo-isocratic" conditions where acetonitrile was held constant were investigated (FIG. 5). Retention was reduced by increasing the concentration of TEAA at constant DBAA and acetonitrile, resulting in high resolution separations by "ion pair gradient". Similar to an isocratic separation, the acetonitrile concentration was tuned to find the best separation at these TEAA/DBAA conditions.

Figure 6A:
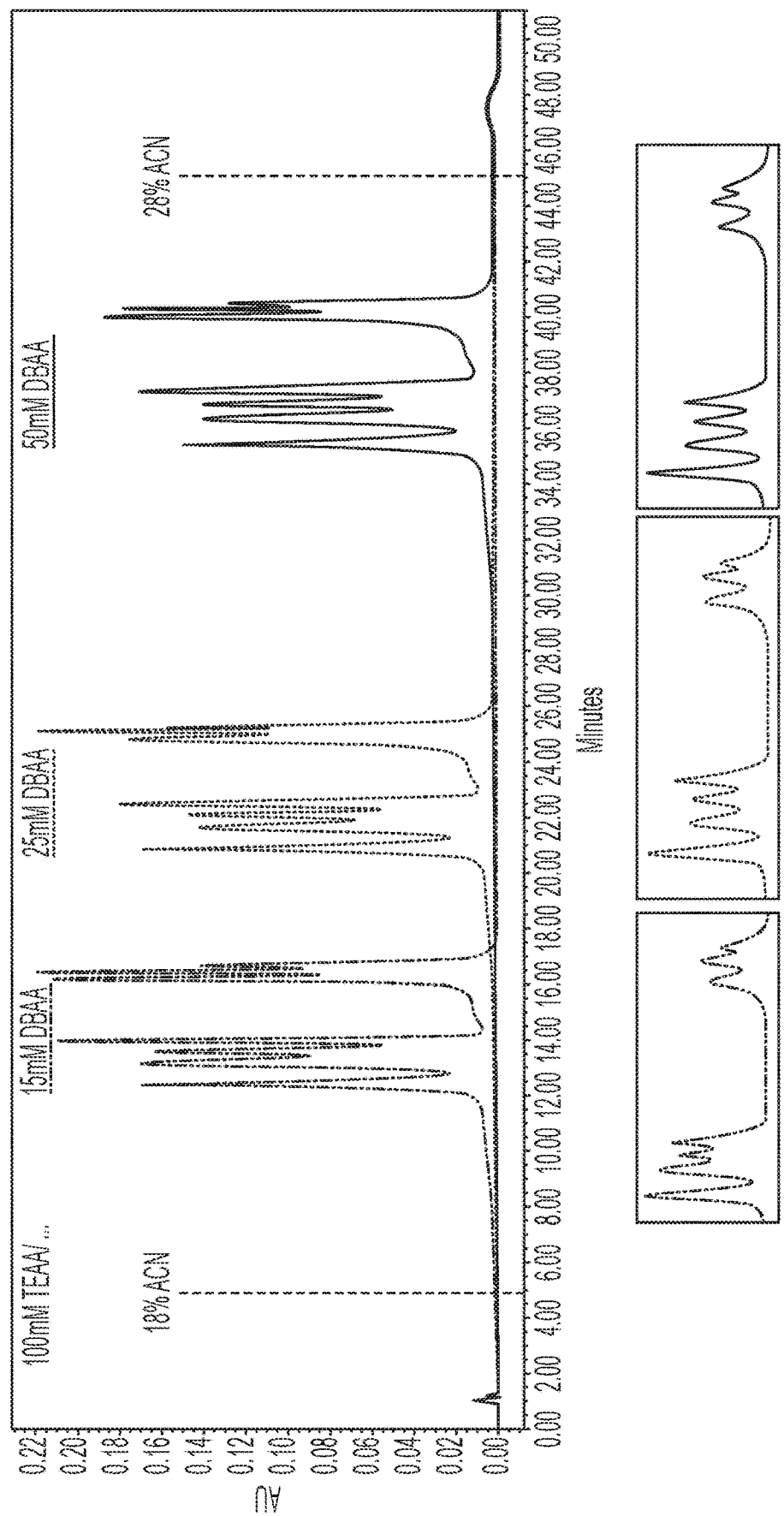
FIGS. 6A-6D show representative HPLC chromatograms
Figure 6B:
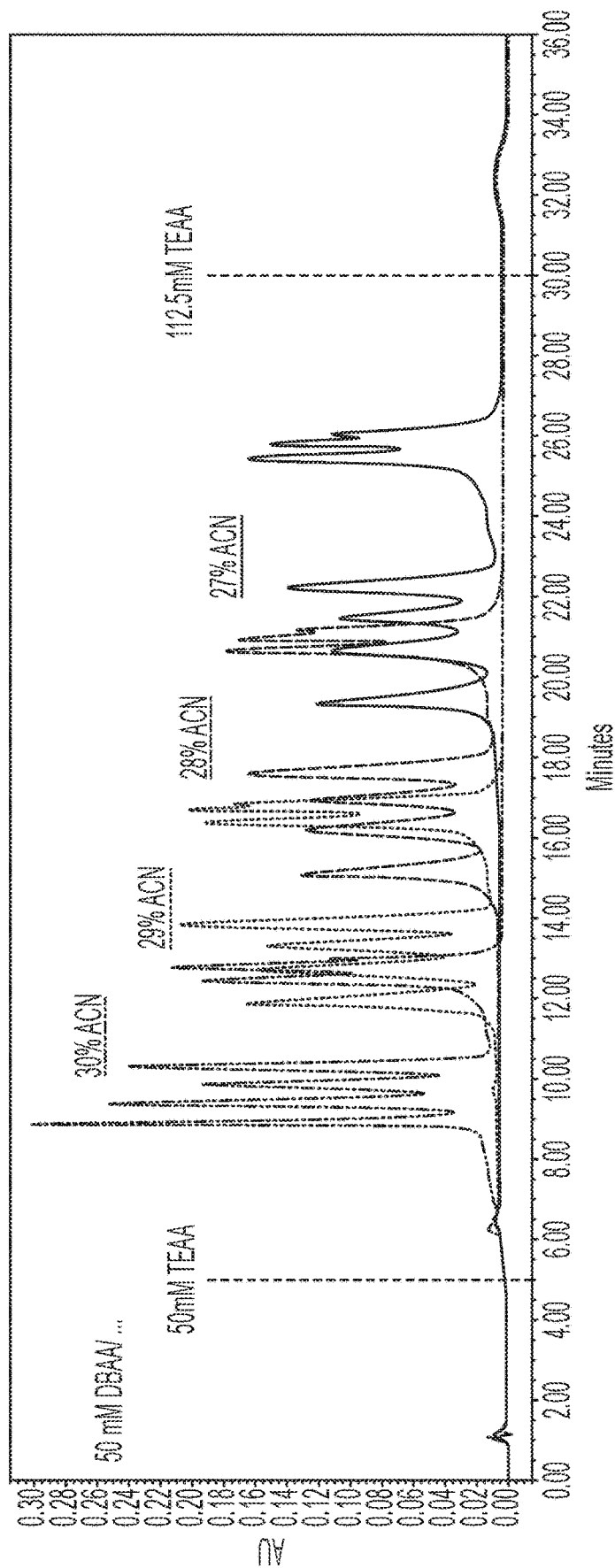
Figure 6C:
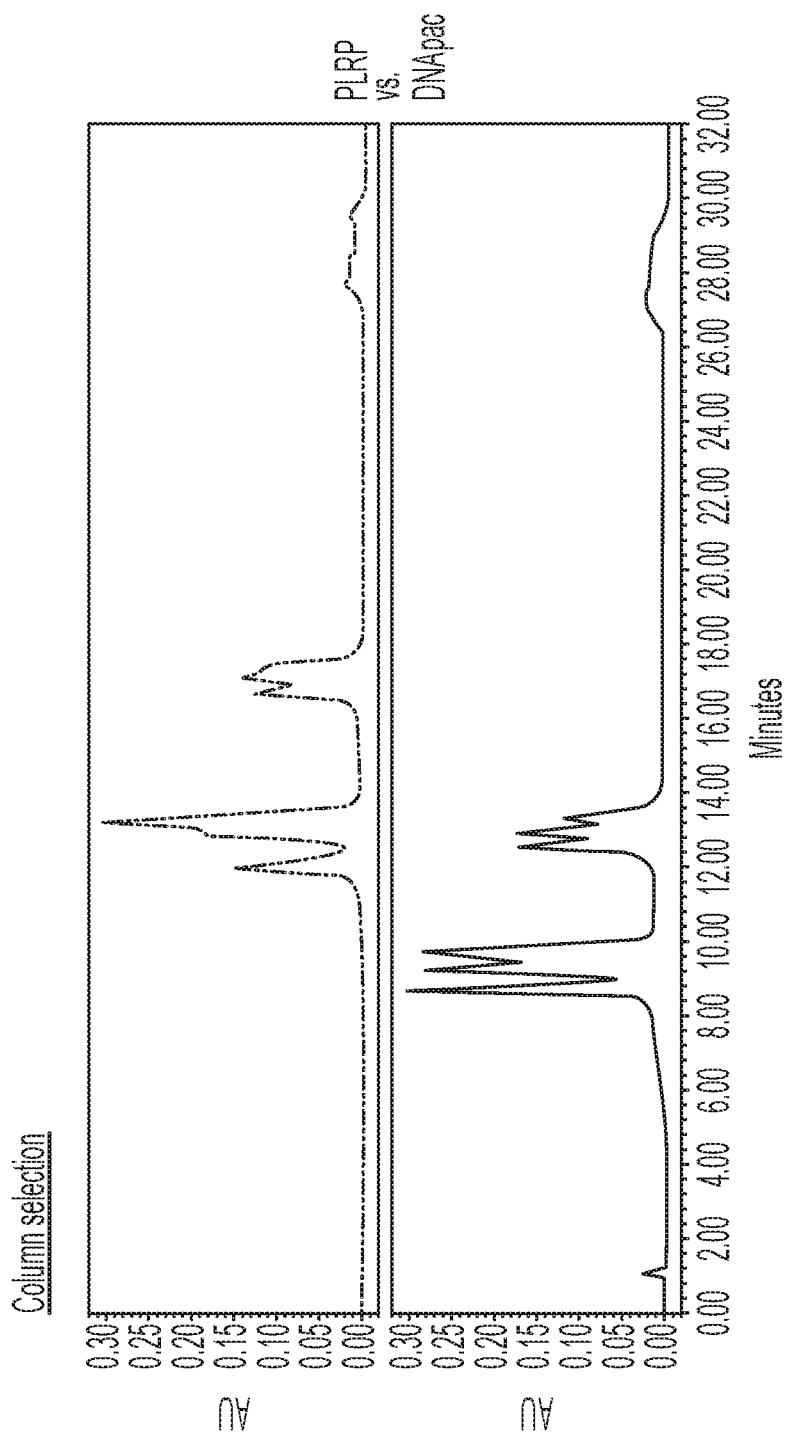
Figure 6D:
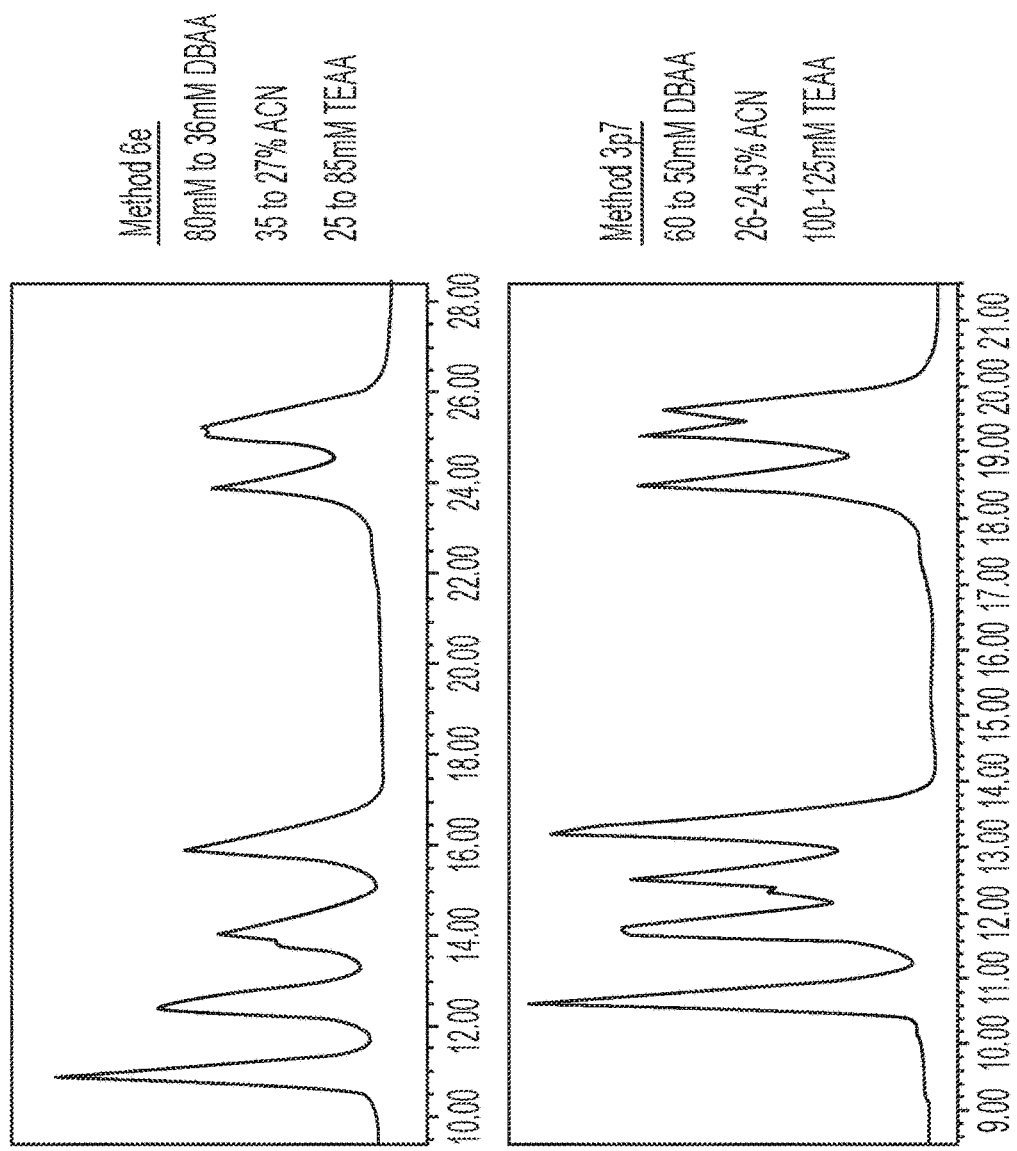

FIGS. 6A-6D show representative HPLC chromatograms FIGS. 6A and 6B show a comparison of linear separation methods (FIG. 6A) with constant organic phase (ACN):ion pair gradient elution (FIG. 6B) for complex mixtures of mRNA. FIG. 6C shows representative chromatograms comparing HPLC solid phase (e.g., PLRP column vs. DNAPac™ RP Column (High Performance Reversed-Phase LC Column)) performance in methods described by the disclosure FIG. 6D shows representative chromatograms for quaternary ion pair (IP)/organic gradients as described by the disclosure. Briefly, the concentrations of TEAA and DBAA are individually controlled, to tune the separation in each region of the elution gradient. Each chromatogram was produced using a "reversed" gradient for reversed phase, with decreasing acetonitrile through the elution region to allow a wide range of compositions, and also includes the use of high DBAA concentration to separate the shorter species; increasing TEAA to is used to resolve mRNAs greater than 2 kb.

Example 2

One embodiment of a method for chromatographic separation of polynucleotides is described below:
Mobile phase A: 100 mM triethylammonium acetate (TEAA)/50 mM dibutylammonium acetate (DBAA) in water
Mobile phase B: 100 mM triethylammonium acetate (TEAA)/50 mM dibutylammonium acetate (DBAA), 50% v/v acetonitrile in water
Column: DNAPac™ RP (High Performance Reversed-Phase LC Column) 2.1 mm×100 mm length (Thermo Fisher part #0889239)
Run time: 24 min
Run temperature: 65° C.
Autosampler Temperature: 4° C.
RNA concentration prior to injection: 0.1-0.5 mg/mL
Injection Volume: 20 µL
Detection: UV absorbance @ 260 nm
System: Waters H-Class UPLC or equivalent
Gradient: shown below in Table 1

TABLE 1

| Time (min) | % MPA | % MPB | Flow (mL/min) |
|---|---|---|---|
| 0 | 75% | 25% | 0.35 |
| 1.5 | 75% | 25% | 0.35 |
| 4.5 | 50% | 50% | 0.35 |
| 19.0 | 44% | 56% | 0.35 |
| 19.5 | 0% | 100% | 0.35 |
| 20.0 | 0% | 100% | 0.35 |
| 20.1 | 75% | 25% | 0.35 |
| 24.0 | 75% | 25% | 0.35 |

Figure 7:
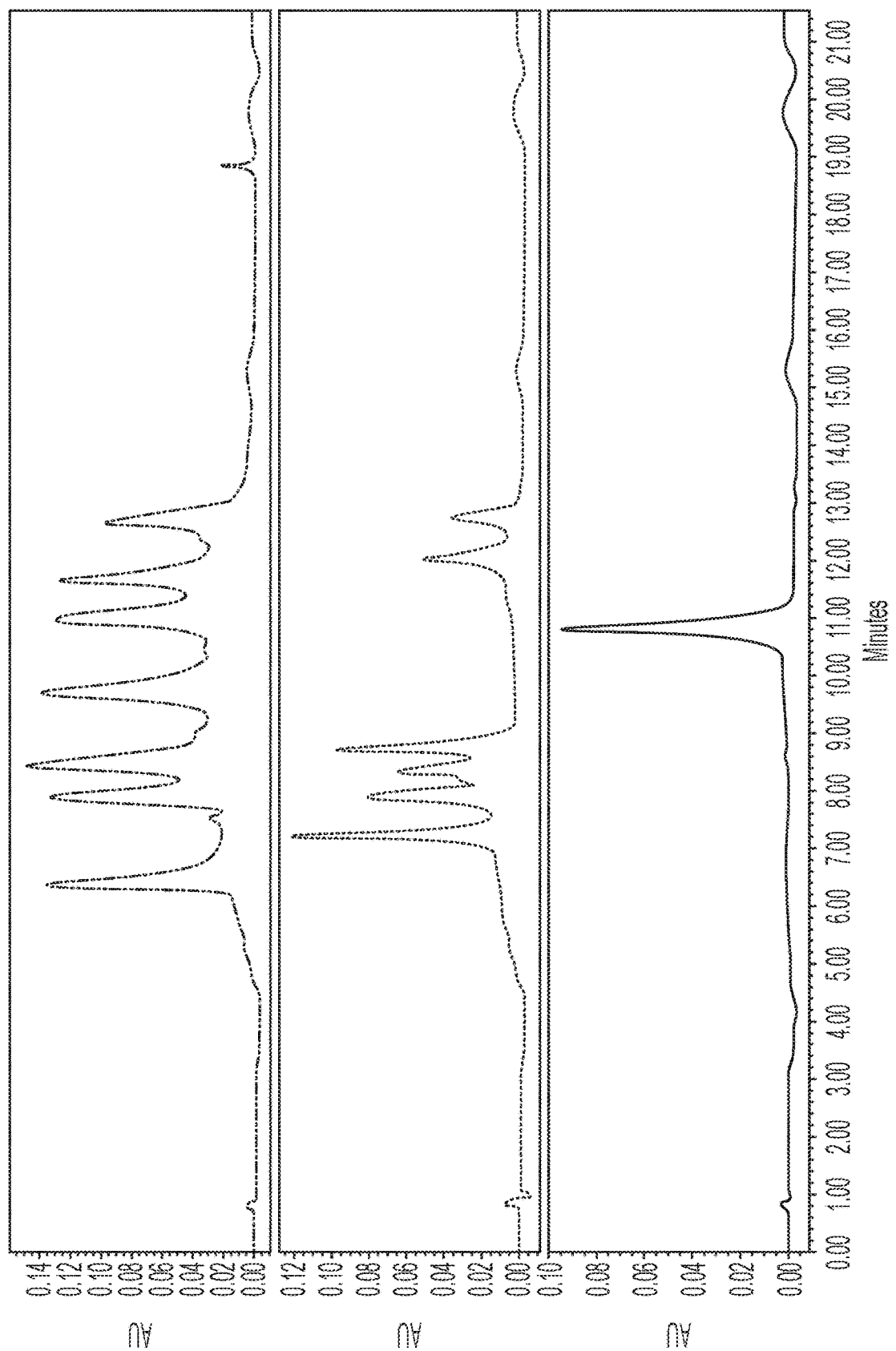
FIG. 7 shows representative chromatograms of a mRNA ladder (top), a mixture containing 6 different mRNAs (middle), and a single species mRNA composition (bottom) using the ion pair gradient HPLC method described in Example 2.

FIG. 7 shows representative HPLC chromatograms for a mRNA ladder (top), mixture containing 6 different mRNAs, and single mRNA species composition that were produced using the method described above.

Figure 8:
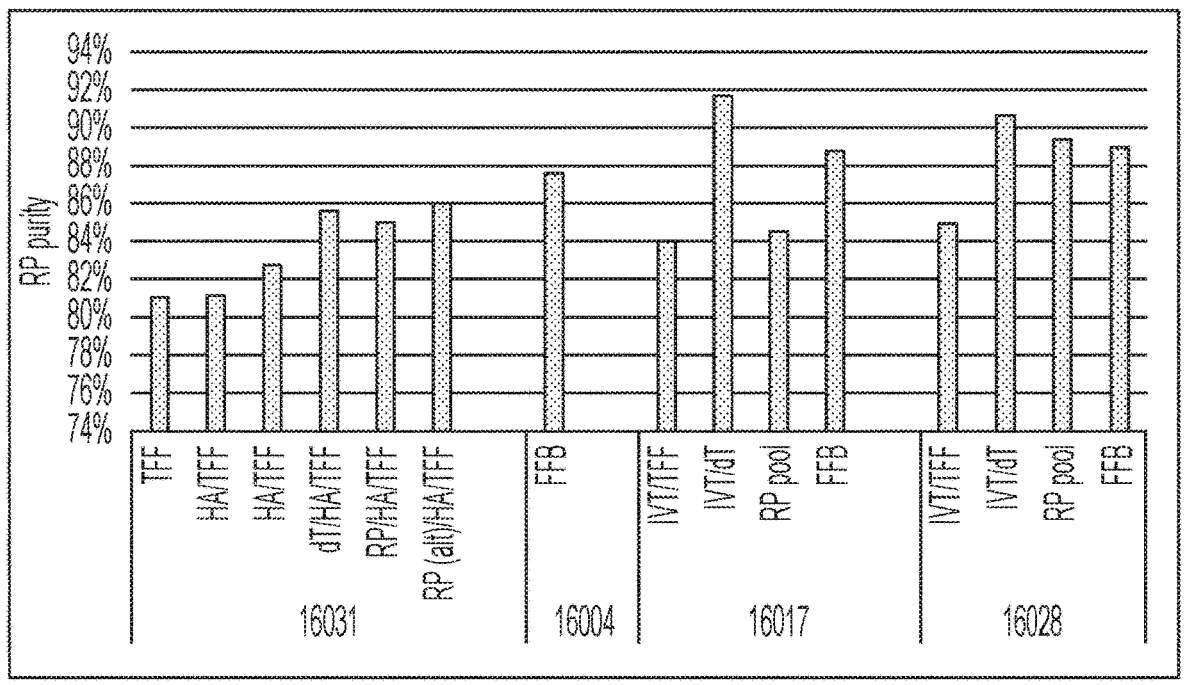
FIG. 8 shows HPLC chromatograms of pharmaceutical preparation samples from four development lots of a single-species mRNA pharmaceutical preparation. Representative chromatograms are shown for lot numbers 106004, 106017 and 106028 (left to right, respectively). TFF tangential flow filtration; hydroxyapatite purification; dT oligo dT purification; IVT in vitro transcription; FFB final formulated bulk.
Figure 8:
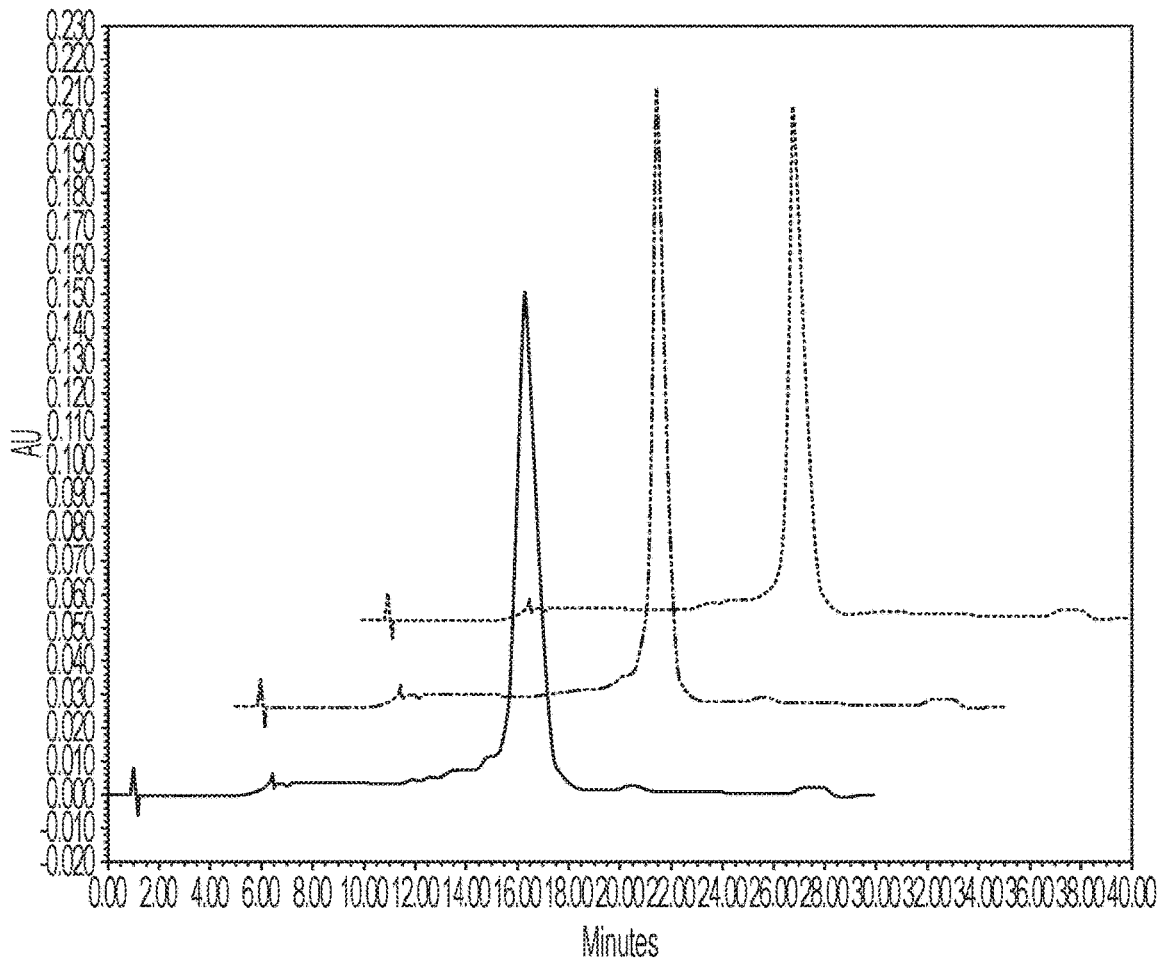

The method described above was then used to assess in-process samples, process variants, and lot-to-lot purity of a single-species mRNA pharmaceutical preparation. FIG. 8 shows HPLC chromatograms of pharmaceutical preparation samples from four development lots; in the first (16031), process variants (e.g., hydroxyapatite (HA) purified, oligo dT purified, tangential flow filtration (TFF) purified, reverse phase purified, and combinations thereof) were compared to the crude TFF purified reaction. A gain in purity was observed with additional dT or RP purification apparent (FIG. 8, 16030). The next three lots (16004, 17, and 28) compare available process retains across a similar process. The impact of dT purification on the crude IVT RNA is clear. It was observed that both lots 16017 and 16028 show a drop in purity of the final material after HPLC purification, likely due to in-process degradation not cleared by the tail-based purifications. The three lots of final material (final formulated bulk, FFB) show similar final purity, indicating good process reproducibility.

Figure 9:
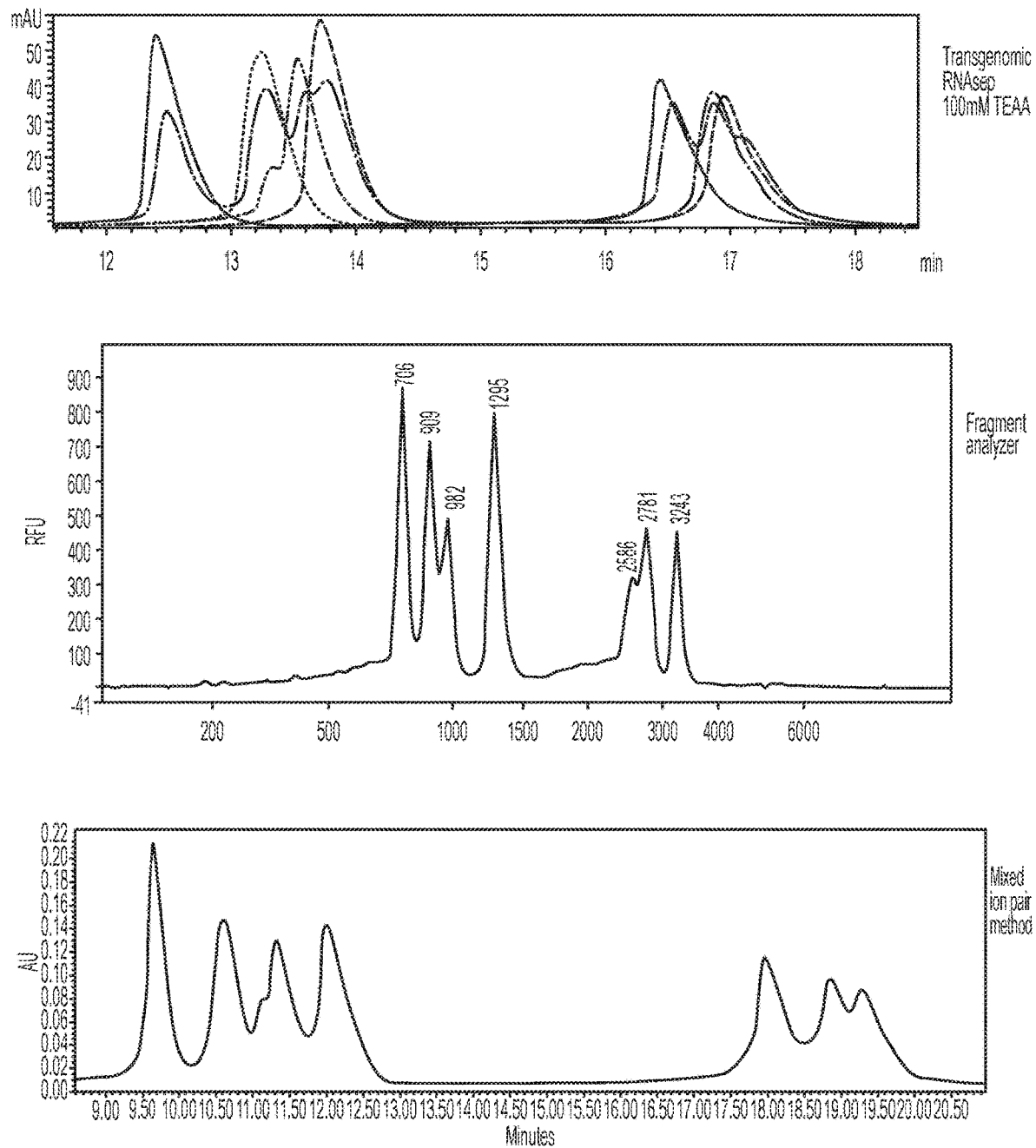
FIG. 9 shows a comparison of chromatographic purity data obtained using mixed ion pair methods as described by the disclosure (bottom) with nucleic acid separation using thermally denaturing conditions (e.g., Transgenomic wave cartridge) or capillary electrophoresis (CE; fragment analyzer) methodologies.

The method described above was then used to separate the RNA molecules present in a mixture containing 7 different mRNAs. FIG. 9 shows a comparison of separations obtained using mixed ion pair methods as described by the disclosure (bottom) with nucleic acid separation using a non-porous HPLC reverse phase column (e.g., Transgenomic wave cartridge) (top) or capillary electrophoresis (CE; fragment analyzer) (middle) methodologies.

Example 3

Figure 10:
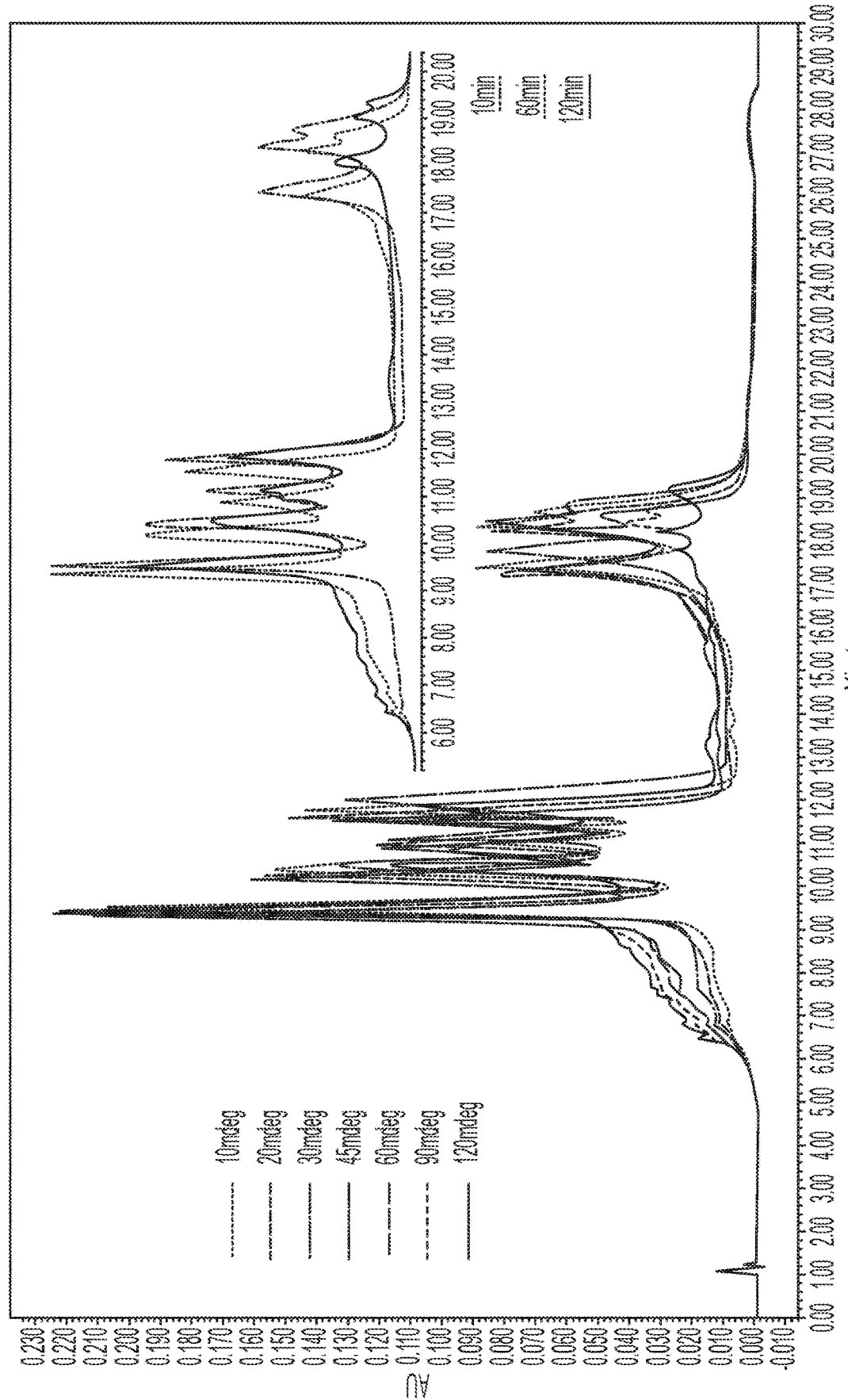
FIG. 10 shows representative HPLC chromatograms of a 65° C. heat-stressed mixture containing 7 different mRNAs. Degradation was observed in the regions before and between the peaks. The loss of area was more apparent in longer than shorter constructs.
Figure 10:
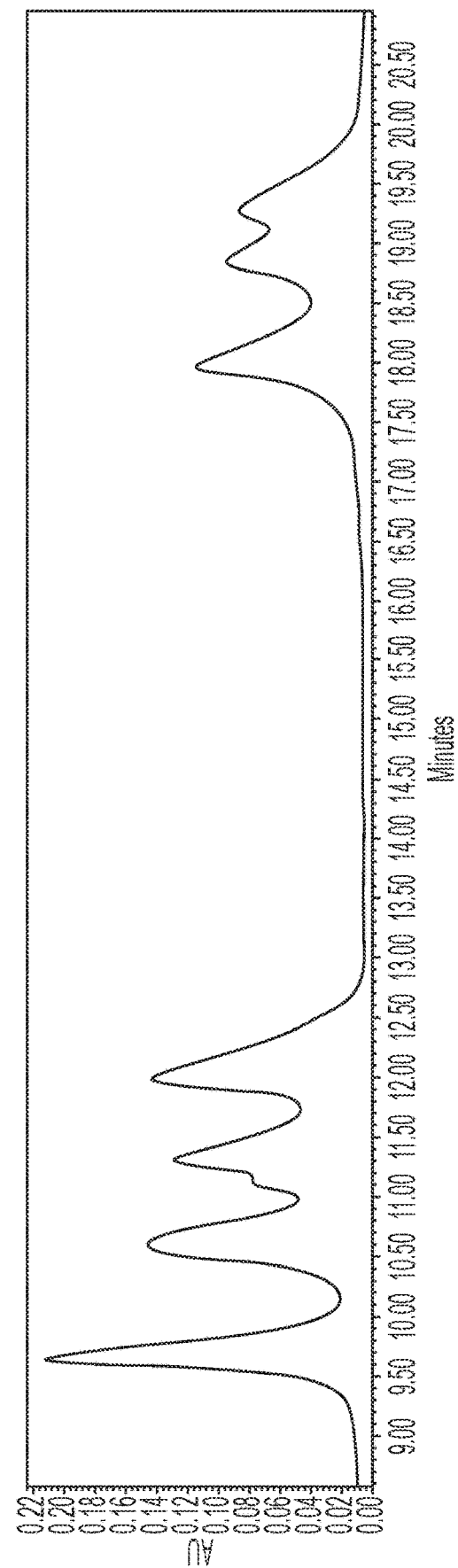
Figure 10:
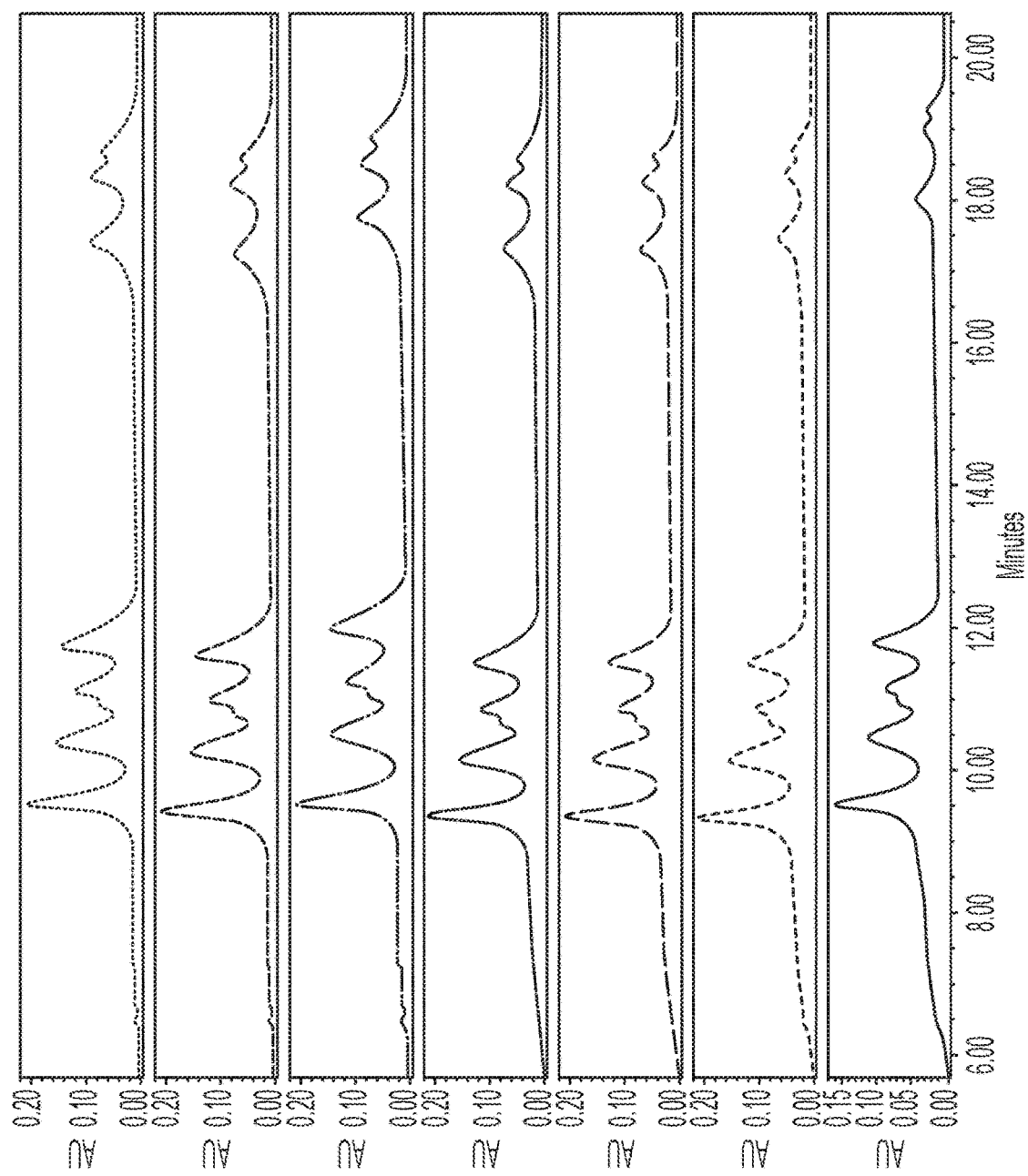

The mixture containing 7 different mRNAs described in the Examples above was heat stressed to generate time points from 10 minutes to 2 hours. HPLC was performed according to the method described in Example 2. FIG. 10 shows the resulting chromatograms. Degradation products were observed in the regions before and after each mRNA peak; loss of area was more apparent in longer molecules as opposed to shorter molecules, due to the greater chance of hydrolysis of longer molecules.

Whether the methods described by the disclose are capable of separating two mRNA molecules having a similar size but difference base composition (e.g., sequence) was investigated.

Figure 11:
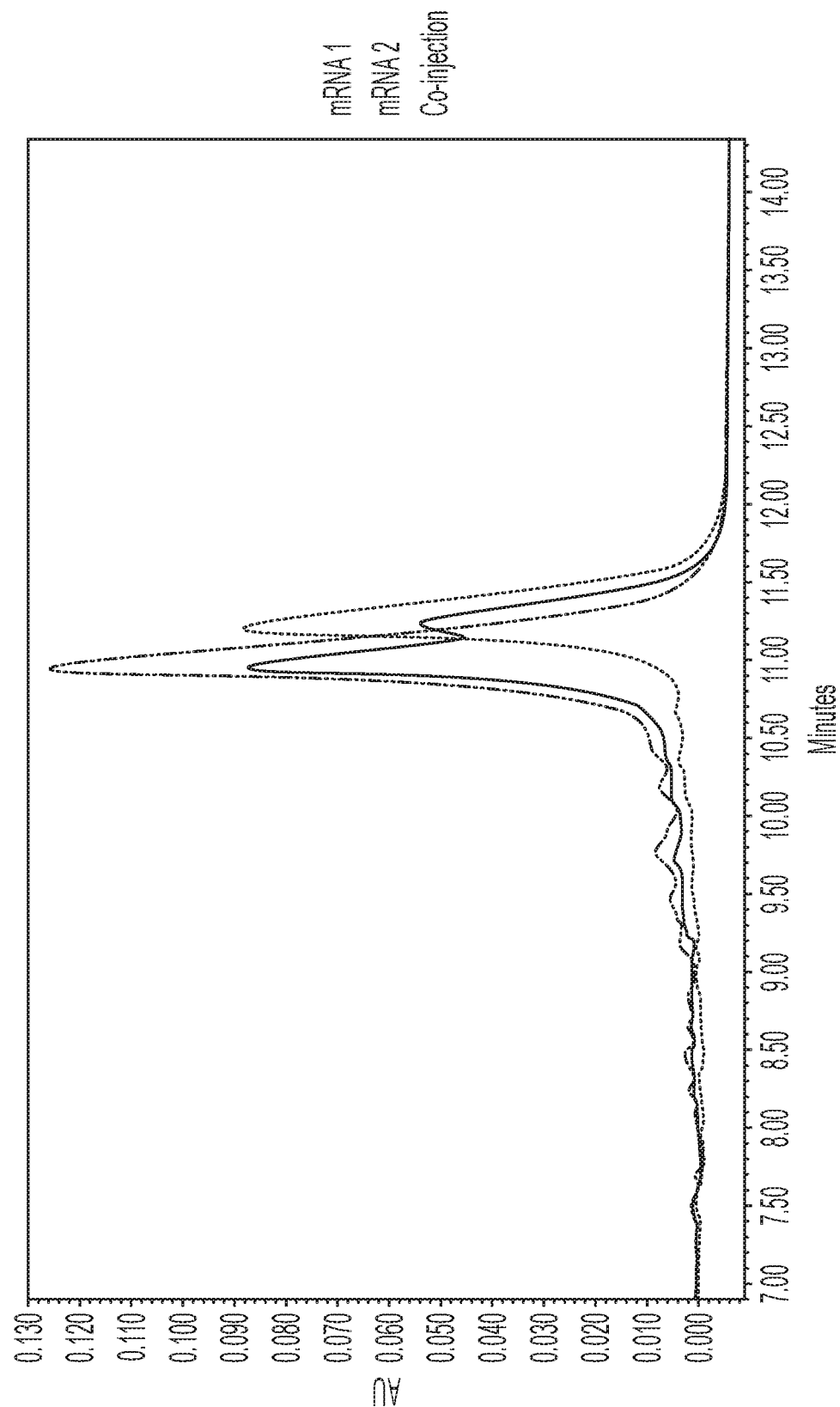
FIG. 11 shows an HPLC chromatogram of a composition comprising two species of mRNA molecules which are of very similar size (~1900 bp) but differ in sequence. Data indicate HPLC methods as described by the disclosure are capable of resolving each molecule of the mixture.

FIG. 11 shows an HPLC chromatogram of a composition comprising two species of mRNA molecules which are of very similar size (~1900 bp) but differ in sequence. Data indicate HPLC methods as described by the disclosure are capable of resolving each molecule of the mixture.

Example 4

Figure 12:
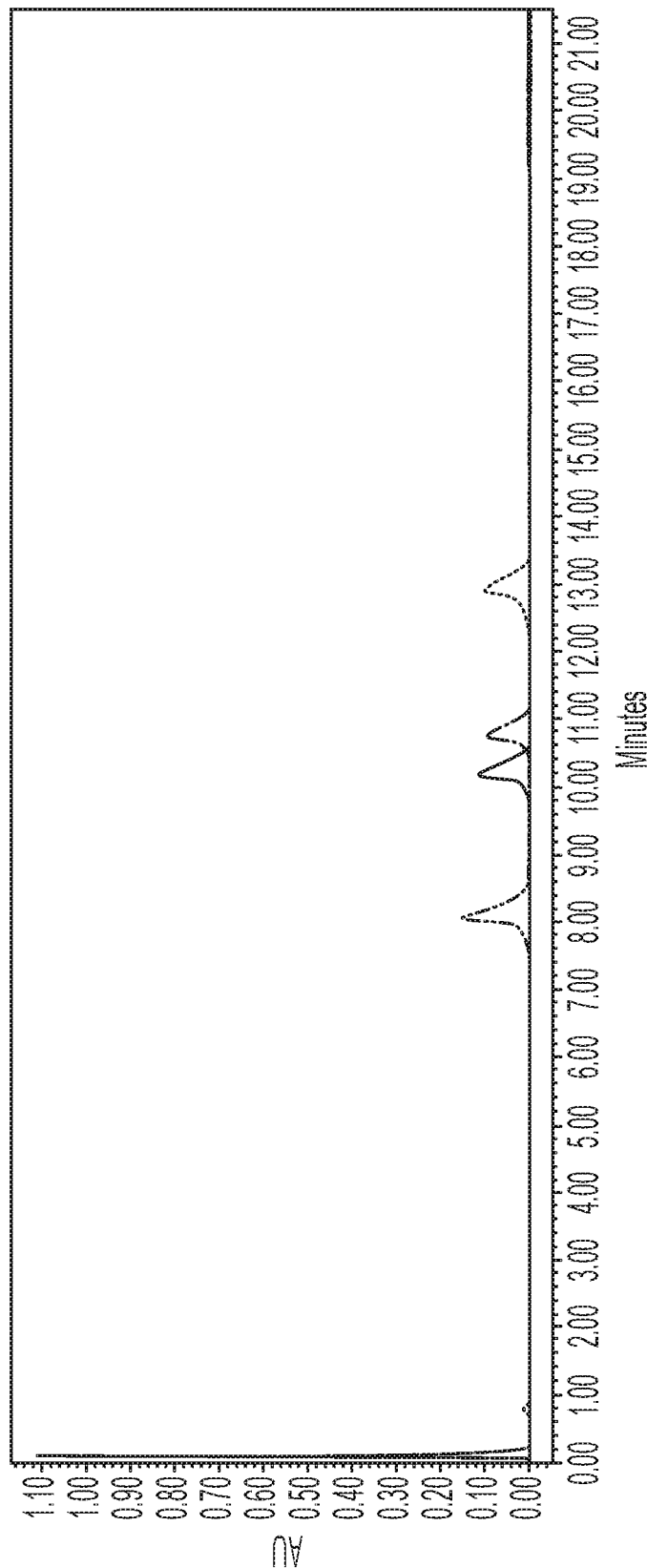
FIG. 12 shows a chromatogram of four mRNA constructs for investigation of the mass balance and carryover of HPLC methods described by the disclosure.

Mass balance (Table 2) and carryover (Table 3) of HPLC methods described by the disclosure were investigated for mRNA constructs. Briefly, mass balance was derived by running RNA samples through an analytical HPLC column, followed by injection of the same amount of RNA samples into the HPLC without a column in-line. Peak area of column mRNA samples was compared to theoretical area (e.g., peak area of RNA sample with no column in line) using the following formula: (Area (post column recovery)/Area(theoretical))/100. Carryover was derived by running RNA samples through an analytical HPLC column, followed by elution of a blank sample (no RNA). Residual RNA (carryover) was calculated by the following formula: (Area (blank)/Area(method))/100. FIG. 12 shows a chromatogram for each construct tested for mass balance.

TABLE 2

Mass Balance

| Construct | Area(theoretical) | Area(post-column recovery) | Mass balance |
|---|---|---|---|
| mRNA 1 | 2958531 | 3111960 | 105% |
| mRNA 2 | 2840752 | 2730302 | 96% |
| mRNA 3 | 2599871 | 2417156 | 93% |
| mRNA 4 | 2763281 | 2634380 | 95% |

TABLE 3

Carryover

| Sample | Method Area | Blank Area | % carryover |
|---|---|---|---|
| Ladder | 120627688 | 161196 | 0.13% |
| mRNA 1 | 11955430 | 24025 | 0.20% |
| mRNA 2 | 14515379 | 12758 | 0.09% |
| mRNA 3 | 12593173 | 51242 | 0.41% |
| mRNA 4 | 11251251 | 56737 | 0.50% |
| mRNA 5 | 12898349 | 28182 | 0.22% |

Example 5

Figure 13:
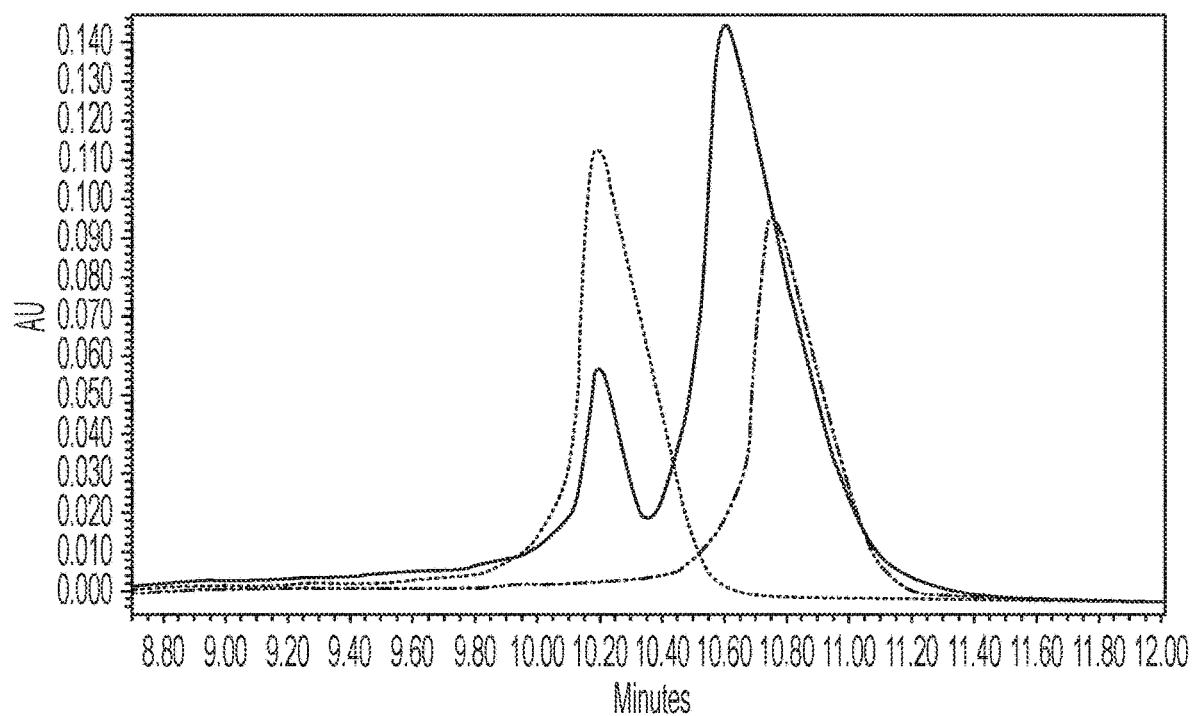
FIG. 13 shows chromatograms demonstrating spike and recovery of the tailless mRNA molecules in a composition of standard full-length molecules having a polyA tail 100 nucleotides in length.
Figure 13:
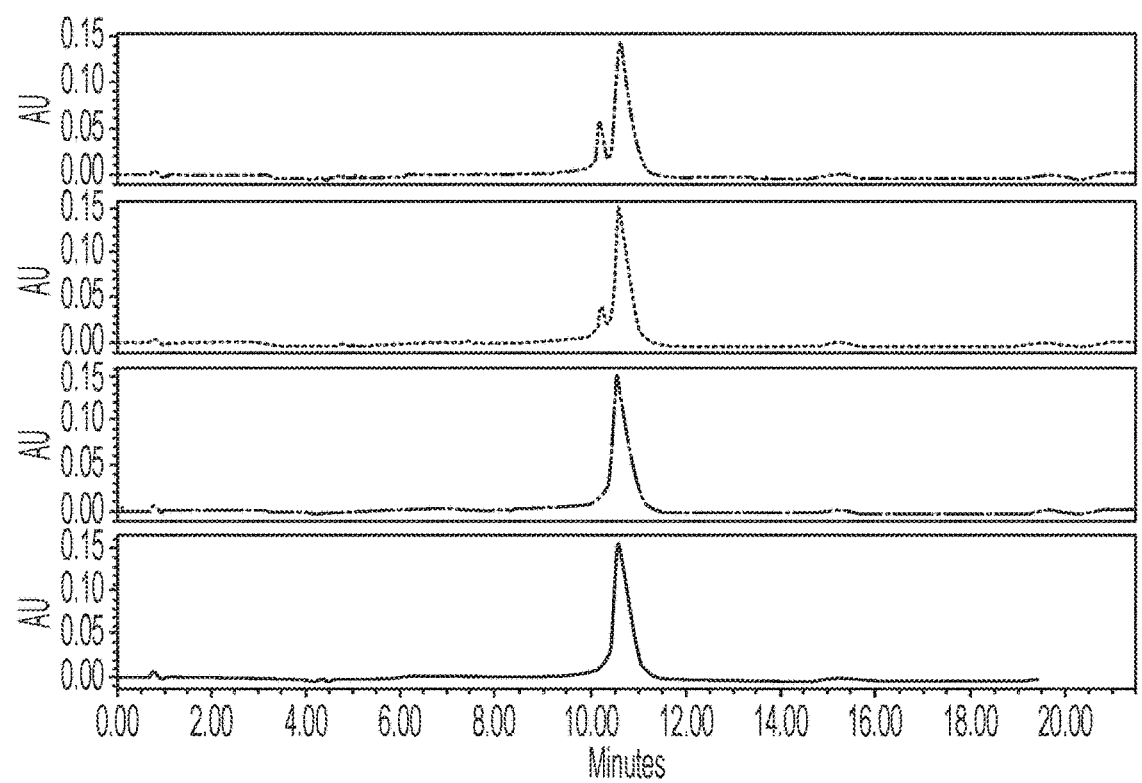

FIG. 13 shows chromatograms demonstrating spike and recovery of the tailless mRNA molecules in a composition of standard full-length molecules having a polyA tail 100 nucleotides in length. Data indicates that HPLC methods described by the disclosure separate tailless and tailed molecules having the same sequence.

Figure 14:
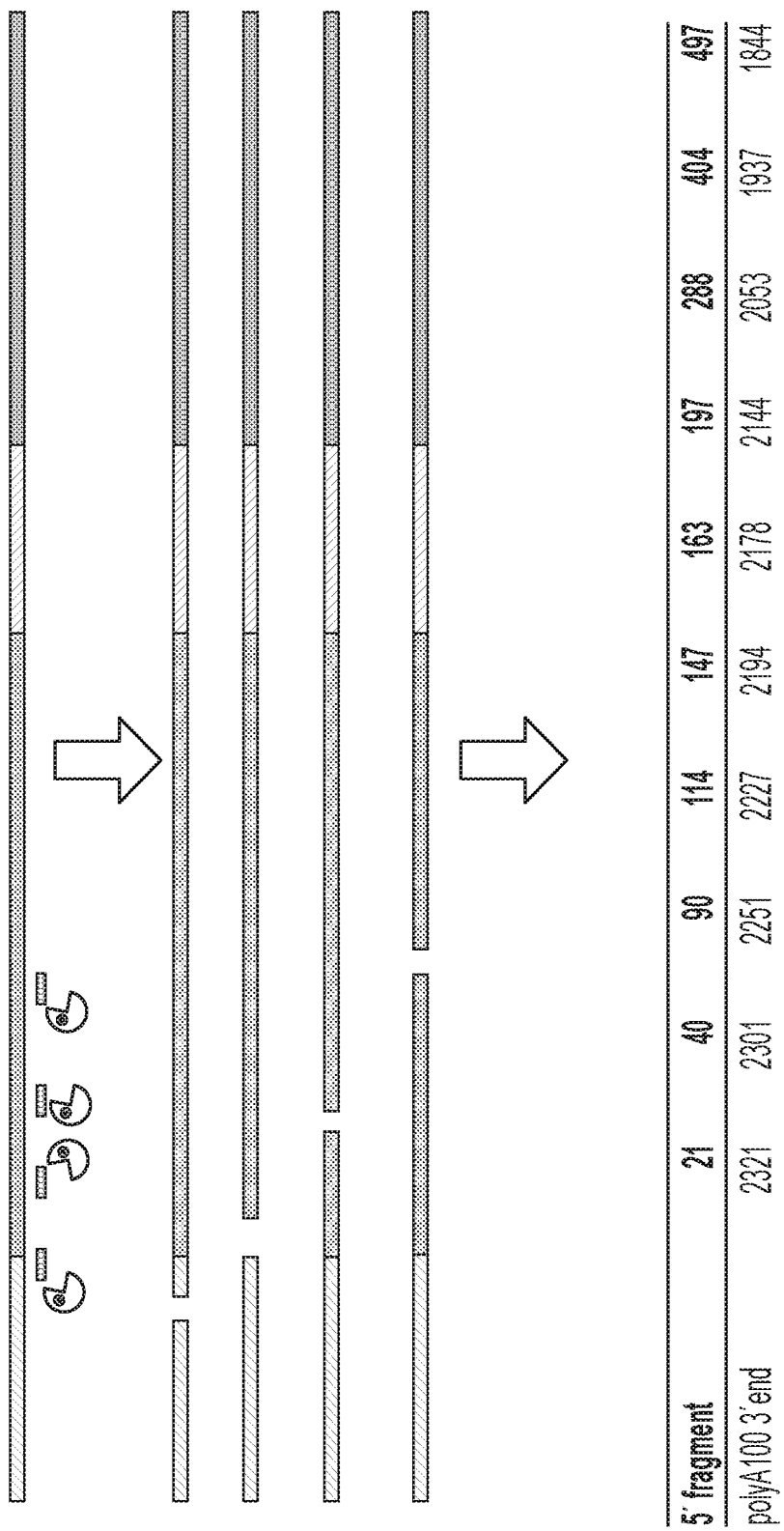
FIG. 14 shows a schematic demonstrating RNase H was used to generate "5' degradants", or long polyadenylated species missing a short length of the 5' end.

FIG. 14 shows a schematic demonstrating RNase H was used to generate "5' degradants", or long polyadenylated species missing a short length of the 5' end. RNase H nicks the RNA side of an RNA/DNA duplex, so by introducing a DNA-containing guide oligo of a specific sequence to an mRNA sample, strand scission can be targeted to a single site on the RNA. The 3' end, or 5'-degraded side, was of interest, in part, because the 5' degradant is a critical product that is not detected by other HPLC methods. By artificially targeting degradation to discrete lengths, the resolution of methods described by the disclosure was probed.

Figure 15:
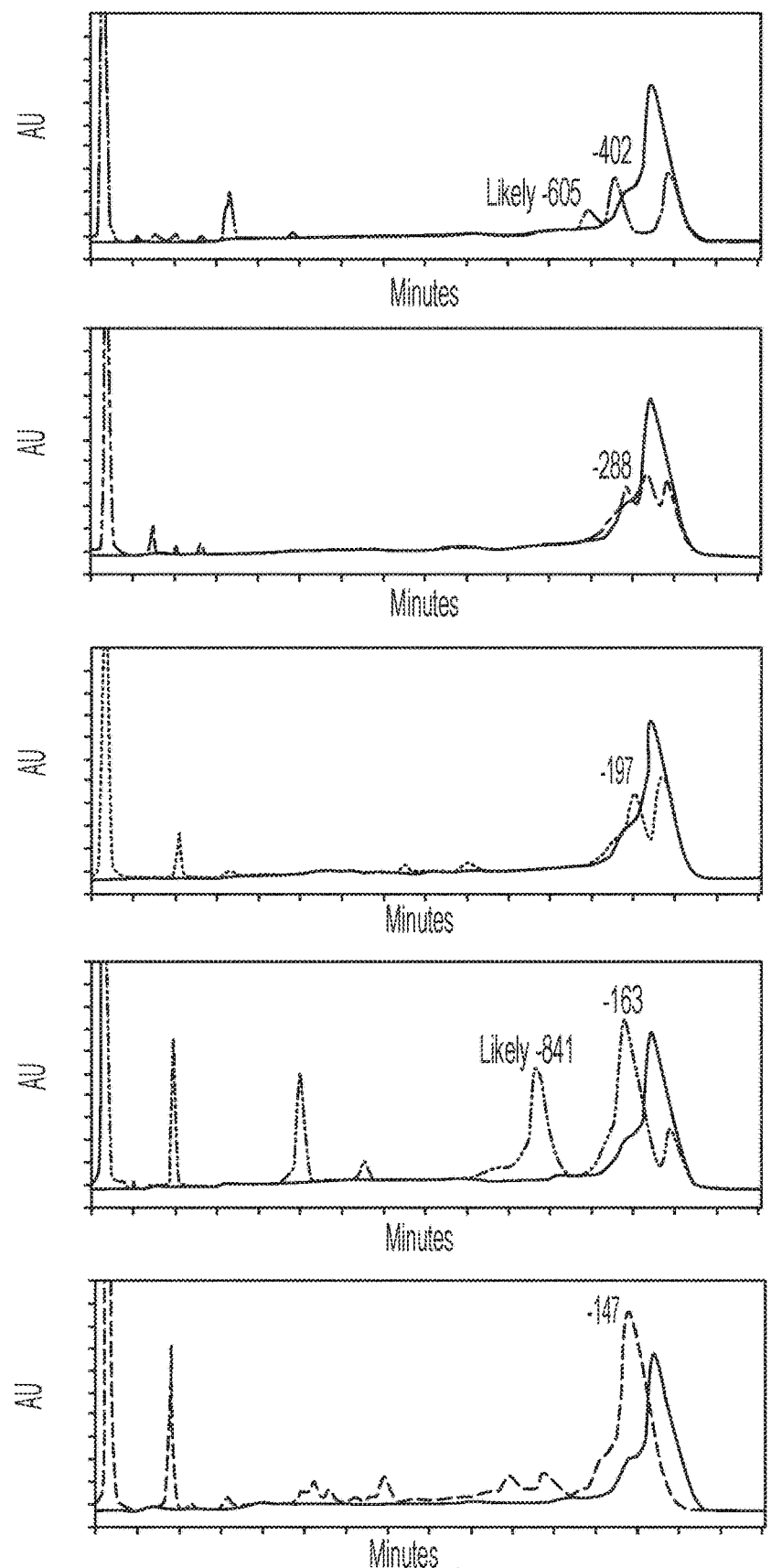
FIG. 15 shows representative chromatograms of 5' degradants separated using HPLC methods described by the disclosure.
Figure 15:
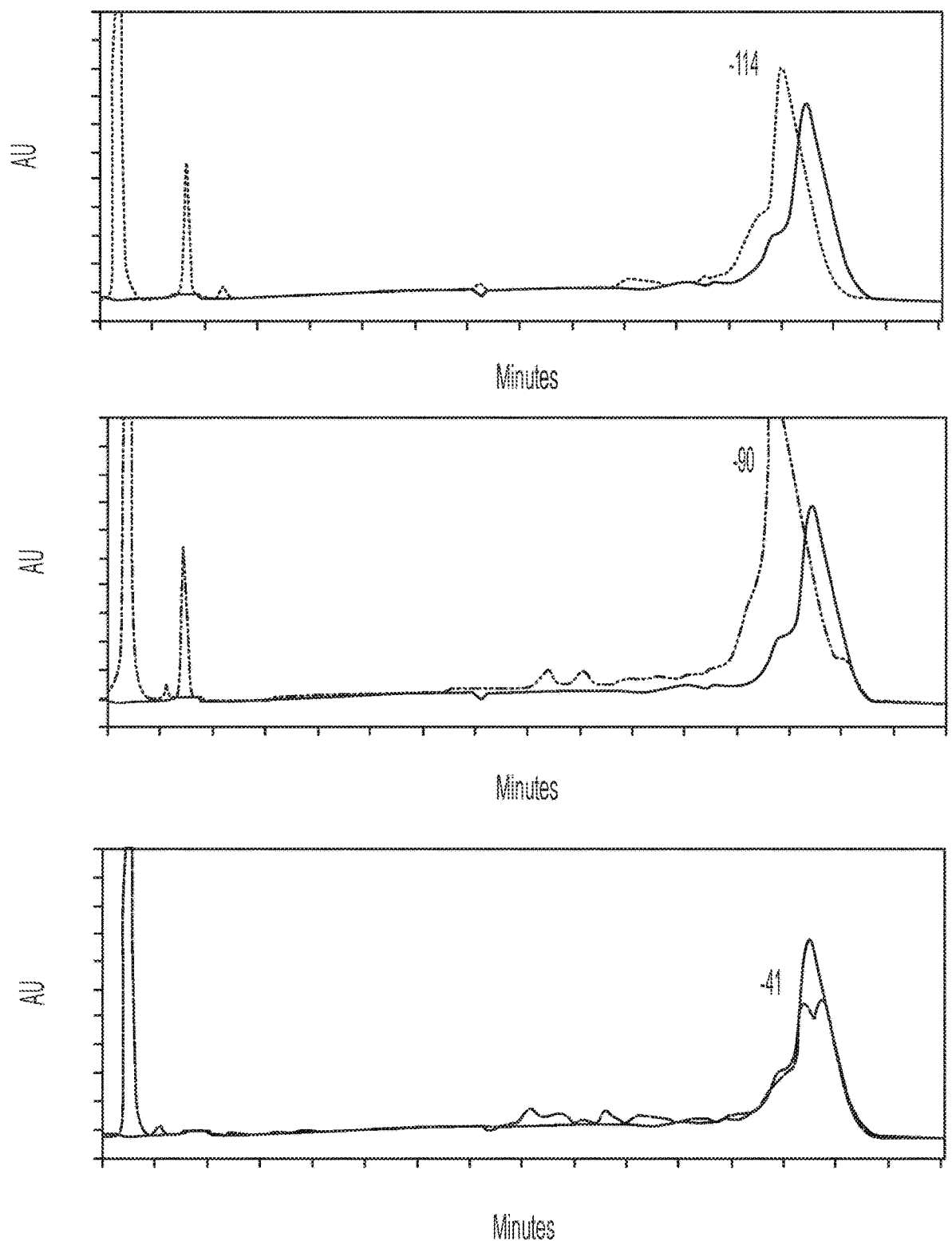

FIG. 15 shows representative chromatograms of 5' degradants separated using HPLC methods described by the disclosure. Full length mRNA is overlaid in black with each crude RNase H reaction. It was observed that separation was achieved down to the −41 reaction, which went to approximately 50% completion as evidenced by the close doublet. On the left side of each chromatogram, the short 5' fragment was detected early in the elution. This two-sided look at the two fragments of the molecule is indicative of the size range observed in random degradation. In addition, a comparison of the −90 or −114 to a tailless standard (FIG. 13), which is essentially −105 on the 3' end, shows the tail bias; much less separation is achieved by removing ~100 bases on the 5' end vs. removing the 100 hydrophobic A's from the 3' end.

Figure 16:
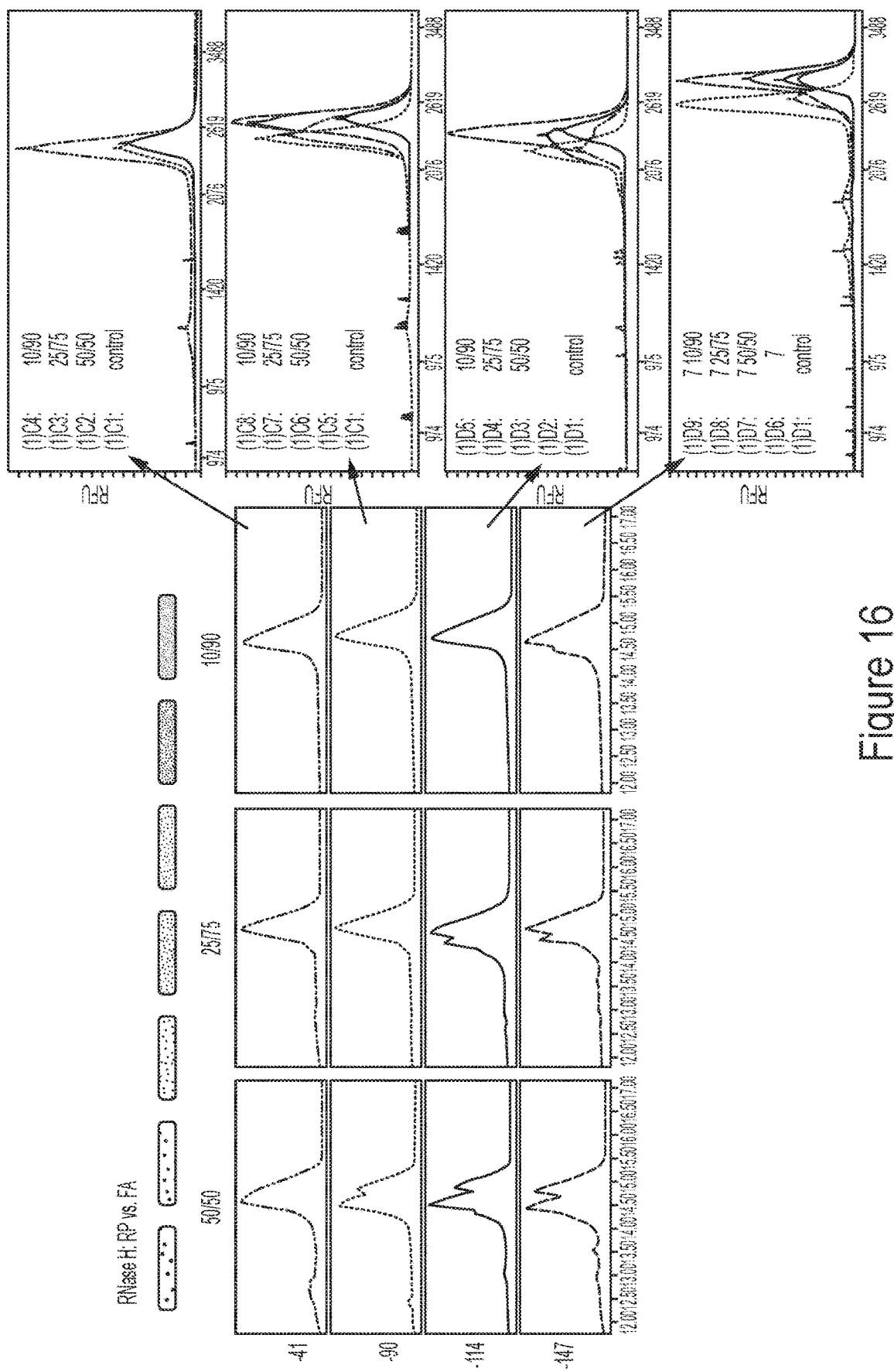
FIG. 16 shows RNaseH 5' degradants of four lengths were purified by a tail-based method to isolate the 5' truncated polyadenylated fragment as an analytical standard. Spike and recovery into full length, tailed mRNA at 50%, 25%, and 10% showed improved resolution and sensitivity for HPLC methods as described by the disclosure compared to FA.
Figure 16:
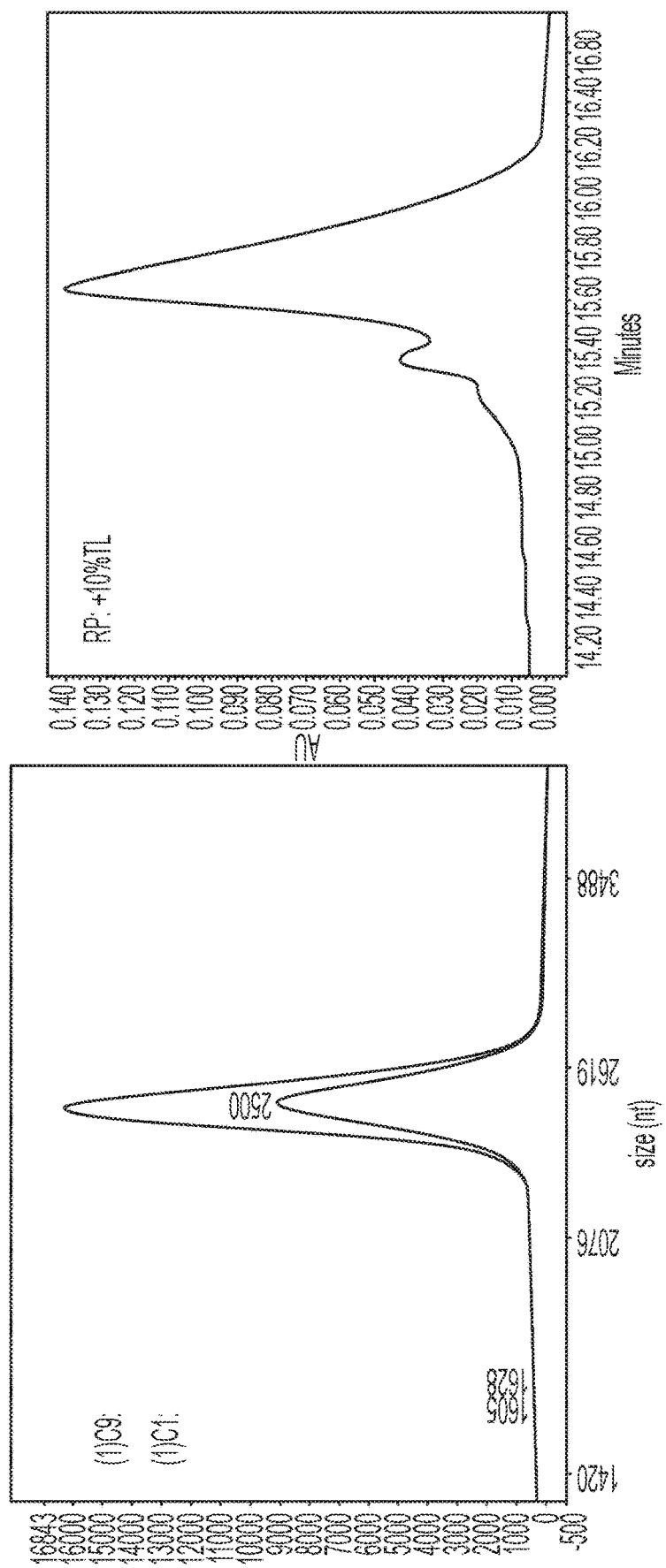

Resolution of degraded products between fragment analyzer (FA) methodology and HPLC methods described by the disclosure were compared. FIG. 16 shows RNaseH 5' degradants of four lengths were purified by a tail-based method to isolate the 5' truncated polyadenylated fragment as an analytical standard. Spike and recovery into full length, tailed mRNA at 50%, 25%, and 10% showed improved resolution and sensitivity for HPLC methods as described by the disclosure compared to FA.

Example 6

Figure 17:
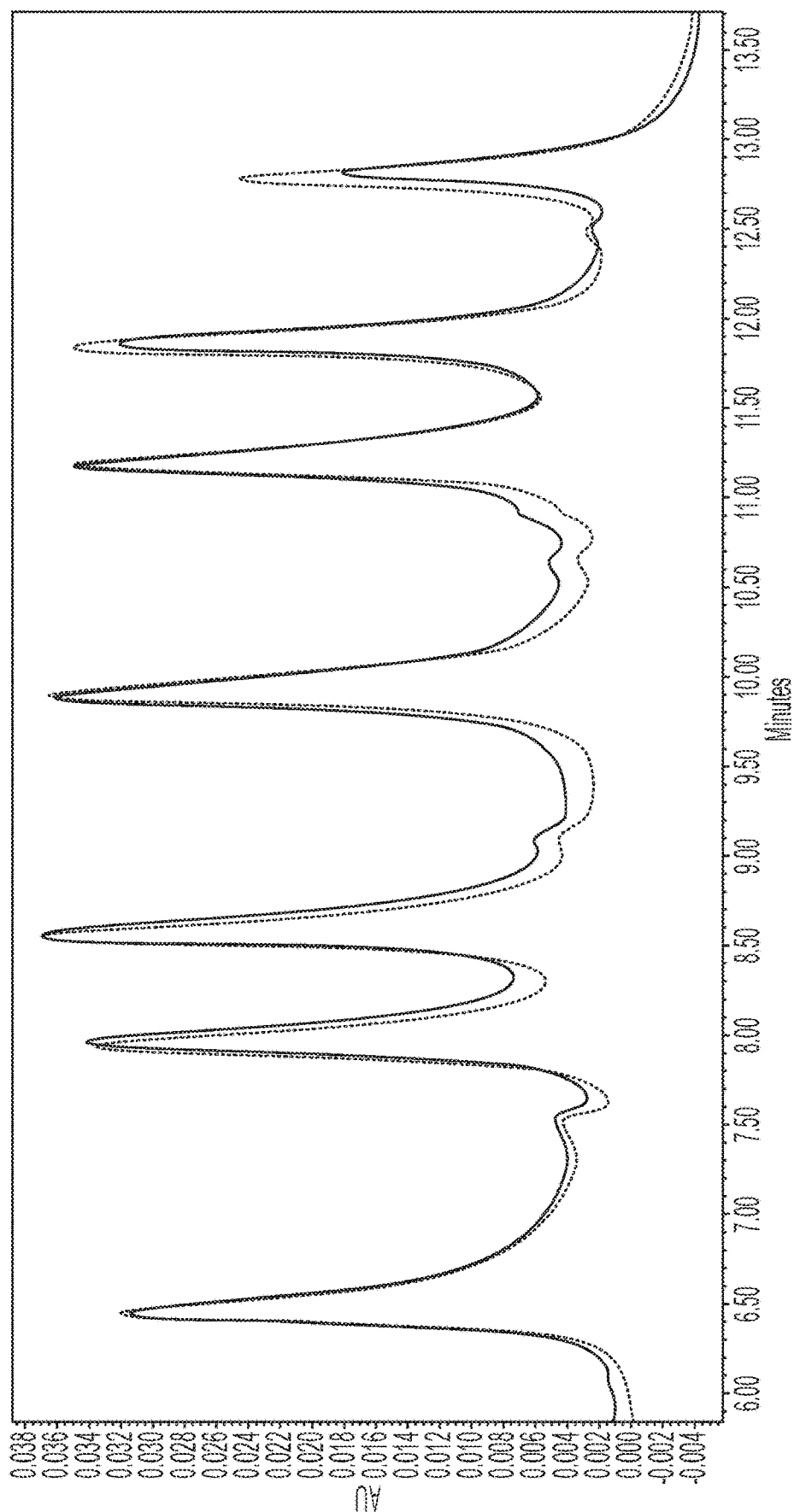
FIG. 17 shows a chromatogram demonstrating HPLC methods described by the disclosure reduce in-run degradation of samples.

Reproducibility of HPLC methods as described by the disclosure was investigated. A mRNA ladder, which was a mixture of seven mRNAs of lengths between 450 net and 3400 nt, was run according to a method as described by the disclosure. The purified fraction was collected and then reinjected to investigate in-run degradation. FIG. 17 is a chromatogram demonstrating that the integrity of the purified fraction is largely preserved, with only small changes to the peak valleys and slight loss of the longest mRNA, which will degrade the fastest compared to the shortest mRNA. The composition of the mRNA ladder before and after reinjection are shown in Table 4.

Table 4

TABLE 4

| LADDER COMPOSITION | |
|---|---|
| INITIAL | REINJECTION |
| 21% | 20% |
| 12% | 13% |
| 15% | 15% |
| 17% | 18% |
| 13% | 14% |
| 11% | 11% |
| 10% | 8% |

Figure 18:
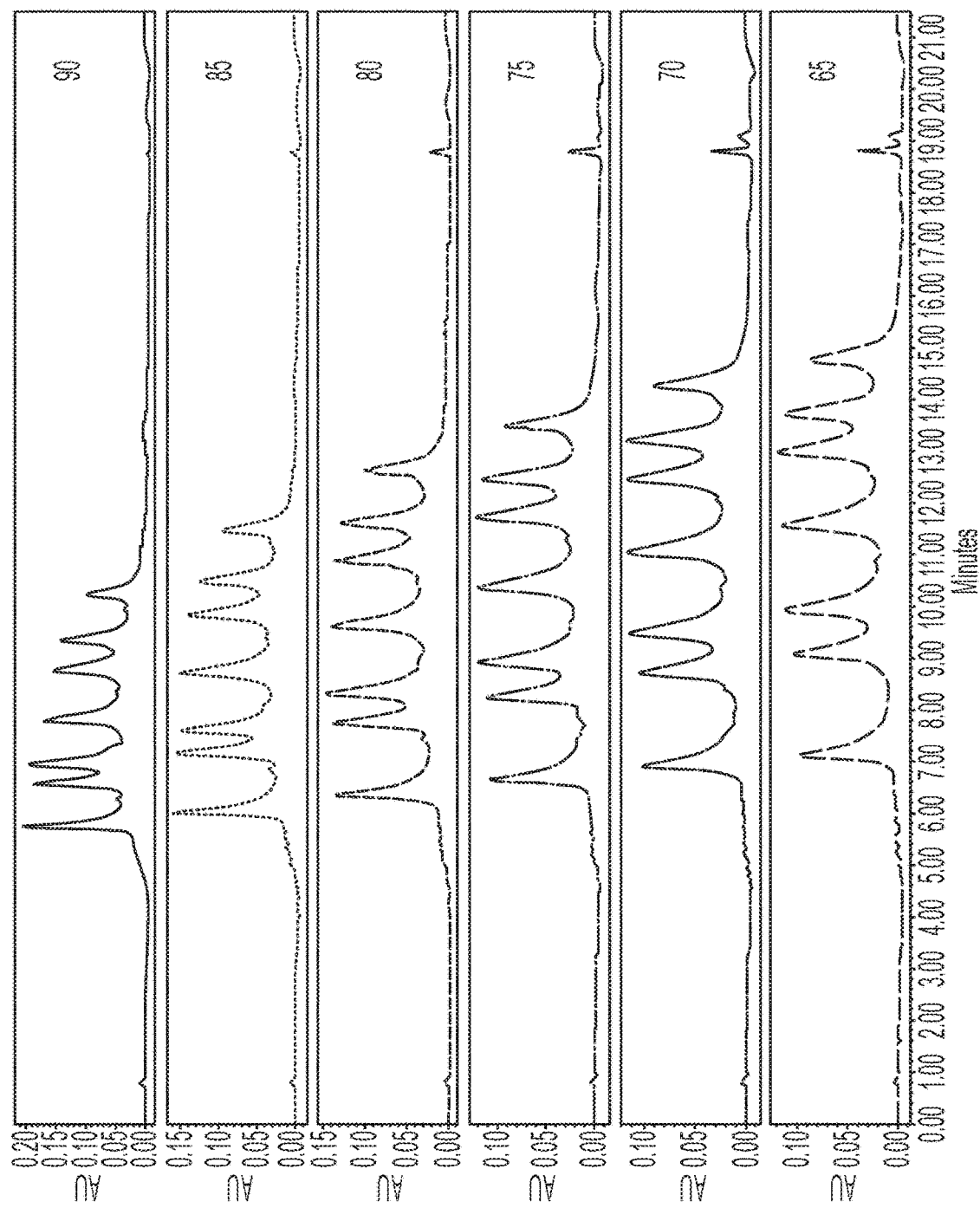
FIG. 18 shows a representative chromatogram of an mRNA ladder demonstrating that temperature robustness of methods described by the disclosure (e.g., resolution and peak area (recovery)) is preserved from 65° C. to 90° C.
Figure 19:
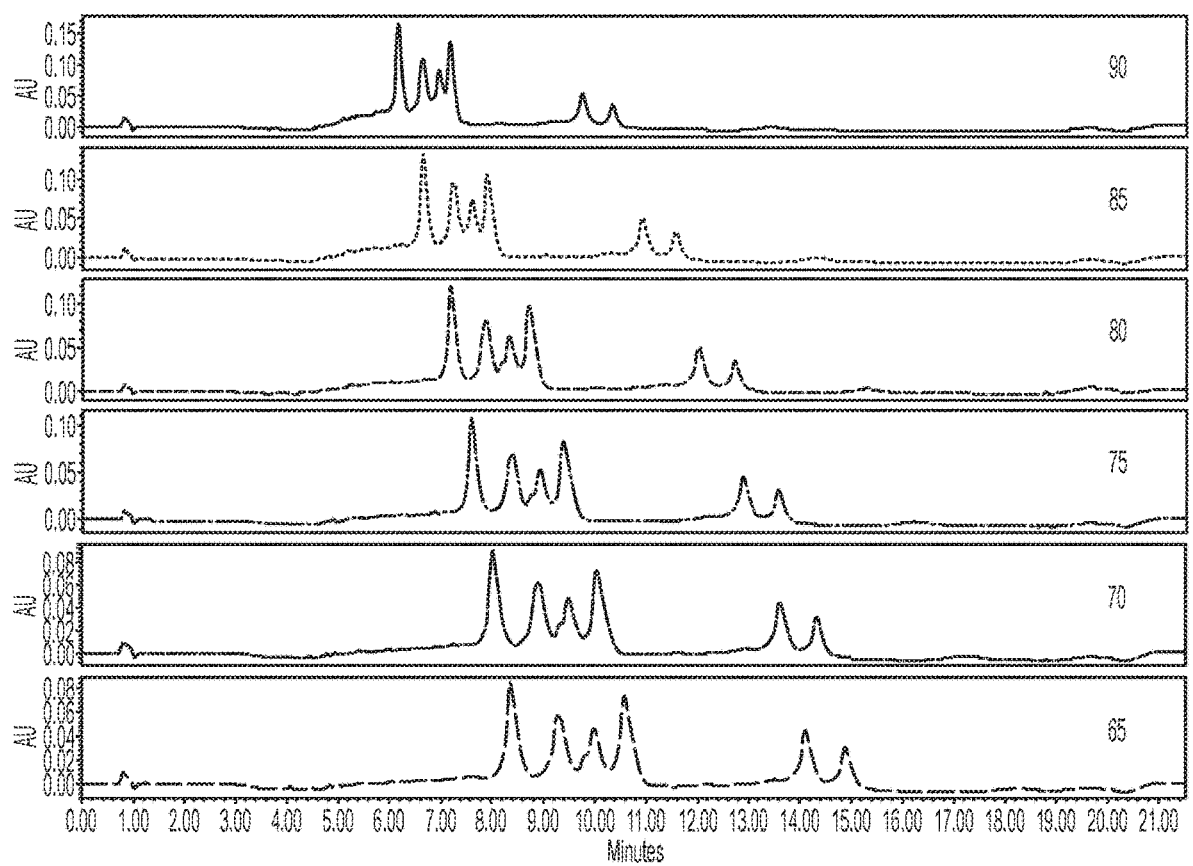
FIG. 19 shows a representative chromatogram of a single species mRNA composition demonstrating that temperature robustness of methods described by the disclosure (e.g., resolution and peak area (recovery)) is preserved from 65° C. to 90° C.
Figure 20:
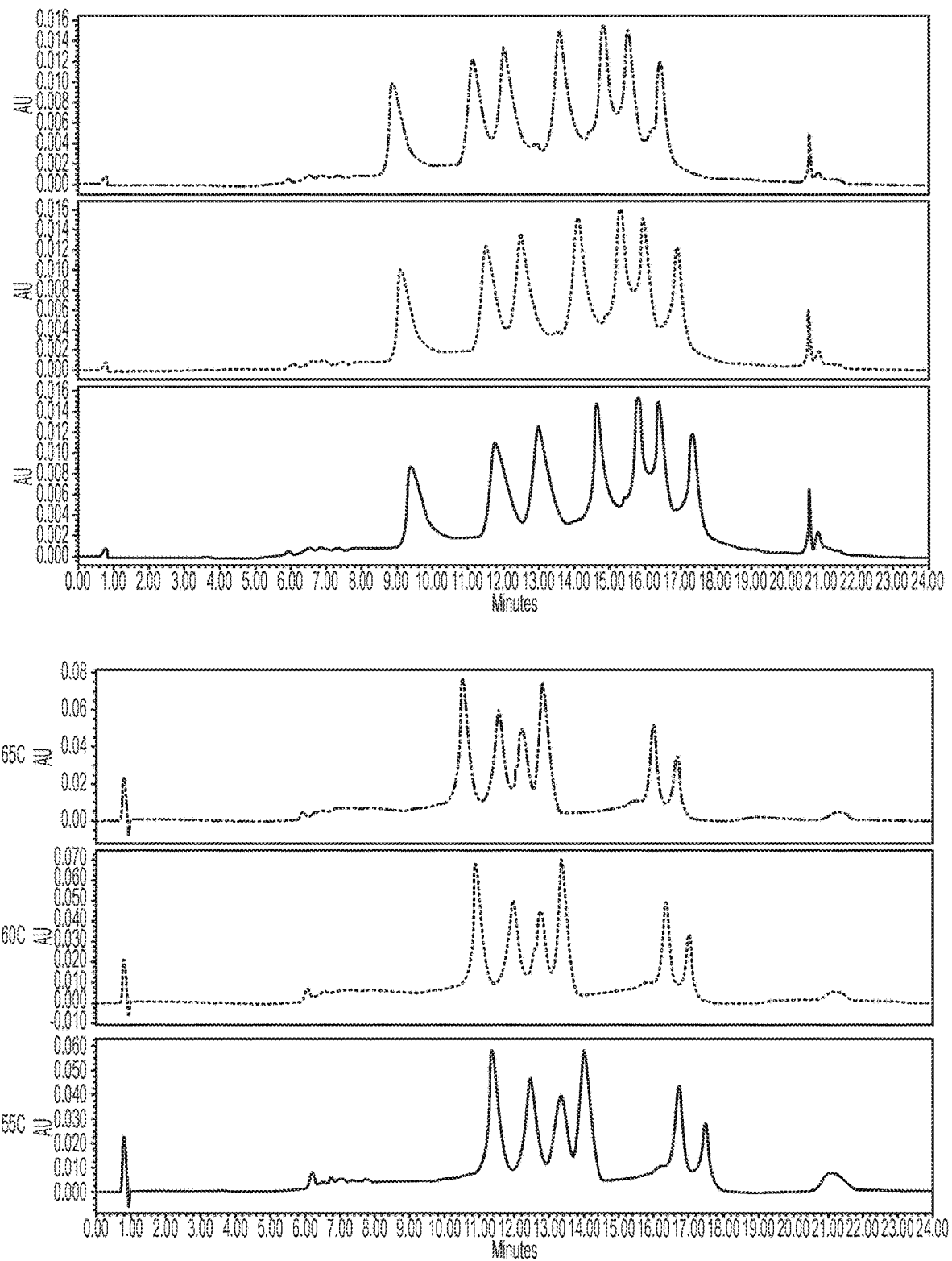
FIG. 20 shows a representative chromatogram demonstrating that temperature robustness of methods described by the disclosure (e.g., resolution and peak area (recovery)) is preserved from 55° C. to 65° C. The chromatogram on top represents a mRNA ladder containing 7 different mRNAs, and the chromatogram on the bottom represents a single drug product comprising six different species of mRNA.
Figure 21:
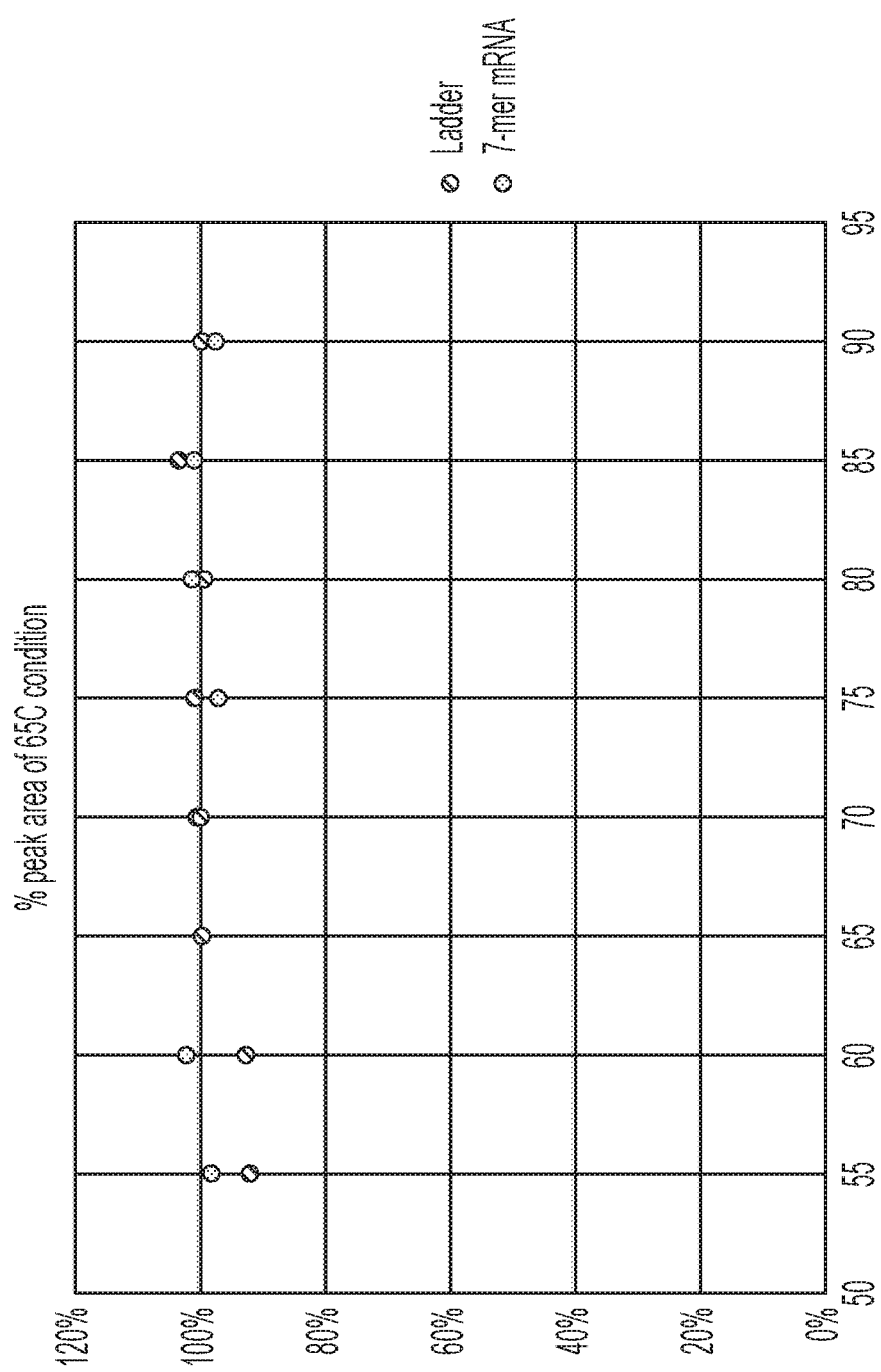
FIG. 21 shows a histogram demonstrating near 100% peak area of HPLC methods as described by the disclosure.

FIGS. 18 and 19 show representative chromatograms demonstrating that temperature robustness of methods described by the disclosure (e.g., resolution and peak area (recovery)) is largely preserved from 55° C. to 90° C. FIG. 18 depicts a chromatogram of the mRNA ladder described above, while FIG. 19 depicts a single-species mRNA composition. The significance of temperature robustness is that the temperature of analysis can be reduced to minimize in-run degradation, without adding analytical artifacts or losing recovery. Temperature robustness was also preserved at lower temperatures (FIG. 20). FIG. 21 shows a histogram demonstrating near 100% peak area of HPLC methods as described by the disclosure.

Example 7

Figure 22:
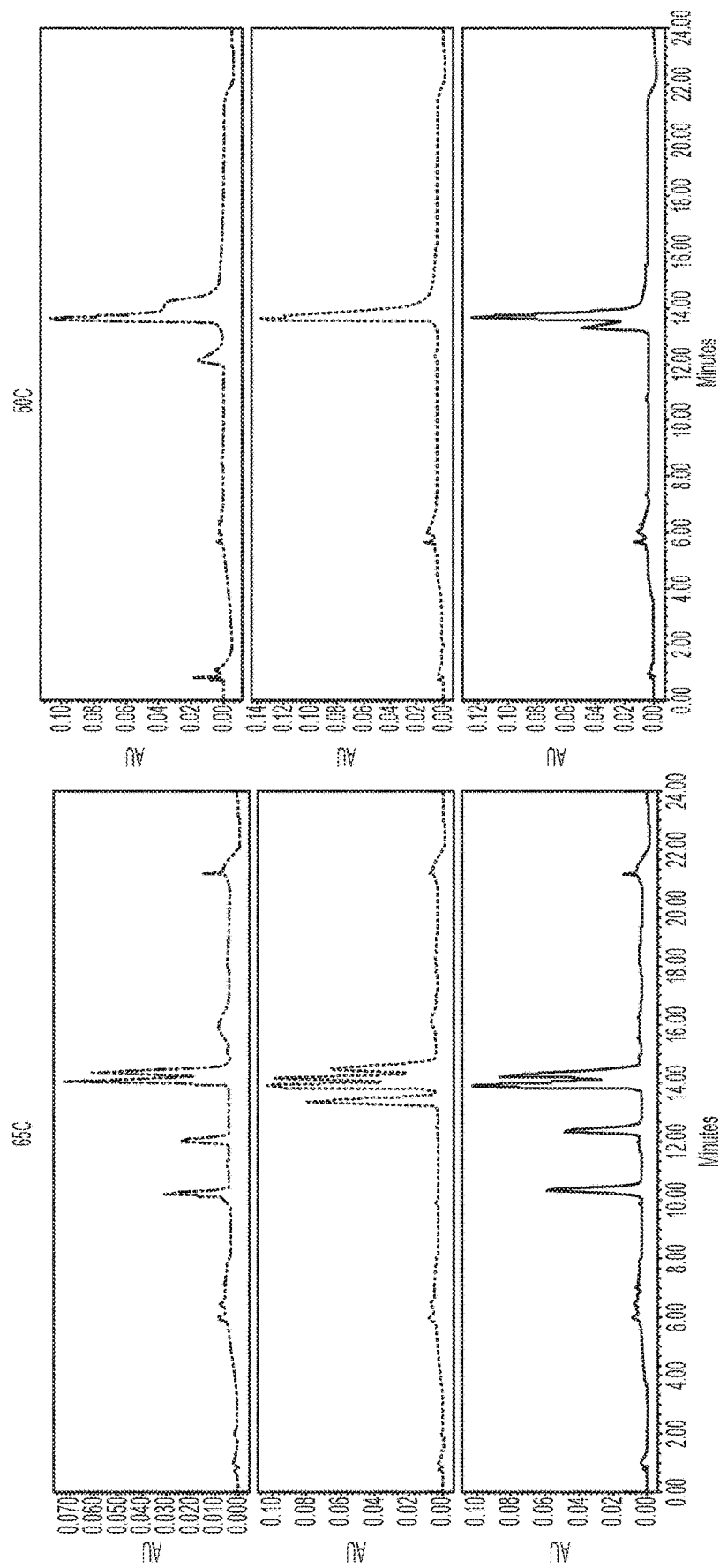
FIG. 22 shows analysis of three linearized plasmid templates (e.g., the same vector) comprising genes of different lengths using HPLC methods described by the disclosure at 65° C. and 50° C. At the former temperature, both the polyT and polyA gene strands, as well as the two vector strands, were separated (vector doublet eluting at ~14 minutes). At 50° C., the two of the double-stranded genes were separated from the double-stranded vector (top and bottom); the third gene is very close to the length of the vector and nearly coelutes (middle).

Methods described by the disclosure were applied for analysis of a DNA template. It was observed that the DNA template was slightly more retained than RNA of the same size, due to increased hydrophobicity, but elutes within the same acetonitrile range (25-28%) under the conditions specified above. Temperature may also be varied to either stabilize or denature the DNA duplex. FIG. 22 shows analysis of three linearized plasmid templates (e.g., the same vector) comprising genes of different lengths using HPLC methods described by the disclosure at 65° C. and 50° C. At the former temperature, both the polyT and polyA gene strands, as well as the two vector strands, were separated (vector doublet eluting at ~14 minutes). At 50° C., the two of the double-stranded genes were separated from the double-stranded vector (top and bottom); the third gene is very close to the length of the vector and nearly coelutes (middle).

What is claimed is:

1. A method of separating a first messenger ribonucleic acid mRNA from a mixture, the mixture comprising the first m RNA and at least a second mRNA, and further comprising one or more impurities or at least a third nucleic acid, comprising the steps:
   i. contacting a stationary phase of a reverse phase chromatography column with the mixture; and
   ii. eluting the first m RNA with a mobile phase, wherein the mobile phase comprises one or more solvents and two or more ion pairs, wherein at least one ion pair is a size-selective ion pair comprising four or more carbon atoms per alkyl chain, and at least one ion pair is a composition-selective ion pair having three or fewer carbon atoms per alkyl chain, such that the first mRNA traverses the column with a retention time that is different than a retention time of the second mRNA or different than a retention time of the one or more impurities or different than a retention time of the third nucleic acid of the mixture thereby isolating the first mRNA from the second mRNA or isolating the first m RNA from the one or more impurities or isolating the first m RNA from the third nucleic acid of the mixture or isolating the first m RNA from the second mRNA, the third mRNA, and the one or more impurities.

2. The method of claim 1, wherein the stationary phase comprises particles.

3. The method of claim 1, wherein the mobile phase is:
   (i) one solvent;
   (ii) a mixture of a first solvent and a second solvent; or
   (iii) a mixture of a first solvent solution and a second solvent solution.

4. The method of claim 1, wherein the mobile phase is a mixture of (i) a first solvent solution and (ii) a second solvent solution, wherein the first solvent solution comprises one or more solvents and one or more ion pairs, and wherein the second solvent solution comprises one or more solvents and one or more ion pairs.

5. The method of claim 4, wherein the first solvent solution and/or the second solvent solution comprises one or more solvents independently selected from the group consisting of water, polar aprotic solvents, $C_{1-4}$ alkanols, $C_{1-6}$ alkanediols, and $C_{2-4}$ alkanoic acids.

6. The method of claim 1, wherein step (ii) comprises: passing the mobile phase through the column, wherein the mobile phase is a mixture of a first solvent solution and a second solvent solution, and wherein the first solvent solution and the second solvent solution independently comprise one or more ion pairs selected from the group consisting of a triethylammonium salt.

7. The method of claim 1, wherein the first mRNA comprises 5' and 3' UTRs; a 5' 7-methylguanosine group or a 5' 7-methylguanosine cap analog; a 3'-polyadenosine tail; or a combination thereof.

8. The method of claim 1, further comprising the step of detecting or isolating the second mRNA and/or the one or more impurities or third nucleic acid.

9. The method of claim 1, wherein said eluting is isocratic with respect to a solvent composition of the mobile phase.

10. The method of claim 9, wherein said eluting is isocratic or gradient with respect to a concentration of the two or more ion pairs.

11. The method of claim 10, wherein the mobile phase comprises two ion pairs, and a relative concentration of the ion pairs is varied during the eluting.

12. The method of claim 1, wherein said eluting is gradient with respect to a solvent composition of the mobile phase.

13. The method of claim 12, wherein said eluting is isocratic or gradient with respect to the concentration of one or more ion pairs.

14. The method of claim 1, wherein:
   (i) the at least one size-selective ion pair is selected from the group consisting of a tetrabutylammonium salt, hexylammonium salt, and dibutylammonium salt; and
   (ii) the at least one composition-selective ion pair is a triethylammonium salt.

15. The method of claim 14, wherein:
   (i) the at least one size-selective ion pair is selected from the group consisting of tetrabutylammonium phosphate (TBAP), hexylammonium acetate (HAA), and dibutylammonium acetate (DBAA); and
   (ii) the at least one composition-selective ion pair is triethylammonium acetate (TEAA).

16. The method of claim 4, wherein each of the first and second solvent solutions comprises at least one of the two or more ion pairs in a concentration of about 1 mM to about 100 mM.

* * * * *